(12) United States Patent
Otsuji et al.

(10) Patent No.: US 11,999,972 B2
(45) Date of Patent: Jun. 4, 2024

(54) FIBRONECTIN FRAGMENT TO BE USED FOR STEM CELL PRODUCTION

(71) Applicant: TAKARA BIO INC., Shiga (JP)

(72) Inventors: Tomomi Otsuji, Kusatsu (JP); Toshikazu Nishie, Kusatsu (JP); Risa Kato, Kusatsu (JP); Sachiko Okamoto, Kusatsu (JP); Tatsuji Enoki, Kusatsu (JP); Junichi Mineno, Kusatsu (JP)

(73) Assignee: TAKARA BIO INC., Shiga (JP)

( * ) Notice: Subject to any disclaimer, the term of this patent is extended or adjusted under 35 U.S.C. 154(b) by 603 days.

(21) Appl. No.: 16/321,112

(22) PCT Filed: Jul. 28, 2017

(86) PCT No.: PCT/JP2017/027485
§ 371 (c)(1),
(2) Date: May 6, 2019

(87) PCT Pub. No.: WO2018/021543
PCT Pub. Date: Feb. 1, 2018

(65) Prior Publication Data
US 2021/0254018 A1 Aug. 19, 2021

(30) Foreign Application Priority Data
Jul. 29, 2016 (JP) ................................. 2016-149495

(51) Int. Cl.
| | |
|---|---|
| *C12N 5/074* | (2010.01) |
| *A61K 38/39* | (2006.01) |
| *C07K 14/78* | (2006.01) |
| *C12M 1/00* | (2006.01) |
| *C12M 1/12* | (2006.01) |

(52) U.S. Cl.
CPC ............ *C12N 5/0696* (2013.01); *A61K 38/39* (2013.01); *C07K 14/78* (2013.01); *C12M 25/06* (2013.01); *C12M 23/20* (2013.01); *C12N 2533/52* (2013.01)

(58) Field of Classification Search
CPC .. C12N 5/0696; C12N 2533/52; A61K 38/39; C07K 14/78; C12M 25/06; C12M 23/20
USPC ........................................................ 514/9.3
See application file for complete search history.

(56) References Cited

U.S. PATENT DOCUMENTS

| | | | |
|---|---|---|---|
| 5,198,423 A | 3/1993 | Taguchi et al. | |
| 6,472,204 B1 | 10/2002 | Asada et al. | |
| 2010/0150886 A1 | 6/2010 | Marui et al. | |

FOREIGN PATENT DOCUMENTS

| | | |
|---|---|---|
| JP | 2-311498 | 12/1990 |
| WO | 97/11604 | 4/1997 |
| WO | 97/18318 | 5/1997 |
| WO | WO 2011126833 | * 10/2011 |
| WO | 2011/156639 | 12/2011 |

OTHER PUBLICATIONS

Office Action issued Feb. 16, 2021 in corresponding Japanese Patent Application No. 2018-530429, with English Machine Translation.
International Search Report issued Oct. 3, 2017 in International Application No. PCT/JP2017/027485.
International Preliminary Report on Patentability issued on Feb. 7, 2019 in International Application No. PCT/JP2017/027485.
Kalaskar, D.M. et al., "Characterization of the interface between adsorbed fibronectin and human embryonic stem cells", J R Soc Interface, 2013, vol. 10, 20130139.
Marchenko, S. et al., "Passing Human Neural Stem Cells", Journal of Visualized Experiments, 2007, vol. 7, 263.
Official Communication issued Jun. 21, 2021 in corresponding European Patent Application No. 17834545.0.
Extended European Search Report issued Jan. 17, 2020 in corresponding European Patent Application No. 17834545.0.
Decision of Refusal issued Sep. 7, 2021 in corresponding Japanese Patent Application No. 2018-530429, with English Machine Translation, 13 pages.
Official Communication issued Dec. 4, 2020 in corresponding European Patent Application No. 17834545.0.
Official Action issued Dec. 24, 2020 in corresponding Korean Patent Application No. 10-2019-7004663, with partial English translation.
Sechler et al., "A novel fibronectin binding site required for fibronectin fibril growth during matrix assembly", The Journal of Cell Biology, 2001, vol. 154, No. 5, pp. 1081-1088.
Office Action issued Dec. 31, 2021 in corresponding Chinese Patent Application No. 201780058969.6, with English Translation, 32 pages.
Office Action issued May 24, 2022 in corresponding Chinese Patent Application No. 20170058969.6, with English translation, 10 pages.
Decision on Refusal issued Mar. 28, 2023 in corresponding Japanese Patent Application No. 2021-197695, with English translation, 16 pages.
Decision on Rejection issued Oct. 18, 2022 in corresponding Chinese Patent Application No. 201780058969.6, with English translation, 11 pages.
Office Action issued Nov. 22, 2022 in corresponding Japanese Patent Application No. 2021-197695, with English translation, 10 pages.

* cited by examiner

*Primary Examiner* — Jennifer M. H. Tichy
(74) *Attorney, Agent, or Firm* — Wenderoth, Lind & Ponack, L.L.P.

(57) ABSTRACT

Stem cells can be efficiently proliferated by culturing the stem cells in the presence of a novel recombinant fibronectin fragment.

6 Claims, 3 Drawing Sheets
Specification includes a Sequence Listing.

[Fig 1]
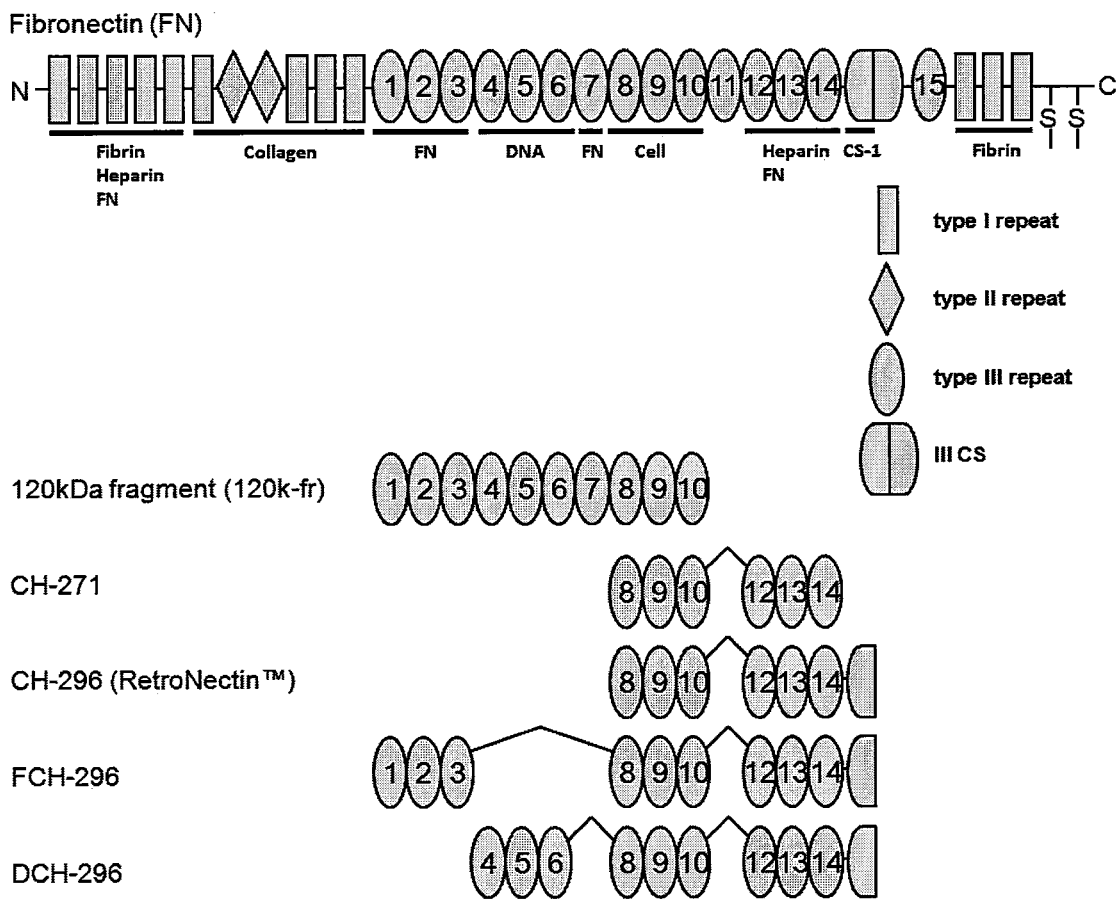
[Fig.2]
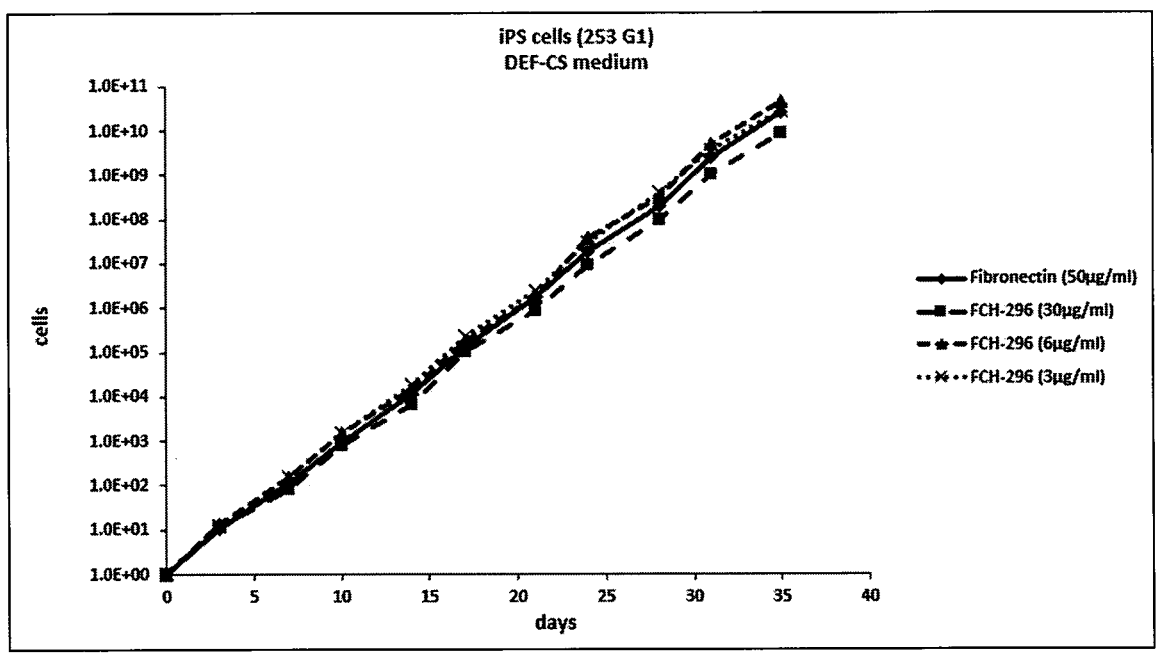

[Fig3]
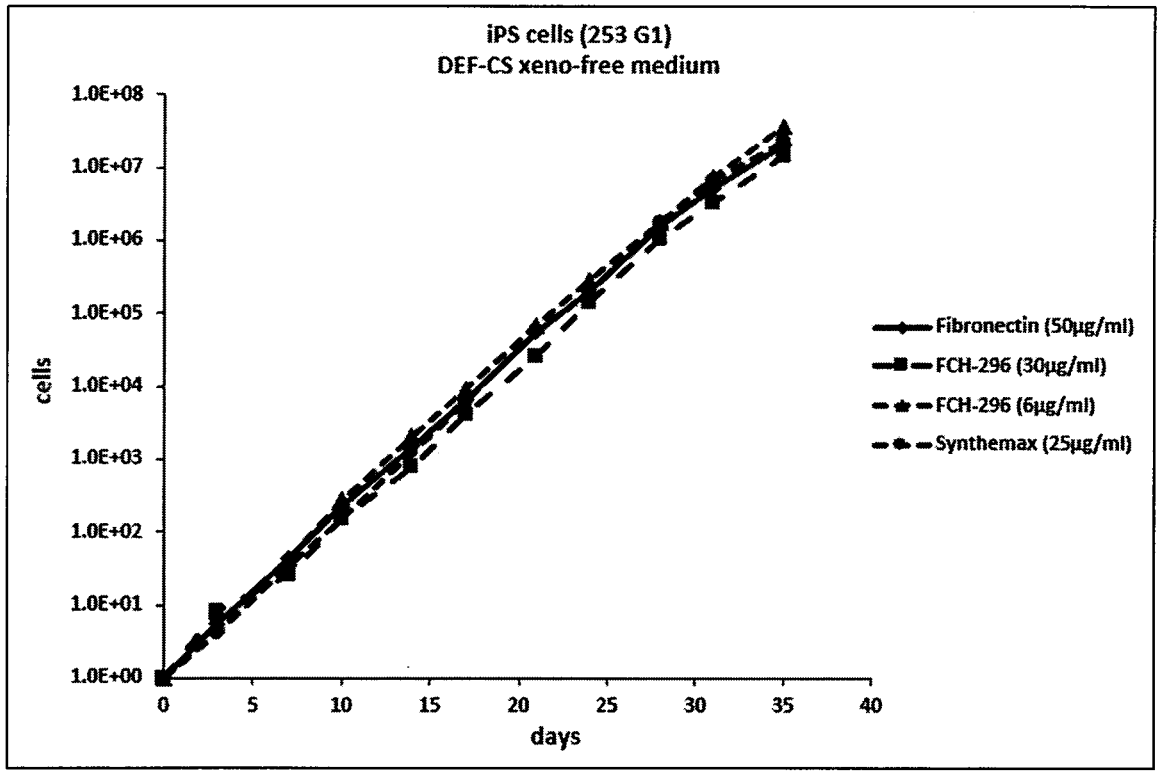
[Fig 4]
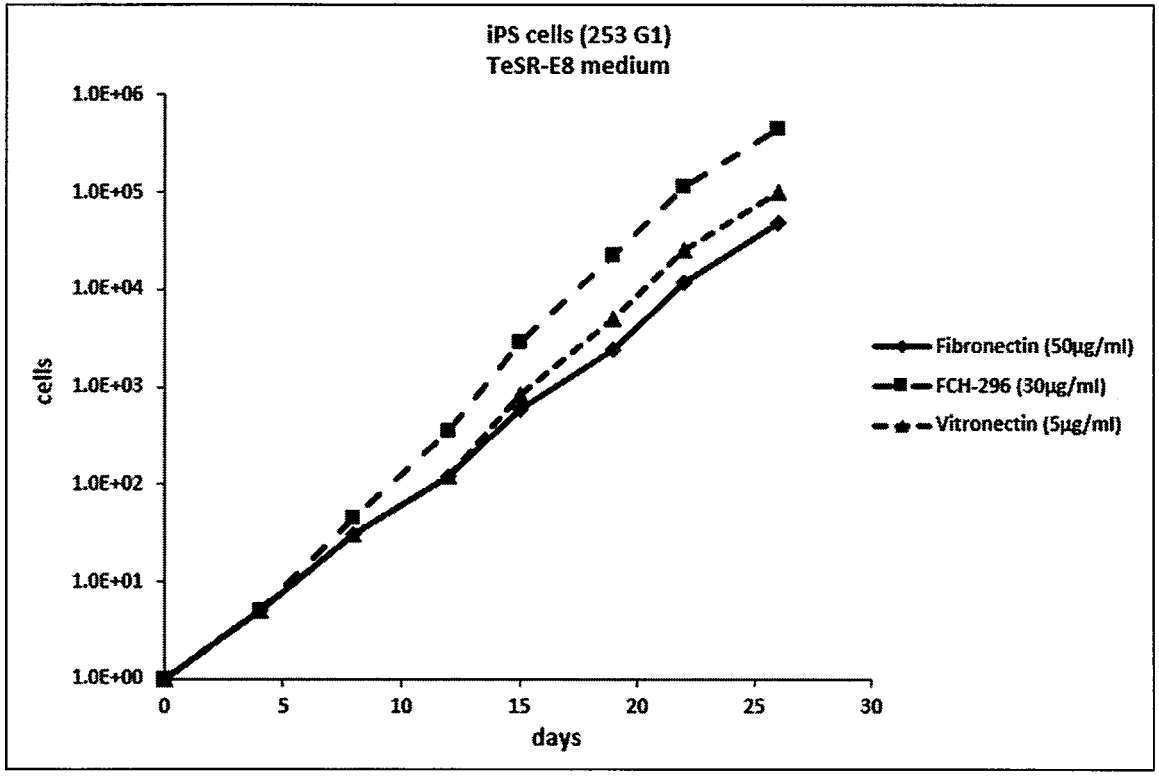

[Fig.5]
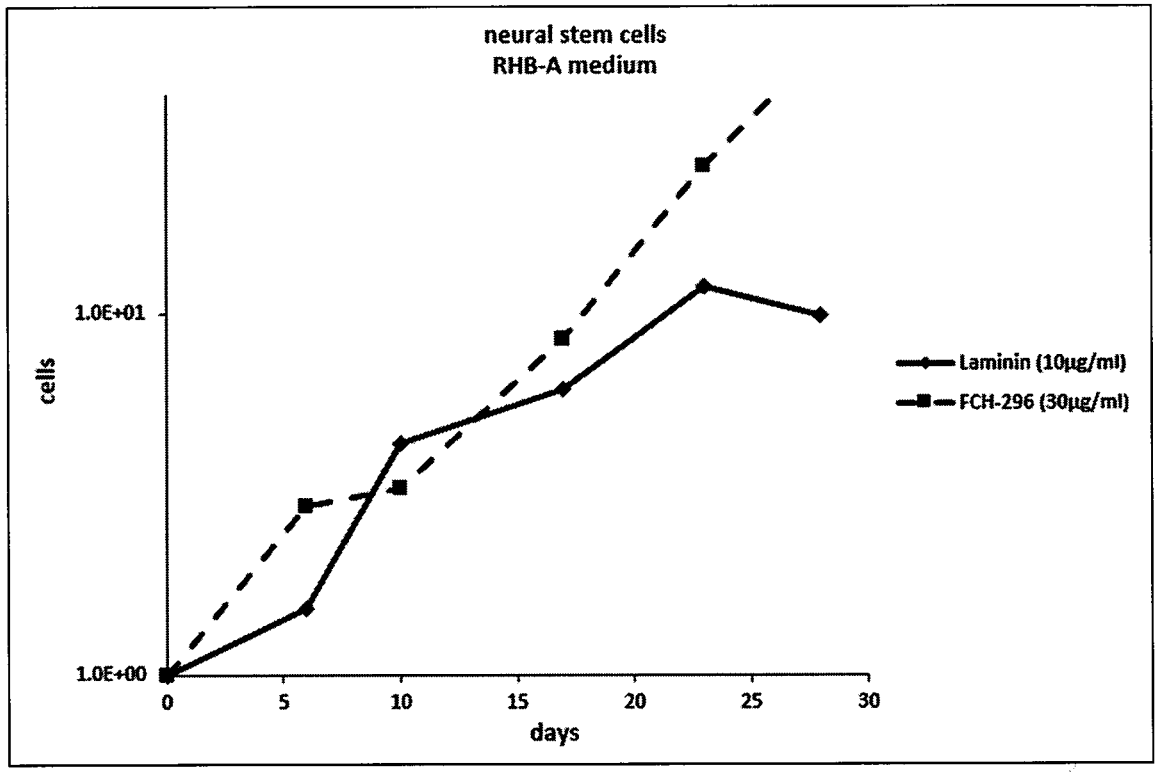
[Fig.6]
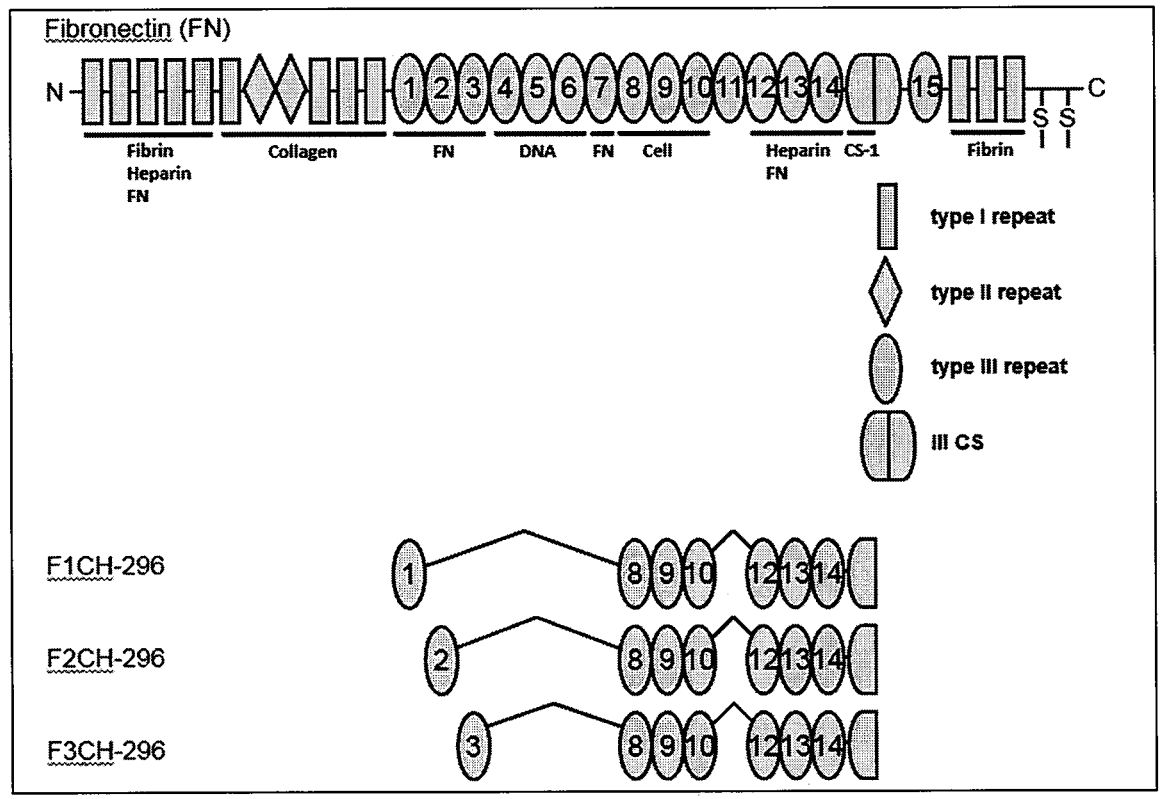

FIBRONECTIN FRAGMENT TO BE USED FOR STEM CELL PRODUCTION

TECHNICAL FIELD

The present invention relates to a process for producing stem cells that retain the ability to differentiate into various cells.

BACKGROUND ART

A stem cell is defined as a cell that has the ability to divide to produce the same cell as itself (self-renewal ability) and the ability to differentiate into another type of cell and can proliferate infinitely. Differentiated cells can be supplied when at least one of two daughter cells generated from a stem cell continues to be the same cell as the stem cell.

At present, research is underway actively as to the process for preparing stem cells. For example, a mouse-derived feeder cell, Matrigel, an extracellular matrix such as laminin and fibronectin and the like can be used as a substrate for culturing stem cells.

For example, Non-Patent Document 1 can be cited as a study on a process for preparing stem cells utilizing fibronectin or a fibronectin fragment. Non-Patent Document 1 discloses a method for making human embryonic stem cells (ES cells) proliferate while maintaining their pluripotency, which comprises culturing the human ES cells on a 120 kDa fibronectin fragment (hereinafter referred to as 120 k-fr). However, the proliferation rate of the cells on 120 k-fr was slower than the proliferation rate on full-length fibronectin. In addition, in order for stem cells to be used in regenerative medicine, it is necessary to ensure quality and safety, but since full-length fibronectin and commercially available 120 k-fr are derived from natural fibronectin, there is a high risk that viruses and the like possessed by origin organisms are brought in.

As described above, a technique for producing a sufficient amount of stem cells in a short period of time by using fibronectin or a fibronectin fragment has not yet been established.

PRIOR ART DOCUMENT

Non-Patent Document

Non-Patent Document 1: Journal of The Royal Society Interface, Vol. 10, No. 83, 20130139 (2013)

DISCLOSURE OF INVENTION

Problems to be Solved by the Invention

An object of the present invention is to solve the problems of the conventional process for producing stem cells and to provide a process for producing a large amount of stem cells in a short period of time by using a fibronectin fragment.

Solutions to the Problems

As a result of intensive studies to solve the above-described problems, the present inventors have found that stem cells efficiently proliferate by culturing stem cells in the presence of a novel recombinant fibronectin fragment, and have completed the present invention.

Specifically, the present invention relates to the followings:

[1] A process for producing a stem cell, the process comprising the step of culturing the stem cell in the presence of:
  (a) a recombinant polypeptide comprising a repeat selected from the group consisting of human fibronectin III-1 to 7, or a recombinant polypeptide comprising an amino acid sequence having substitution, deletion, insertion or addition of one or several amino acids in the amino acid sequence of the repeat selected from the group consisting of the III-1 to 7;
  (b) a recombinant polypeptide comprising human fibronectin III-8 to 10 repeats, or a recombinant polypeptide comprising an amino acid sequence having substitution, deletion, insertion or addition of one or several amino acids in the amino acid sequence of the III-8 to 10 repeats; and
  (c) a recombinant polypeptide comprising human fibronectin III-12 to 14 repeats, or a recombinant polypeptide comprising an amino acid sequence having substitution, deletion, insertion or addition of one or several amino acids in the amino acid sequence of the III-12 to 14 repeats;
[2] The production process according to [1], comprising the step of culturing the stem cell in the presence of a recombinant polypeptide including the recombinant polypeptides (a), (b) and (c) in the same molecule;
[3] The production process according to [1] or [2], wherein the recombinant polypeptide (a) is a recombinant polypeptide comprising human fibronectin III-1 to 3 repeats or III-4 to 6 repeats, or a recombinant polypeptide comprising an amino acid sequence having substitution, deletion, insertion or addition of one or several amino acids in the amino acid sequence of the III-1 to 3 repeats or the III-4 to 6 repeats;
[4] The production process according to [3], wherein the recombinant polypeptide is a recombinant polypeptide comprising an amino acid sequence of SEQ ID NO: 19 or 20, or a recombinant polypeptide comprising an amino acid sequence having substitution, deletion, insertion or addition of one or several amino acids in the amino acid sequence of SEQ ID NO: 19 or 20;
[5] The production process according to any one of [1] to [4], wherein the step of culturing the stem cell in the presence of the recombinant polypeptides is performed in a state where a solid phase coated with the recombinant polypeptides is in contact with the stem cell;
[6] The production process according to [5], wherein the solid phase is a device for cell culture or a carrier for cell culture;
[7] The production process according to [5], wherein the solid phase is a dish, a plate, a flask, a bag, a bead, a membrane or a slide glass;
[8] The production process according to any one of [1] to [7], wherein the stem cell is a pluripotent stem cell or a neural stem cell derived from human;
[9] The production process according to [8], wherein the stem cell is an induced pluripotent stem cell;
[10] A recombinant polypeptide comprising in the same molecule:
  (a) a recombinant polypeptide comprising a repeat selected from the group consisting of human fibronectin III-1 to 7, or a recombinant polypeptide comprising an amino acid sequence having substitution, deletion, insertion or addition of one or several amino acids in the amino acid sequence of the repeat selected from the group consisting of the III-1 to 7;
  (b) a recombinant polypeptide comprising human fibronectin III-8 to 10 repeats, or a recombinant polypeptide comprising an amino acid sequence having substitution, deletion, insertion or addition of one or several amino acids in the amino acid sequence of the III-8 to 10 repeats; and
  (c) a recombinant polypeptide comprising human fibronectin III-12 to 14 repeats, or a recombinant polypeptide comprising an amino acid sequence having substitution, deletion, insertion or addition of one or several amino acids in the amino acid sequence of the III-12 to 14 repeats;
[11] The polypeptide according to [10], wherein the recombinant polypeptide (a) is a recombinant polypeptide comprising human fibronectin III-1 to 3 repeats or III-4 to 6 repeats, or a recombinant polypeptide comprising an amino acid sequence having substitution, deletion, insertion or addition of one or several amino acids in the amino acid sequence of the III-1 to 3 repeats or the III-4 to 6 repeats;
[12] The recombinant polypeptide according to [10], which is a recombinant polypeptide comprising an amino acid sequence of SEQ ID NO: 19 or 20, or a recombinant polypeptide comprising an amino acid sequence having substitution, deletion, insertion or addition of one or several amino acids in the amino acid sequence of SEQ ID NO: 19 or 20;
[13] A solid phase coated with the recombinant polypeptide according to any one of to [12];
[14] The solid phase according to [13], which is a device for cell culture or a carrier for cell culture coated with the recombinant polypeptide; and
[15] The solid phase according to [13], which is a dish, a plate, a flask, a bag, a bead, a membrane or a slide glass coated with the recombinant polypeptide.

Effects of the Invention

According to the present invention, a process for producing a stem cell is provided. According to the process of the present invention, it is possible to make stem cells proliferate efficiently, maintain the undifferentiated state of stem cells, and induce stem cells efficiently. The process results in a high cell proliferation rate. The stem cells obtained by the present invention have the ability to differentiate into desired cells, and therefore, for example, they are suitably used for regenerative medicine. Accordingly, the process of the present invention is expected to make a great contribution to the medical field. In addition, according to the present invention, a novel recombinant fibronectin fragment is provided.

BRIEF DESCRIPTION OF DRAWINGS

FIG. 1 is a schematic diagram showing a domain structure of fibronectin.
FIG. 2 is a graph showing cell proliferation in Example 5.
FIG. 3 is a graph showing cell proliferation in Example 6.
FIG. 4 is a graph showing cell proliferation in Example 7.
FIG. 5 is a graph showing cell proliferation in Example 8.
FIG. 6 is a schematic diagram showing domain structures of fibronectin fragments.

MODE FOR CARRYING OUT THE INVENTION

The present invention is described in detail below.
<Fibronectin>
Fibronectin derived from human and mammals has been well studied. The findings mainly on plasma fibronectin derived from human are described below.
Fibronectin is a huge glycoprotein having a molecular weight of about 250 kDa (monomer) present in the blood, cell surface, extracellular matrix and the like. It is known that fibronectin has various functions such as cell adhesion. Fibronectin is composed of a domain structure (see FIG. 1), and its amino acid sequence contains three kinds of similar sequences. The three kinds of similar sequences are called type I repeats, type II repeats, and type III repeats. Among these, a type III repeat is composed of 87 to 96 amino acid residues, and an amino acid sequence homology between the repeats is 17 to 40%. Fifteen type III repeats are present in fibronectin. Among them, the 1st, 2nd, and 3rd repeats (hereinafter referred to as III-1, III-2, and III-3, respectively) are contained in the self-association domain, the 4th, 5th, and 6th repeats (hereinafter referred to as III-4, III-5, and III-6, respectively) are contained in the DNA binding domain, the 8th, 9th, and 10th repeats (hereinafter referred to as III-8, III-9, and III-10, respectively) are contained in the cell binding domain, and the 12th, 13th and 14th repeats (hereinafter referred to as III-12, III-13, and III-14, respectively) are contained in the heparin-binding domain. III-10 contains a region having a binding activity to integrin $\alpha_5\beta_1$ (also referred to as VLA-5), and the core sequence is RGD. In addition, there is a region called IIICS at a position close to the C-terminus of fibronectin. IIICS contains a sequence composed of 25 amino acids called CS-1, and the sequence shows a binding activity to integrin $\alpha_4\beta_1$ (also referred to as VLA-4).
The amino acid sequences of human fibronectin III-1 to 14 and CS-1 are shown as SEQ ID NOs: 1 to 14 and 15, respectively in the Sequence Listing of the present specification.
1. Process for Producing the Stem Cell of the Present Invention
The process for producing the stem cell of the present invention is characterized by comprising the step of culturing a stem cell in the presence of polypeptides which are recombinant fibronectin fragments.
The stem cell used in the present invention is not limited as long as it has the ability to divide to produce the same cell as itself (self-renewal ability) and the ability to differentiate into other types of cells. Stem cells are classified as described below depending on the differentiation ability, but any of the stem cells may be used in the present invention.
  (1) A totipotent stem cell: refers to a stem cell that can differentiate into all types of cells forming an individual, including in vitro tissues such as placenta. Examples thereof include fertilized eggs (and up to 4th to 8th cleavage).
  (2) A pluripotent stem cell: refers to a stem cell that does not form an individual but can differentiate into all cell lineages belonging to the three germ layers (endoderm, mesoderm, and ectoderm). There is no particular limitation, but examples thereof include an inner cell mass at the blastocyst stage, an embryonic stem cell (ES cell) established from the inner cell mass, an induced pluripotent stem cell (iPS cell), an embryonic tumor cell (EC cell), an embryonic germ cell (EG cell), a nuclear transfer embryonic stem cell (ntES cell), and the like. The pluripotent stem cell is sometimes called a pluripotent cell.

(3) A multipotent stem cell: refers to a stem cell that can differentiate into a variety types of cells, although the differentiable cell lineage is limited. Although not particularly limited, examples thereof include a hematopoietic stem cell, a mesenchymal stem cell, a hepatic stem cell, a pancreatic stem cell, a skin stem cell and the like. Generally, it is not possible to differentiate beyond the germ layer, but there are exceptions.

(4) An oligopotent stem cell: refers to a stem cell that can differentiate only to several cell types. Although not particularly limited, examples thereof include a neural stem cell and the like.

(5) A unipotent stem cell: refers to a stem cell whose differentiable cell type is limited to one type. The unipotent stem cell can divide and proliferate as a stem cell or can differentiate and change to cell types other than stem cells. Although not particularly limited, examples thereof include a muscle stem cell, a germline stem cell (an oogonium, and a spermatogonium) and the like. A unipotent stem cell is sometimes called a precursor cell.

The origin of the stem cell used in the present invention is not particularly limited, and a stem cell derived from any organism, preferably a mammal can be used. The age and sex of the organism are not particularly limited. In one embodiment, a cell derived from a primate (for example, chimpanzee, Japanese monkey, and human) is used. Most preferably, a cell derived from human is used, but the present invention is not limited thereto.

In a suitable aspect of the present invention, the stem cell is preferably a pluripotent stem cell, more preferably an iPS cell, and even more preferably a human iPS cell. Various methods for preparation of iPS cells are known. Use of the process of the present invention is not limited only to use for iPS cells prepared by a specific method. The process of the present invention can also be applied to an established iPS cell, such as an established human iPS cell line (strain 253G1) and the like.

In the case of producing a stem cell by the process of the present invention for the purpose of administration to human, preferably, cells collected from a donor having a histocompatibility antigen type that is the same as or similar to the type of a recipient are subjected to the production of stem cells. For example, cells collected from the recipient himself/herself are subjected to the production of stem cells.

The process for producing the stem cell of the present invention is a process for producing a stem cell characterized by comprising a culturing step in the presence of polypeptides described below (hereinafter sometimes referred to as the culturing step of the present invention).

In the process for producing the stem cell of the present invention, the stem cell is cultured in the presence of the polypeptide (a), the polypeptide (b), and the polypeptide (c). The process of the present invention can be carried out in the presence of the polypeptide (a), the polypeptide (b), and the polypeptide (c). The culturing of the stem cell may be carried out in the presence of a mixture of two kinds of polypeptides, that is, a polypeptide comprising the polypeptide (a) and the polypeptide (b) in the same molecule and the polypeptide (c), in the presence of a mixture of two kinds of polypeptides, that is, the polypeptide (a) and a polypeptide comprising the polypeptide (b) and the polypeptide (c) in the same molecule, in the presence of a mixture of two kinds of polypeptides, that is, a polypeptide comprising the polypeptide (a) and the polypeptide (b) in the same molecule and a polypeptide comprising the polypeptide (b) and the polypeptide (c) in the same molecule, or in the presence of one kind of polypeptide comprising the polypeptide (a), the polypeptide (b) and the polypeptide (c) in the same molecule. However, the above-described one kind of polypeptide comprising the polypeptide (a), the polypeptide (b) and the polypeptide (c) in the same molecule is different from full-length fibronectin.

The polypeptide (a) is a recombinant polypeptide comprising a repeat selected from the group consisting of human fibronectin III-1 to 7 or a recombinant polypeptide comprising an amino acid sequence having substitution, deletion, insertion or addition of one or several amino acids in the amino acid sequence of the repeat selected from the group consisting of the III-1 to 7. In the polypeptide (a), "a repeat selected from the group consisting of human fibronectin III-1 to 7" may be at least one repeat, preferably three repeats, or may be all seven repeats. The polypeptide (a) is particularly preferably a polypeptide comprising III-1, III-2 and III-3 repeats, or a polypeptide comprising III-4, III-5 and III-6 repeats, or a polypeptide comprising an amino acid sequence having substitution, deletion, insertion or addition of one or several amino acids in the amino acid sequence of the III-1 to 3 repeats or the III-4 to 6 repeats.

The polypeptide (b) is a recombinant polypeptide comprising human fibronectin III-8 to 10 repeats or a recombinant polypeptide comprising an amino acid sequence having substitution, deletion, insertion or addition of one or several amino acids in the amino acid sequence of the III-8 to 10 repeats. That is, the polypeptide (b) is a polypeptide comprising all of III-8, III-9 and III-10. The polypeptide (c) is a recombinant polypeptide comprising human fibronectin III-12 to 14 repeats or a recombinant polypeptide comprising an amino acid sequence having substitution, deletion, insertion or addition of one or several amino acids in the amino acid sequence of the III-12 to 14 repeats. That is, the polypeptide (c) is a polypeptide comprising all of III-12, III-13, and III-14.

Examples of the polypeptide comprising the polypeptide (a) and the polypeptide (b) in the same molecule include a 120 kDa fibronectin fragment (120 k-fr). 120 k-fr is a protein having a molecular weight of about 120 kDa which comprises III-1, III-2, III-3, III-4, III-5, III-6, III-7, III-8, III-9 and III-10 from the N-terminal side in order. A predicted amino acid sequence (932 amino acid residues) of 120 k-fr is shown as SEQ ID NO: 16 in the Sequence Listing of the present specification. 120 k-fr can be produced as a recombinant polypeptide by preparing a DNA encoding the amino acid sequence of 120 k-fr and combining it with an appropriate host-vector system. Commercially available 120 k-fr may also be used.

Examples of the polypeptide comprising the polypeptide (b) and the polypeptide (c) in the same molecule include CH-271 and CH-296.

CH-271 is a recombinant protein having a molecular weight of about 60 kDa (549 amino acid residues) which comprises III-8, III-9, III-10, III-12, III-13, and III-14 from the N-terminal side in order. The amino acid sequence of CH-271 is shown as SEQ ID NO: 17 in the Sequence Listing of the present specification.

CH-296 is a recombinant protein having a molecular weight of about 63 kDa (574 amino acid residues) which comprises III-8, III-9, III-10, III-12, III-13, III-14, and CS-1 from the N-terminal side in order. The amino acid sequence of CH-296 is shown as SEQ ID NO: 18 in the Sequence Listing of the present specification. CH-296 is commercially available as RetroNectin (registered trademark, manufactured by TAKARA BIO INC.).

For example, the process for producing the stem cell of the present invention can be carried out by using the 120 k-fr in combination with CH-271 or CH-296.

A polypeptide comprising the polypeptide (a), the polypeptide (b) and the polypeptide (c) in the same molecule can be also used for the process for producing the stem cell of the present invention. Although the present invention is not particularly limited, examples of the polypeptide comprising the polypeptide (a), the polypeptide (b) and the polypeptide (c) in the same molecule include FCH-296 and DCH-296 as described below.

FCH-296 is a recombinant polypeptide having a molecular weight of about 96 kDa (881 amino acid residues) which comprises III-1, III-2, III-3, III-8, III-9, III-10, III-12, III-13, III-14, and CS-1 from the N-terminal side in order. The amino acid sequence of FCH-296 is shown as SEQ ID NO: 19 in the Sequence Listing of the present specification. Amino acids 1 to 298 of SEQ ID NO: 19 correspond to the polypeptide (a), amino acids 299 to 307 of SEQ ID NO: 19 correspond to GS linker, amino acids 308 to 585 of SEQ ID NO: 19 correspond to the polypeptide (b), and amino acids 586 to 856 of SEQ ID NO: 19 correspond to the polypeptide (c), and amino acids 857 to 881 of SEQ ID NO: 19 correspond to CS-1. Meanwhile, amino acids 94 to 111 of SEQ ID NO: 19 form a region other than the type III repeats existing between III-1 and III-2. FCH-296 is a novel polypeptide which was produced for the first time in the present invention.

DCH-296 is a recombinant polypeptide having a molecular weight of about 93 kDa (851 amino acid residues) which comprises III-4, III-5, III-6, III-8, III-9, III-10, III-12, III-13, III-14, and CS-1 from the N-terminal side in order. The amino acid sequence of DCH-296 is shown as SEQ ID NO: 20 in the Sequence Listing of the present specification. Amino acids 1 to 268 of SEQ ID NO: 20 correspond to the polypeptide (a), amino acids 269 to 277 of SEQ ID NO: 20 correspond to GS linker, amino acids 278 to 555 of SEQ ID NO: 20 correspond to the polypeptide (b), amino acids 556 to 826 of SEQ ID NO: 20 correspond to the polypeptide (c), and amino acids 827 to 851 of SEQ ID NO: correspond to CS-1. DCH-296 is a novel polypeptide which was produced for the first time in the present invention.

Each of the polypeptides (a) to (c) used in the present invention may comprise an amino acid sequence having substitution, deletion, insertion or addition of one or several amino acids in the amino acid sequence of a repeat selected from the group consisting of III-1 to 7, the amino acid sequence of III-8 to 10 repeats, or the amino acid sequence of III-12 to 14 repeats, as long as it is functionally equivalent, or retains a function of making stem cells proliferate, a function of maintaining the undifferentiated state of stem cells, or a function of inducing stem cells. In the present specification, "one or several" is, but not particularly limited, in the range of 1 to 15, preferably in the range of 1 to 10, more preferably in the range of 1 to 5, and particularly preferably in the range of 1 to 3. For example, the polypeptide includes, but not particularly limited to, a polypeptide comprising, instead of III-1 (SEQ ID NO: 1), an amino acid sequence having deletion of N-terminal 9 amino acids of III-1 (SEQ ID NO: 23), an amino acid sequence having deletion of N-terminal 5 amino acids of III-1 (SEQ ID NO: 24), or an amino acid sequence having deletion of N-terminal 3 amino acids of III-1 (SEQ ID NO: 25). Further, examples of the polypeptide comprising the polypeptides (a) to (c) include a polypeptide comprising an amino acid sequence having substitution, deletion, insertion or addition of one or several amino acids in the amino acid sequence of FCH-296 (SEQ ID NO: 19) or the amino acid sequence of DCH-296 (SEQ ID NO: 20). More specific examples include, but not limited to, FCH-296 having deletion of N-terminal 9 amino acids (SEQ ID NO: 29), FCH-296 having deletion of N-terminal 6 amino acids (SEQ ID NO: 30), FCH-296 having deletion of N-terminal 5 amino acids (SEQ ID NO: 31), FCH-296 having deletion of N-terminal 3 amino acids (SEQ ID NO: 32), FCH-296 having insertion of N-terminal 3 amino acids (SEQ ID NO: 33), FCH-296 having insertion of N-terminal 6 amino acids (SEQ ID NO: 34), FCH-296 having insertion of N-terminal 9 amino acids (SEQ ID NO: 35), FCH-296 having insertion of N-terminal 11 amino acids (SEQ ID NO: 36), FCH-296 having insertion of N-terminal 12 amino acids (SEQ ID NO: 37), FCH-296 having insertion of N-terminal 14 amino acids (SEQ ID NO: 38), FCH-296 having insertion of N-terminal 15 amino acids (SEQ ID NO: 39), FCH-296 having insertion of N-terminal HKRHEEGH (SEQ ID NO: 40), FCH-296 having insertion of N-terminal HKRH (SEQ ID NO: 41), FCH-296 having insertion of N-terminal HH (SEQ ID NO: 42), FCH-296 having insertion of N-terminal HHH (SEQ ID NO: 43), FCH-296 having N-terminal His-tag (SEQ ID NO: 21), and DCH-296 having N-terminal His-tag (SEQ ID NO: 22).

In addition, each of the polypeptides (a) to (c) used in the present invention may comprise an amino acid sequence having an identity with the amino acid sequence of a repeat selected from the group consisting of III-1 to 7, the amino acid sequence of III-8 to 10 repeats, or the amino acid sequence of III-12 to 14 repeats, as long as it is functionally equivalent, or retains a function of making stem cells proliferate, a function of maintaining the undifferentiated state of stem cells, or a function of inducing stem cells. Examples thereof include, but not particularly limited to, a polypeptide having an amino acid sequence having 80% or more, preferably 90% or more, and particularly preferably 95% or more identity with the amino acid sequence of the repeat selected from the group consisting of III-1 to 7, the amino acid sequence of III-8 to 10 repeats, or the amino acid sequence of III-12 to 14 repeats.

The substitution, deletion, insertion or addition of amino acid(s) (hereinafter sometimes referred to as "amino acid substitution or the like") may be preferably carried out to the extent that can change the physicochemical properties or the like of the polypeptide within a range that can maintain the function of the original polypeptide. For example, amino acid substitution or the like is preferably conservative in a range that does not substantially change the properties (for example, hydrophobicity, hydrophilicity, charge, pK, and the like) possessed by the original polypeptide. For example, the amino acid substitution is a substitution within each group of: 1. glycine, and alanine; 2. valine, isoleucine, and leucine; 3. aspartic acid, glutamic acid, asparagine, and glutamine; 4. serine, and threonine; 5. lysine, and arginine; and 6. phenylalanine, and tyrosine. The amino acid deletion, addition, or insertion is preferably deletion, addition, or insertion of amino acid(s) having similar properties to the properties around the target site in the polypeptide, within the range that does not substantially change the properties around the target site.

The amino acid substitution or the like may be naturally occurring due to species difference or individual difference, or may be artificially introduced. The artificial introduction may be carried out by a known method, and there is no particular limitation. For example, a nucleic acid obtained by introducing substitution, deletion, addition or insertion of base(s) into a nucleic acid encoding the above-described polypeptide by a known method may be used. By using the nucleic acid, a polypeptide having an amino acid sequence having one or several amino acid substitution or the like in the amino acid sequence of the above-described polypeptide can be produced.

In the present specification, the term "functionally equivalent" or "an equivalent function" means functionally equivalent or an equivalent function to the corresponding polypeptide into which no amino acid substitution or the like has been introduced. That is, it means that when production of stem cells described later is carried out using the polypeptide to be compared, a cell proliferation rate of stem cells which is equivalent to that obtained when the corresponding polypeptide into which no amino acid substitution or the like has been introduced is used is obtained, or an undifferentiated state of stem cells which is equivalent to that of the corresponding polypeptide into which no amino acid substitution or the like has been introduced is used is maintained, or an equivalent induction rate of stem cells is obtained. That is, the function of the polypeptide can be appropriately confirmed by evaluating its properties according to the method described in Examples described later.

The polypeptide used in the present invention may contain peptide(s) or amino acid residue(s) other than the above-described type III repeats and/or region(s) present in fibronectin other than the above-described type III repeats such as CS-1, as long as the polypeptide used in the present invention does not lose its utility in culturing stem cells. For example, any peptide(s) or amino acid residue(s) can be introduced into region(s) other than the above-described type III repeats, and examples thereof include a polypeptide of the present invention into which amino acid residue(s) or peptide(s) is inserted as linker(s) between the repeats and a polypeptide of the present invention to which a peptide (tag) useful for purification of a recombinant polypeptide is added. Examples of the linker include, but not limited to, a glycine-serine linker (GS linker). Examples of the tag include, but not limited to, a polyhistidine-tag (His-tag), a Flag-tag, and a Glutathione S-Transferase tag (GST-tag). Examples of the polypeptide used in the present invention include, but not limited to, FCH-296 polypeptide having a His-tag at the N-terminus (SEQ ID NO: 21) and DCH-296 polypeptide having a His-tag at the N-terminus (SEQ ID NO: 22).

In the culturing step of the present invention, the stem cells are cultured at a high cell proliferation rate while the stem cells maintain the undifferentiated state. As described in Examples described later, the process for producing the stem cell of the present invention is very useful because it has a clearly higher cell proliferation rate and can highly maintain the undifferentiated state as compared with the process using each of 120 k-fr, CH-271 and CH-296 alone which are known fibronectin fragments. Further, when the above process is applied to expansion of stem cells, there is a great advantage that a high cell proliferation rate and maintenance of the undifferentiated state can be realized without using feeder cells.

With regard to the preparation of polypeptides, information on fibronectin can be seen in Kimiduka F., et al., J. Biochem., Vol. 110, pages 284 to 291 (1991), Kornbrihtt A. R., et al., EMBO J., Vol. 4, No. 7, 1755 to 1759 (1985), Sekiguchi K., et al., Biochemistry, Vol. 25, No. 17, 4936 to 4941 (1986) and the like. In addition, the nucleotide sequence encoding fibronectin and the amino acid sequence of fibronectin are disclosed in Genbank Accession Nos. NM_002026 and NP_002017.

The polypeptide used in the present invention is produced by recombinant DNA technology. From the viewpoint of production or handling of a recombinant, the molecular weight of the polypeptide used in the present invention is preferably 100 kDa or less. The polypeptide in the present specification also encompasses a chemically modified polypeptide such as an acetylated polypeptide.

In a suitable aspect of the present invention, the culturing of the stem cell is carried out in a state where a solid phase coated with the polypeptides is contact with the stem cell. Examples of the above-described solid phase include a container or a carrier (a microbead and the like) used for cell culture. The above-described solid phase coated with the polypeptides has the ability to retain stem cells stably and is useful for culturing the cells. The culture container may be of made of any material as long as it does not inhibit cell maintenance, survival, differentiation, maturation and self-renewal, and may have any shape as long as it does not inhibit cell maintenance, survival, differentiation, maturation and self-replication. Examples of the material for the culture container include glass, a synthetic resin including a nonwoven fabric, a natural resin, a metal and the like. Examples of the shape of the culture container include a polygonal column such as a triangular prism, a cube, and a rectangular parallelepiped, a cylinder, a polygonal pyramid such as a triangular pyramid, and a quadrangular pyramid, a cone, an any shape such as a gourd, a spherical shape, a hemispherical shape, a circular shape, an elliptical shape, a semicircular shape and the like.

Examples of the device for cell culture which can be used for culturing the stem cells include, but not limited to, a dish, a plate, a flask, a bag, a membrane, a slide glass, a large culture tank, a bioreactor, a hollow fiber type culture device and the like. Preferably, a plate is used, and more preferably a Tissue culture treated plate is used.

Examples of the bag which can be used include a $CO_2$ gas permeable bag for cell culture. When a large amount of stem cells is produced industrially, a large culture tank can be used. Culturing can be carried out in either an open system or a closed system, but preferably culturing is carried out in a closed system from the viewpoint of the safety of the obtained stem cells.

Coating of a solid-phase, that is, immobilization of the polypeptides on the solid-phase surface may be carried out by a known method. For example, it is possible to carry out the coating by the same method as the immobilization of fibronectin fragments described in WO 97/18318 A and WO 00/09168 A. When the polypeptides are immobilized on a solid phase, after obtaining the stem cells by the process of the present invention, it is easy to separate the cells and the polypeptides of the present invention merely by separating the cells and the solid phase. Accordingly, contamination of the stem cells with the polypeptides and the like can be prevented.

More specifically, a coating solution is prepared by dissolving the polypeptides in sterilized distilled water, a buffer, a physiological saline or the like, and the coating solution can be used for immobilization. Preferably, a coating solution obtained using a phosphate buffered saline (PBS), particularly preferably Dulbecco's PBS (D-PBS) as a solvent may be used.

The molar concentration of the polypeptide in the coating solution is not particularly limited, but examples thereof include 1 to 100,000 nM, preferably 10 to 2000 nM, and more preferably 30 to 1000 nM. When FCH-296 is used as the polypeptide, the above-described molar concentration is expressed as weight concentration of 0.1 to 1000 μg/mL, preferably 1 to 200 μg/mL, and more preferably 3 to 100 μg/mL.

Coating can be carried out by adding the above-described coating solution to the culture container and keeping it for an appropriate period of time. Conditions for keeping the coating solution may be appropriately determined, but examples of the conditions include a condition at room temperature for 1 hour, or a condition at 4° C. overnight.

The container coated with the fibronectin fragment can be used as it is or can be stored at a low temperature, for example at a temperature of 0 to 10° C. until use. Immediately before use, the coating solution is removed from the culture device, and the culture devise is washed twice with, for example, D-PBS and then once with a cell culture medium if necessary, and then the culture device is subjected to cell culture.

The process for producing the stem cell of the present invention is performed by carrying out the culturing step in the presence of the polypeptides in the whole period or in any part of the period of culturing for producing the stem cell. That is, the present invention encompasses any process including the culturing step as a part of production process of a stem cell.

The culturing step of the present invention includes induction of stem cells, maintenance of stem cells and expansion culture of stem cells, or maintenance of stem cells and expansion culture of stem cells. Accordingly, the present invention provides a process for producing a stem cell comprising inducing, maintaining, and expansion culturing the stem cell in the presence of the above-described recombinant polypeptides (a), (b) and (c), and a process for producing a stem cell comprising maintaining and expansion culturing the stem cell in the presence of the above-described recombinant polypeptides (a), (b) and (c). In the process for producing the stem cell of the present invention, a stem cell useful for regenerative medicine or the like can be produced by carrying out stem cell culturing under appropriately adjusted conditions of the type of cells to be subjected to the process, culture conditions and the like. In the present specification, a stem cell means a cell population containing stem cells.

For the purpose of induction of stem cells, in the culturing step of the present invention, the type of a cell to be used at the start of the culturing and a method for inducing stem cells are not particularly limited. The cell at the start of the culturing may be a differentiated cell (sometimes referred to as a somatic cells) such as a fibroblast, a hepatocyte, an adipocyte, a cardiomyocyte, a hematopoietic cell (a T cell, a B cell, a hematopoietic stem cell and the like), or may be a different type of a stem cell from the induced stem cell. The method for inducing stem cells is not particularly limited as long as it is a known method, and examples thereof include a method comprising contacting a low molecular weight compound with a cell or a method comprising introducing a low molecular weight compound into a cell, a method comprising introducing a reprogramming factor into a cell, a method comprising transplanting a nucleus to a cell, and the like. A reprogramming factor can be introduced into a cell as a protein, or a nucleic acid (RNA, DNA) encoding a reprogramming factor can be introduced into a cell directly or using a vector. Examples of the vector include a retroviral vector, a lentiviral vector, an adenoviral vector, an adeno-associated virus (AAV) vector, a sendai virus vector, a measles virus vector, an episomal vector, and the like.

For the purpose of maintaining and expansion culturing stem cells, the cell concentration at the start of the culture in the culturing step of the present invention is not particularly limited, but it is, for example, 0.005 to $20 \times 10^5$ cells/mL, preferably 0.02 to $5 \times 10^5$ cells/mL, and more preferably 0.05 to $2 \times 10^5$ cells/mL.

Various media used for culturing stem cells can be used in the culturing step of the present invention. When pluripotent stem cells are cultured, for example, Cellartis (registered trademark) DEF-CS medium (manufactured by TAKARA BIO INC.) can be used. Preferable examples include a medium not containing a heterologous component such as a fetal bovine serum (FBS) or a fetal calf serum (FCS) and a sheep serum, a serum-free medium, a medium not containing an unknown component (defined medium) and the like. Such a xeno-free medium free from heterologous components can be appropriately prepared, but a known medium or a commercially available medium may be used as it is or modified. For example, Cellartis (registered trademark) DEF-CS Xeno-Free medium (manufactured by TAKARA BIO INC.), DXF (manufactured by PromoCell GmbH), and TeSR-E8 medium (manufactured by STEMCELL Technologies Inc.) may be used as a commercially available medium containing no heterologous component. When neural stem cells are cultured, for example, RHB-A medium (manufactured by TAKARA BIO INC.) can be used.

Culture conditions for cells are not particularly limited, and ordinary cell culture conditions can be employed. Examples of the culture conditions include a culture condition at a temperature of 37° C., a humidity of 95% and a $CO_2$ concentration of 5%, but the present invention is not limited to such a condition. Examples thereof include a culture condition at a temperature of 30 to 40° C., a humidity of 90 to 98%, and a $CO_2$ concentration of 3 to 7%, but a temperature, a humidity and a $CO_2$ concentration other than the above ranges may be employed as long as a desired cell proliferation can be achieved. During the culturing, it is preferable to dilute a cell culture medium by adding a fresh medium to the cell culture medium at an appropriate time interval, to exchange the medium with a fresh medium, or to change the device for cell culture. The medium to be used, other components to be used at the same time and the like can be appropriately determined.

In a suitable aspect of the present invention, for the purpose of maintaining and expansion culturing stem cells, the stem cells are cultured in an appropriate medium in a container coated with the polypeptides used in the present invention. For example, they are cultured for 5 days or more, preferably for 10 days or more while exchanging the medium and passaging. By this culturing, stem cells can be proliferated. That is, 80% or more, preferably 90% or more of the cell population obtained by the culturing are stem cells.

In a suitable aspect of the present invention, for the purpose of single cell cloning of a stem cell, serially diluted stem cells are seeded in a container coated with the polypeptides used in the present invention. Thereafter, using an appropriate medium, culturing is continued until a colony appears, for example, for 5 days or more, preferably for 10 days or more, while exchanging the medium. Single cell cloning of a stem cell can be performed by obtaining the colony. That is, 80% or more, preferably 90% or more of cells in the colony obtained by the culturing are stem cells.

The stem cell obtained by the culturing step of the present invention can be distinguished from other cells based on the morphological features. In the case of a pluripotent stem cell, the cell can also be confirmed based on the expression of a marker molecule which is an indicator of undifferentiated state such as alkaline phosphatase, a stage-specific embryonic antigen (SSEA) such as SSEA-4, a tumor rejection antigen (TRA) such as TRA-1-60 and TRA-1-81, as well as OCT4 and NANOG. Expression of the above-described molecule (positive marker) can be confirmed, for example, by using an antibody that recognizes the above-described molecule. Regarding alkaline phosphatase, its expression can also be confirmed based on its enzyme activity. On the other hand, in the case of a neural stem cell, though not particularly limited, it can also be confirmed based on the expression of a neural stem cell marker molecule such as Nestin.

80% or more, preferably 90% or more, more preferably 95% or more of the stem cells obtained by the culturing step of the present invention express the positive marker.

Further, stem cells can be isolated from the cell population obtained by the culturing step of the present invention, and thereby stem cells separated from other cells can be obtained. An antibody that recognizes a molecule characteristic of a stem cell is useful for isolating and purifying the stem cell obtained according to the present invention. The stem cell thus isolated can be established as a cell line by a known method. That is, as one aspect of the present invention, a process for producing a stem cell comprising the step of the process for producing a cell population containing the stem cell of the present invention and the step of isolating the stem cell from the obtained cell population can be mentioned. Furthermore, it is also possible to produce various differentiated cells by differentiating the stem cells thus obtained by a known method.

The stem cell obtained by the present invention and the differentiated cell obtained from the stem cell can also be used for, for example, research on stem cell differentiation, drug screening for various diseases, evaluation of efficacy and safety of drug candidate compounds and the like. According to the present invention, many stem cells can be obtained by a single operation. Thus, unlike conventional methods, it is possible to obtain reproducible research results without being influenced by differences between lots of cells.

2. Polypeptide of the Present Invention

The present invention provides a novel recombinant polypeptide useful for the production of a stem cell. The polypeptide is a recombinant polypeptide comprising the polypeptides (a) to (c) in the same molecule as described in "1. Process for producing the stem cell of the present invention", and is useful for the process. The polypeptide of the present invention has a function of making stem cells proliferate, a function of maintaining the undifferentiated state of stem cells, and/or a function of inducing stem cells. The polypeptide of the present invention has a function equivalent to full-length fibronectin or a function higher than existing fibronectin fragments.

The polypeptide of the present invention is a recombinant polypeptide comprising the following polypeptides (a) to (c) in the same molecule.

(a) A recombinant polypeptide comprising a repeat selected from the group consisting of human fibronectin III-1 to 7 or a recombinant polypeptide comprising an amino acid sequence having substitution, deletion, insertion or addition of one or several amino acids in the amino acid sequence of the repeat selected from the group consisting of the III-1 to 7;

(b) A recombinant polypeptide comprising human fibronectin III-8 to 10 repeats or a recombinant polypeptide comprising an amino acid sequence having substitution, deletion, insertion or addition of one or several amino acids in the amino acid sequence of the III-8 to 10 repeats; and (c) A recombinant polypeptide comprising human fibronectin III-12 to 14 repeats or a recombinant polypeptide comprising an amino acid sequence having substitution, deletion, insertion or addition of one or several amino acids in the amino acid sequence of the III-12 to 14 repeats.

The above recombinant polypeptides (a), (b) and (c) are as described in "1. Process for producing the stem cell of the present invention".

Examples of the polypeptide of the present invention include, but not limited to, a polypeptide having the polypeptides (a), (b), and (c) from the N-terminal side. It is also preferable that each of the polypeptides (b) and (c) has the binding activity to integrin $\alpha_5\beta_1$ (also referred to as VLA-5) and the binding activity to heparin.

A particularly suitable aspect of the polypeptide of the present invention is a polypeptide comprising the amino acid sequence of SEQ ID NO: 19 or 20 in the Sequence Listing. Further, a recombinant polypeptide which comprises an amino acid sequence having substitution, deletion, insertion or addition of one or several amino acids in the amino acid sequence of SEQ ID NO: 19 or 20 in the Sequence Listing and which has a function equivalent to that of a recombinant polypeptide comprising the amino acid sequence of SEQ ID NO: 19 or 20 or which retains a function of making stem cells proliferate, a function of maintaining the undifferentiated state of stem cells, and/or a function of inducing stem cells is included in the present invention. For example, the polypeptide includes, but not particularly limited to, a polypeptide comprising, instead of III-1 (SEQ ID NO: 1), an amino acid sequence having deletion of N-terminal 9 amino acids of III-1 (SEQ ID NO: 23), an amino acid sequence having deletion of N-terminal 5 amino acids of III-1 (SEQ ID NO: 24), or an amino acid sequence having deletion of N-terminal 3 amino acids of III-1 (SEQ ID NO: 25). More specifically, examples of the polypeptide include FCH-296 having deletion of N-terminal 9 amino acids (SEQ ID NO: 29), FCH-296 having deletion of N-terminal 6 amino acids (SEQ ID NO: 30), FCH-296 having deletion of N-terminal 5 amino acids (SEQ ID NO: 31), FCH-296 having deletion of N-terminal 3 amino acids (SEQ ID NO: 32), FCH-296 having insertion of N-terminal 3 amino acids (SEQ ID NO: 33), FCH-296 having insertion of N-terminal 6 amino acids (SEQ ID NO: 34), FCH-296 having insertion of N-terminal 9 amino acids (SEQ ID NO: 35), FCH-296 having insertion of N-terminal 11 amino acids (SEQ ID NO: 36), FCH-296 having insertion of N-terminal 12 amino acids (SEQ ID NO: 37), FCH-296 having insertion of N-terminal 14 amino acids (SEQ ID NO: 38), FCH-296 having insertion of N-terminal 15 amino acids (SEQ ID NO: 39), FCH-296 having insertion of N-terminal HKRHEEGH (SEQ ID NO: 40), FCH-296 having insertion of N-terminal HKRH (SEQ ID NO: 41), FCH-296 having insertion of N-terminal HH (SEQ ID NO: 42), FCH-296 having insertion of N-terminal HHH (SEQ ID NO: 43), FCH-296 having N-terminal His-tag (SEQ ID NO: 21), and DCH-296 having N-terminal His-tag (SEQ ID NO: 22).

The polypeptide of the present invention can be produced by using a known recombinant DNA technique. Known hosts and vectors can be used. For example, hosts including bacteria (*Escherichia coli*, *Bacillus subtilis* and the like), yeasts, filamentous fungi, insect cells, and animal cells (mammalian cells including human cells, and the like) may be used and vectors compatible with respective hosts may be used. The vector carries a nucleic acid encoding the polypeptide of the present invention. The nucleic acid can be prepared by modifying a natural nucleic acid (for example, DNA encoding human fibronectin) or can be chemically synthesized. The polypeptide of the present invention expressed in a host into which the vector carrying the nucleic acid is introduced, or the polypeptide of the present invention secreted into the culture supernatant of the host can be purified to a desired purity by a known protein purification method.

3. Solid Phase Coated with the Polypeptide of the Present Invention

The present invention provides a solid phase coated with the polypeptide of the present invention. The solid phase is a solid phase as described in "1. Process for producing the stem cell of the present invention" and is useful for the process.

The solid phase of the present invention is a suitable solid phase having the surface on which the polypeptide is immobilized. Examples of the solid phase include a device for cell culture and a carrier for cell culture, specifically, a dish, a plate, a flask, a bag, a bead, a membrane, and a slide glass. These are not particularly limited as long as they can be used for the process for producing the stem cell of the present invention. For immobilization of the polypeptide on the solid phase, the method as described for the process for producing the stem cell of the present invention can be utilized.

Since the solid phase of the present invention can stably maintain the stem cells on the solid phase surface, it is possible to improve the efficiency of culturing operations such as medium exchange. Further, by preparing the solid phase of the present invention beforehand, it becomes possible to carry out the process for producing the stem cell of the present invention immediately.

EXAMPLES

The present invention is described more specifically by the following Examples which the scope of the present invention is not limited to.

Example 1 Preparation of FCH-296

An FCH-296 polypeptide having a His-tag composed of a methionine residue and 6 histidine residues at the N-terminus (SEQ ID NO: 21) was prepared by the following procedure.

DNA encoding the polypeptide was artificially synthesized and incorporated into an expression plasmid. *Escherichia coli* was transformed with the plasmid, and the resulting transformant was cultured under the conditions that allowed the expression of the polypeptide. The microbial cells collected from the culture were disrupted with an ultrasonic crusher (manufactured by KUBOTA Corporation) to obtain a cell-free extract. Using the extract as a starting material, FCH-296 was purified by a series of column chromatography of Ni-Chelating Sepharose (manufactured by GE Healthcare), Hydroxyapatite (40 µm, manufactured by Bio-Rad Laboratories, Inc.) and SP-Sepharose (manufactured by GE Healthcare). Confirmation of FCH-296 in the purification process was carried out by SDS-PAGE/CBB staining. The buffer of the obtained sample was replaced with a buffer [0.2 g/L KCl, 0.2 g/L $KH_2PO_4$, 8 g/L NaCl, 1.15 g/L $Na_2HPO_4$] to obtain 6 mL of an FCH-296 sample. The FCH-296 sample showed a single band with SDS-PAGE/CBB staining. The protein concentration of the FCH-296 sample was 1.21 mg/mL (12.4 µM calculated from the molecular weight), as measured by using a BCA protein quantification kit (manufactured by Pierce).

Example 2 Preparation of DCH-296

A DCH-296 polypeptide having a His-tag composed of a methionine residue and 6 histidine residues at the N-terminus (SEQ ID NO: 22) was prepared by the following procedure.

DNA encoding the polypeptide was artificially synthesized and incorporated into an expression plasmid. *Escherichia coli* was transformed with the plasmid, and the resulting transformant was cultured under the conditions that allowed the expression of the polypeptide. The microbial cells collected from the culture were disrupted with an ultrasonic crusher to obtain a cell-free extract. Using the extract as a starting material, DCH-296 was purified by a series of column chromatography of Ni-Chelating Sepharose, Hydroxyapatite, and SP-Sepharose. Confirmation of DCH-296 in the purification process was carried out by SDS-PAGE/CBB staining. The buffer of the obtained sample was replaced with a buffer [0.2 g/L KCl, 0.2 g/L $KH_2PO_4$, 8 g/L NaCl, 1.15 g/L $Na_2HPO_4$] to obtain 3 mL of a DCH-296 sample.

The DCH-296 sample showed a single band with SDS-PAGE/CBB staining. The protein concentration of the DCH-296 sample was 1.03 mg/mL (11.0 µM calculated from the molecular weight), as measured by using a BCA protein quantification kit.

Example 3 Evaluation of Adhesiveness of Various Fibronectin Fragments to Human iPS Cells Each of full-length fibronectin (derived from human plasma; manufactured by Sigma-Aldrich Co. LLC., F0895, final concentration: 50 µg/ml), 120 k-fr (manufactured by Millipore Corporation, F1904, final concentration: 40 µg/ml), CH-271 (J. Biochem., Vol. 110, p. 284-291 (1991), final concentration: 25 µg/ml), and CH-296 (RetroNectin: manufactured by Takara Bio Inc., final concentration: 20 µg/ml) was dissolved in D-PBS (manufactured by PromoCell GmbH, C-40232) to prepare a coating solution. After the coating solution was added to a 12 well Tissue culture treated plate (manufactured by Corning Incorporated, 3513) at 0.4 mL/well, the plate was capped and was left to stand overnight at 4° C. On the next day, the coating solution was removed from the plate, and then the plate was washed twice with 1 mL/well of D-PBS to obtain a plate coated with each polypeptide. For coating with two kinds of fibronectin fragments, after a plate was coated with a first coating solution, a second coating solution was added to the plate at 0.4 mL/well, and then the plate was left to stand overnight at 4° C. and washed in the same manner as the first coating. The prepared plate was capped and stored at 4° C. until use.

Human iPS cells (strain 253G1) (manufactured by Center for iPS Cell Research and Application, Kyoto University) which were subcultured with Cellartis (registered trademark) DEF-CS medium (manufactured by TAKARA BIO INC., Y30010) were seeded on a plate at $8 \times 10^4$ cells/well, and were cultured in the same medium at 37° C., 5% $CO_2$. The medium was exchanged daily from the next day, and the cells were observed on the 6th day after the start of the culturing. Results are shown in Table 1.

TABLE 1

| First coating | Second coating | Cell detachment (None: −, Present: +) |
|---|---|---|
| Fibronectin | None | − |
| 120k-fr | None | + |
| CH-271 | None | + |
| CH-296 | None | + |
| 120k-fr | CH-271 | − |
| 120k-fr | CH-296 | − |

No cell detachment was observed on the plate coated with 120 k-fr/CH-271 and the plate coated with 120 k-fr/CH-296. These results show that combining existing fibronectin fragments can enhance the adhesion of cells to the plate.

Example 4 Evaluation of Adhesiveness of FCH-296 and DCH-296 to Human iPS Cells

Each of full-length fibronectin, 120 k-fr, CH-271, CH-296, FCH-296 and DCH-296 was dissolved in D-PBS to prepare a coating solution. In addition, with regard to CH-296, a high concentration coating solution was prepared. With regard to each of FCH-296 and DCH-296, a low concentration coating solution was also prepared. Coating of 12 well Tissue culture treated plates was carried out using these coating solutions in the same manner as in Example 3.

Human iPS cells (strain 253G1) which was subcultured with DEF-CS medium were seeded on a plate at $8 \times 10^4$ cells/well and were cultured at 37° C., 5% $CO_2$. The medium was exchanged daily from the next day, and the cells were observed on the 5th, 8th, and 11th days after the start of the culturing. Results are shown in Table 2.

TABLE 2

| Coating | Weight concentration (μg/ml) | Molar concentration (nM) | Cell detachment (None: −, Present: +) 5th day | 8th day | 11th day |
|---|---|---|---|---|---|
| Fibronectin | 50 | 200 | − | − | − |
| 120k-fr | 40 | 320 | − | + | + |
| CH-271 | 25 | | − | + | + |
| CH-296 | 20 | | − | + | + |
| FCH-296 | 30 | | − | − | − |
| DCH-296 | 30 | | − | − | + |
| CH-296 | 80 | 1300 | − | + | + |
| FCH-296 | 6.3 | 70 | − | − | − |
| DCH-296 | 6.3 | | − | − | + |

On the 8th day, cell detachment was observed on the plates coated with existing fibronectin fragments (120 k-fr, CH-271, and CH-296). On the other hand, on the plate coated with each of DCH-296 and FCH-296, no cell detachment was observed on the 8th day. In particular, in the case of FCH-296, no cell detachment was observed at all on the 11th day even in wells coated with the low concentration coating solution. These results show that FCH-296 has cell adhesiveness equivalent to that of full-length fibronectin in culturing human iPS cells.

Example 5 Long-Term Culture of Human iPS Cells (DEF-CS Medium)

Each of full-length fibronectin and FCH-296 was dissolved in D-PBS to prepare a coating solution at each concentration. Coating of 24 well Tissue culture treated plates (manufactured by Corning Incorporated) was carried out using these coating solutions in the same manner as in Example 3.

Human iPS cells (strain 253G1) were suspended in DEF-CS medium and then seeded on plates. The medium was exchanged daily from the next day, and the cells were subcultured every 3 to 4 days. Results of cell proliferation are shown in FIG. 2. In addition, on the 35th day after the start of the culturing (10th passage), a TRA-1-60 positive cell rate and an SSEA4 positive cell rate were measured by flow cytometry. Results are shown in Table 3. TRA-1-60 and SSEA4 are markers for pluripotent stem cells.

TABLE 3

| Medium | Coating | Concentration (μg/ml) | TRA-1-60 | SSEA4 |
|---|---|---|---|---|
| DEF-CS | Fibronectin | 50 | 97.6% | 99.6% |
| | FCH-296 | 30 | 96.7% | 99.4% |
| | | 6 | 97.1% | 99.4% |
| | | 3 | 97.6% | 99.7% |

Even on the plates coated with FCH-296, human iPS cells proliferated while retaining the pluripotency just like the plate coated with fibronectin. The above results show that human iPS cells can be cultured for a long time on plates coated with FCH-296.

Example 6 Long-Term Culture of Human iPS Cells (DEF-CS Xeno-Free Medium)

Whether or not human iPS cells can be cultured for a long time on plates coated with FCH-296 even in a medium not containing components derived from animals or human, namely, in a xeno-free medium, was examined.

Each of full-length fibronectin and FCH-296 was dissolved in D-PBS to prepare a coating solution at each concentration. Coating of 24 well Tissue culture treated plates was carried out using these coating solutions in the same manner as in Example 3. Coating was also carried out using Synthemax (registered trademark) II-SC Substrate (manufactured by Corning Incorporated) recommended for DEF-CS Xeno-Free medium (manufactured by Takara Bio Inc.).

Human iPS cells (strain 253G1) were suspended in DEF-CS Xeno-Free medium and then seeded on plates. The medium was exchanged daily from the next day and the cells were subcultured every 3 to 4 days. Results of cell proliferation are shown in FIG. 3. On the 35th day after the start of the culturing (10th passage), a TRA-1-60 positive cell rate and an SSEA4 positive cell rate were measured by flow cytometry. Results are shown in Table 4. TRA-1-60 and SSEA4 are markers for pluripotent stem cells.

TABLE 4

| Medium | Coating | Concentration (μg/ml) | TRA-1-60 | SSEA4 |
|---|---|---|---|---|
| DEF-CS Xeno-Free | Fibronectin | 50 | 95.1% | 96.6% |
| | FCH-296 | 30 | 98.0% | 98.5% |
| | | 6 | 99.1% | 98.6% |
| | Synthemax | 25 | 99.4% | 99.4% |

On the plates coated with FCH-296, human iPS cells proliferated while retaining the pluripotency just like the plate coated with fibronectin or Synthemax. The above results show that human iPS cells can be cultured for a long time on plates coated with FCH-296 even in DEF-CS Xeno-Free medium.

Example 7 Long-Term Culture of Human iPS Cells (TeSR-E8 Medium)

TeSR-E8 medium is a xeno-free medium containing only the minimum 8 elements necessary for maintenance of human iPS/ES cells. Whether or not human iPS cells can be cultured for a long time on a plate coated with FCH-296 even in TeSR-E8 medium was examined.

Each of full-length fibronectin and FCH-296 was dissolved in D-PBS to prepare a coating solution at each concentration. Coating of 24 well Tissue culture treated plates was carried out using these coating solutions in the same manner as in Example 3. Coating was also carried out using Vitronectin XF (manufactured by Corning Incorporated) recommended for TeSR-E8 medium (manufactured by STEMCELL Technologies Inc.).

Human iPS cells (strain 253G1) were suspended in TeSR-E8 medium and then seeded on the plates. The medium was exchanged daily from the next day and the cells were subcultured every 3 to 4 days. Results of cell proliferation are shown in FIG. 4. On the 27th day after the start of the culturing (7th passage), a TRA-1-60 positive cell rate and an SSEA4 positive cell rate were measured by flow cytometry. Results are shown in Table 5. TRA-1-60 and SSEA4 are markers for pluripotent stem cells.

TABLE 5

| Medium | Coating | Concentration (μg/ml) | TRA-1-60 | SSEA4 |
|---|---|---|---|---|
| TeSR-E8 | Fibronectin | 50 | 98.3% | 89.6% |
| | FCH-296 | 30 | 99.6% | 98.4% |
| | Vitronectin | 5 | 97.8% | 92.3% |

On the plate coated with FCH-296, human iPS cells proliferated while retaining the pluripotency just like the plate coated with fibronectin or Vitronectin. The above results show that human iPS cells can be cultured for a long time on plates coated with FCH-296 even in TeSR-E8 medium.

Example 8 Long-Term Culture of Human Neural Stem Cells

Whether or not human neural stem cells can be cultured for a long time on plates coated with FCH-296 was examined.

FCH-296 was dissolved in D-PBS to prepare a 30 μg/ml coating solution. Coating of a 12 well Tissue culture treated plate was carried out using the coating solution in the same manner as in Example 3. Coating was also carried out using Laminin (manufactured by Gibco, 10 μg/ml) recommended for RHB-A medium (manufactured by TAKARA BIO INC.). Human neural stem cells were seeded on the coated plates at 1.5 to 2.0×10$^5$ cells/well and were cultured at 37° C., 5% $CO_2$. The medium was exchanged every two days from the next day and the cells were subcultured every 4 to 8 days. Results of cell proliferation are shown in FIG. 5.

When the expression of Nestin, a neural stem cell marker, was confirmed by immunostaining on the 28th day after the start of the culturing (the 5th passage), the cells retained the expression of Nestin even on the plate coated with FCH-296 just like the plate coated with Laminin. The above results show that human neural stem cells can be cultured for a long time on a plate coated with FCH-296.

Example 9 Single Cell Cloning of Human iPS Cell

Each of full-length fibronectin and FCH-296 was dissolved in D-PBS to prepare a coating solution at each concentration. Coating of 96 well Half area Tissue culture treated plates (manufactured by Corning Incorporated) was carried out using these coating solutions in the same manner as in Example 3.

Human iPS cells (strain 253G1) were suspended in DEF-CS medium and then, seeded on the plates at 1 cell/well. The medium was exchanged every two days form the 2nd day. An appearance rate of colonies obtained on the 10th day is shown in Table 6.

TABLE 6

| Medium | Coating | Concentration (μg/ml) | Colony appearance rate |
|---|---|---|---|
| DEF-CS | Fibronectin | 50 | 25.0% |
| | FCH-296 | 30 | 20.3% |
| | | 6 | 23.4% |

Even on the plates coated with FCH-296, colonies each derived from a single human iPS cell were obtained just like the plate coated with fibronectin. Some colonies were subcultured and expanded. When a TRA-1-60 positive cell rate and an SSEA4 positive cell rate were measured by flow cytometry on the 16th day, they were 90% or more in all of the subcultured and expanded colonies. The above results show that single cell cloning of human iPS cells is possible on plates coated with FCH-296.

Example 10 Evaluation of Adhesiveness to Human iPS Cells (F1CH-296, F2CH-296, and F3CH-296)

In order to investigate which repeat is important among III-1, III-2 and III-3, three kinds of polypeptides (F1CH-296, F2CH-296, and F3CH-296) as shown in FIG. 6 were prepared. That is, F1CH-296 (SEQ ID NO: 26), F2CH-296 (SEQ ID NO: 27) and F3CH-296 (SEQ ID NO: 28) each having a His-tag composed of a methionine residue and 6 histidine residues at the N-terminus were prepared in the same manner as in Example 1.

Each of full-length fibronectin, CH-296, FCH-296, F1CH-296, F2CH-296 and F3CH-296 was dissolved in D-PBS to prepare a coating solution at each concentration. Coating of 24 well Tissue culture treated plates was carried out using these coating solutions in the same manner as in Example 3. Herein, 50 μg/ml fibronectin corresponds to about 200 nM, and each of 20 μg/ml CH-296, 30 μg/ml FCH-296, and 24 μg/ml F1CH-296 corresponds to about 320 nM.

Human iPS cells (strain 253G1) were suspended in DEF-CS medium and then seeded on the plates. The medium was exchanged daily from the next day, and the cells were observed on the 3rd, 6th, 8th, and 10th days after the start of the culturing. Results are shown in Table 7 (no cell detachment: −, presence of cell detachment: +).

TABLE 7

| Coating | Concentration (μg/ml) | 3rd day | 6th day | 8th day | 10th day |
|---|---|---|---|---|---|
| Fibronectin | 50 | − | − | − | − |
| CH-296 | 20 | − | + | + | + |
| FCH-296 | 30 | − | − | − | − |
|  | 6 | − | − | + | + |
|  | 3 | − | + | + | + |
| F1CH-296 | 24 | − | − | + | + |
|  | 4.8 | − | − | + | + |
|  | 2.4 | − | + | + | + |
| F2CH-296 | 24 | − | − | + | + |
|  | 4.8 | − | − | + | + |
|  | 2.4 | − | + | + | + |
| F3CH-296 | 24 | − | − | + | + |
|  | 4.8 | − | − | + | + |
|  | 2.4 | − | + | + | + |

The three polypeptides (F1CH-296, F2CH-296, and F3CH-296) showed similar tendencies. That is, for example, under conditions of 24 μg/ml, cell detachment was observed on the 8th day. In contrast, on the plates coated with CH-296, cell detachment was observed on the 6th day, and on the plate coated with FCH-296, cell detachment was not observed. These results show that the adhesion activity of the three polypeptides (F1CH-296, F2CH-296, and F3CH-296) is higher than that of CH-296 and lower than that of FCH-296. The above results show that the three type III repeats (III-1, III-2, and III-3) have equivalent cell adhesiveness, and that the cell adhesion activity is the highest when all three type III repeats are contained.

Example 11 Evaluation of FCH-296 Having Various N-Terminal Sequences

A variety of FCH-296 having various N-terminal sequences was prepared. That is, FCH-296 having deletion of N-terminal 9 amino acids (SEQ ID NO: 29), FCH-296 having deletion of N-terminal 6 amino acids (SEQ ID NO: 30), FCH-296 having deletion of N-terminal 5 amino acids (SEQ ID NO: 31), FCH-296 having deletion of N-terminal 3 amino acids (SEQ ID NO: 32), FCH-296 (SEQ ID NO: 19), FCH-296 having insertion of N-terminal 3 amino acids (SEQ ID NO: 33), FCH-296 having insertion of N-terminal 6 amino acids (SEQ ID NO: 34), FCH-296 having insertion of N-terminal 9 amino acids (SEQ ID NO: 35), FCH-296 having insertion of N-terminal 11 amino acids (SEQ ID NO: 36), FCH-296 having insertion of N-terminal 12 amino acids (SEQ ID NO: 37), FCH-296 having insertion of N-terminal 14 amino acids (SEQ ID NO: 38), FCH-296 having insertion of N-terminal 15 amino acids (SEQ ID NO: 39), FCH-296 having insertion of N-terminal HKRHEEGH (SEQ ID NO: 40), FCH-296 having insertion of N-terminal HKRH (SEQ ID NO: 41), FCH-296 having insertion of N-terminal HH (SEQ ID NO: 42), and FCH-296 having insertion of N-terminal HHH (SEQ ID NO: 43) were prepared.

Using the above-described FCH-296 having various N-terminal sequences instead of FCH-296 (with His-tag, SEQ ID NO: 21) used in Examples 5 to 9, the experiments described in Examples 5 to 9 are carried out. The FCH-296 having various N-terminal sequences has the same effect as FCH-296.

INDUSTRIAL APPLICABILITY

According to the present invention, a process for producing a large amount of stem cells in a short period of time and a polypeptide for use in the process are provided.

Sequence Listing Free Text
SEQ ID NO:1; Partial region of fibronectin named III-1
SEQ ID NO:2; Partial region of fibronectin named III-2
SEQ ID NO:3; Partial region of fibronectin named III-3
SEQ ID NO:4; Partial region of fibronectin named III-4
SEQ ID NO:5; Partial region of fibronectin named III-5
SEQ ID NO:6; Partial region of fibronectin named III-6
SEQ ID NO:7; Partial region of fibronectin named III-7
SEQ ID NO:8; Partial region of fibronectin named III-8
SEQ ID NO:9; Partial region of fibronectin named III-9
SEQ ID NO:10; Partial region of fibronectin named III-10
SEQ ID NO:11; Partial region of fibronectin named III-11
SEQ ID NO:12; Partial region of fibronectin named III-12
SEQ ID NO:13; Partial region of fibronectin named III-13
SEQ ID NO:14; Partial region of fibronectin named III-14
SEQ ID NO:15; Partial region of fibronectin named CS-1
SEQ ID NO:16; Fibronectin fragment named 120 k-fr
SEQ ID NO:17; Fibronectin fragment named CH-271
SEQ ID NO:18; Fibronectin fragment named CH-296 (RetroNectin)
SEQ ID NO:19; Fibronectin fragment named FCH-296
SEQ ID NO:20; Fibronectin fragment named DCH-296
SEQ ID NO:21; His-tag FCH-296
SEQ ID NO:22; His-tag DCH-296
SEQ ID NO:23; N-terminal 9a.a. deletion of III-1
SEQ ID NO:24; N-terminal 5a.a. deletion of III-1
SEQ ID NO:25; N-terminal 3a.a. deletion of III-1
SEQ ID NO:26; His-tag F1CH-296
SEQ ID NO:27; His-tag F2CH-296
SEQ ID NO:28; His-tag F3CH-296
SEQ ID NO:29; N-terminal 9a.a. deletion of FCH-296
SEQ ID NO:30; N-terminal 6a.a. deletion of FCH-296
SEQ ID NO:31; N-terminal 5a.a. deletion of FCH-296
SEQ ID NO:32; N-terminal 3a.a. deletion of FCH-296
SEQ ID NO:33; N-terminal 3a.a. insertion of FCH-296
SEQ ID NO:34; N-terminal 6a.a. insertion of FCH-296
SEQ ID NO:35; N-terminal 9a.a. insertion of FCH-296
SEQ ID NO:36; N-terminal 11a.a. insertion of FCH-296
SEQ ID NO:37; N-terminal 12a.a. insertion of FCH-296
SEQ ID NO:38; N-terminal 14a.a. insertion of FCH-296
SEQ ID NO:39; N-terminal 15a.a. insertion of FCH-296
SEQ ID NO:40; N-terminal HKRHEEGH insertion of FCH-296
SEQ ID NO:41; N-terminal HKRH insertion of FCH-296
SEQ ID NO:42; N-terminal HH insertion of FCH-296
SEQ ID NO:43; N-terminal HHH insertion of FCH-296

The invention claimed is:

1. A recombinant polypeptide comprising in the same molecule:
   (a) a polypeptide comprising three repeats selected from the group consisting of human fibronectin III-1 to 7 repeats wherein the III-1 to 7 repeats comprise the amino acid sequences of SEQ ID NO: 1, 2, 3, 4, 5, 6, and 7 respectively, or a variant of the polypeptide comprising three repeats selected from the group consisting of human fibronectin III-1 to 7 repeats wherein the III-1 to 7 repeats comprise an amino acid sequence having at least 90% identity to the amino acid sequence of SEQ ID NO: 1, 2, 3, 4, 5, 6, and 7 respectively;
   (b) a polypeptide comprising human fibronectin III-8 to 10 repeats comprising the amino acid sequences of SEQ ID NO: 8, 9 and 10 respectively, or a variant of the polypeptide comprising human fibronectin III-8 to 10 repeats comprising an amino acid sequence having at least 90% identity to the amino acid sequence of SEQ ID NO: 8, 9 and 10 respectively; and
   (c) a polypeptide comprising human fibronectin III-12 to 14 repeats comprising the amino acid sequences of SEQ ID NO: 12, 13 and 14 respectively, or a variant of the polypeptide comprising human fibronectin III-12 to 14 repeats comprising an amino acid sequence having at least 90% identity to the amino acid sequence of SEQ ID NO: 12, 13 and 14 respectively;

wherein the recombinant polypeptide retains a function of maintaining an undifferentiated state of stem cells, and wherein the molecular weight of the recombinant polypeptide is 100 kDa or less.

2. The recombinant polypeptide according to claim 1, wherein the polypeptide of (a) is a polypeptide comprising human fibronectin III-1 to 3 repeats comprising the amino acid sequences of SEQ ID NO: 1, 2 and 3 respectively or a polypeptide comprising human fibronectin III-4 to 6 repeats comprising the amino acid sequences of SEQ ID NO: 4, 5 and 6 respectively, or the variant of (a) is a variant of the polypeptide comprising human fibronectin III-1 to 3 repeats comprising an amino acid sequence having at least 90% identity to the amino acid sequence of SEQ ID NO: 1, 2 and 3 respectively or a variant of the polypeptide comprising human fibronectin III-4 to 6 repeats comprising an amino acid sequence having at least 90% identity to the amino acid sequence of SEQ ID NO: 4, 5 and 6 respectively.

3. The recombinant polypeptide according to claim 1, which comprises an amino acid sequence of SEQ ID NO: 19 or 20 or an amino acid sequence having at least 90% identity to the amino acid sequence of SEQ ID NO: 19 or 20, wherein the molecular weight of the recombinant polypeptide is 100 kDa or less.

4. A solid phase coated with the recombinant polypeptide according to claim 1.

5. The solid phase according to claim 4, which is a device for cell culture or a carrier for cell culture coated with the recombinant polypeptide.

6. The solid phase according to claim 4, which is a dish, a plate, a flask, a bag, a bead, a membrane or a slide glass coated with the recombinant polypeptide.

* * * * *

SEQUENCE LISTING

```
<160> NUMBER OF SEQ ID NOS: 43

<210> SEQ ID NO 1
<211> LENGTH: 92
<212> TYPE: PRT
```

<213> ORGANISM: Homo sapiens

<400> SEQUENCE: 1

Ser Gly Pro Val Glu Val Phe Ile Thr Glu Thr Pro Ser Gln Pro Asn
1               5                   10                  15

Ser His Pro Ile Gln Trp Asn Ala Pro Gln Pro Ser His Ile Ser Lys
            20                  25                  30

Tyr Ile Leu Arg Trp Arg Pro Lys Asn Ser Val Gly Arg Trp Lys Glu
        35                  40                  45

Ala Thr Ile Pro Gly His Leu Asn Ser Tyr Thr Ile Lys Gly Leu Lys
    50                  55                  60

Pro Gly Val Val Tyr Glu Gly Gln Leu Ile Ser Ile Gln Gln Tyr Gly
65                  70                  75                  80

His Gln Glu Val Thr Arg Phe Asp Phe Thr Thr Thr
                85                  90

<210> SEQ ID NO 2
<211> LENGTH: 91
<212> TYPE: PRT
<213> ORGANISM: Homo sapiens

<400> SEQUENCE: 2

Ser Pro Leu Val Ala Thr Ser Glu Ser Val Thr Glu Ile Thr Ala Ser
1               5                   10                  15

Ser Phe Val Val Ser Trp Val Ser Ala Ser Asp Thr Val Ser Gly Phe
            20                  25                  30

Arg Val Glu Tyr Glu Leu Ser Glu Glu Gly Asp Glu Pro Gln Tyr Leu
        35                  40                  45

Asp Leu Pro Ser Thr Ala Thr Ser Val Asn Ile Pro Asp Leu Leu Pro
    50                  55                  60

Gly Arg Lys Tyr Ile Val Asn Val Tyr Gln Ile Ser Glu Asp Gly Glu
65                  70                  75                  80

Gln Ser Leu Ile Leu Ser Thr Ser Gln Thr Thr
                85                  90

<210> SEQ ID NO 3
<211> LENGTH: 96
<212> TYPE: PRT
<213> ORGANISM: Homo sapiens

<400> SEQUENCE: 3

Ala Pro Asp Ala Pro Asp Pro Thr Val Asp Gln Val Asp Asp Thr
1               5                   10                  15

Ser Ile Val Val Arg Trp Ser Arg Pro Gln Ala Pro Ile Thr Gly Tyr
            20                  25                  30

Arg Ile Val Tyr Ser Pro Ser Val Glu Gly Ser Ser Thr Glu Leu Asn
        35                  40                  45

Leu Pro Glu Thr Ala Asn Ser Val Thr Leu Ser Asp Leu Gln Pro Gly
    50                  55                  60

Val Gln Tyr Asn Ile Thr Ile Tyr Ala Val Glu Glu Asn Gln Glu Ser
65                  70                  75                  80

Thr Pro Val Val Ile Gln Gln Glu Thr Thr Gly Thr Pro Arg Ser Asp
                85                  90                  95

<210> SEQ ID NO 4
<211> LENGTH: 90
<212> TYPE: PRT
<213> ORGANISM: Homo sapiens

<400> SEQUENCE: 4

Thr Val Pro Ser Pro Arg Asp Leu Gln Phe Val Glu Val Thr Asp Val
1               5                   10                  15

Lys Val Thr Ile Met Trp Thr Pro Pro Glu Ser Ala Val Thr Gly Tyr
            20                  25                  30

Arg Val Asp Val Ile Pro Val Asn Leu Pro Gly Glu His Gly Gln Arg
        35                  40                  45

Leu Pro Ile Ser Arg Asn Thr Phe Ala Glu Val Thr Gly Leu Ser Pro
    50                  55                  60

Gly Val Thr Tyr Tyr Phe Lys Val Phe Ala Val Ser His Gly Arg Glu
65                  70                  75                  80

Ser Lys Pro Leu Thr Ala Gln Gln Thr Thr
                85                  90

<210> SEQ ID NO 5
<211> LENGTH: 90
<212> TYPE: PRT
<213> ORGANISM: Homo sapiens

<400> SEQUENCE: 5

Lys Leu Asp Ala Pro Thr Asn Leu Gln Phe Val Asn Glu Thr Asp Ser
1               5                   10                  15

Thr Val Leu Val Arg Trp Thr Pro Pro Arg Ala Gln Ile Thr Gly Tyr
            20                  25                  30

Arg Leu Thr Val Gly Leu Thr Arg Arg Gly Gln Pro Arg Gln Tyr Asn
        35                  40                  45

Val Gly Pro Ser Val Ser Lys Tyr Pro Leu Arg Asn Leu Gln Pro Ala
    50                  55                  60

Ser Glu Tyr Thr Val Ser Leu Val Ala Ile Lys Gly Asn Gln Glu Ser
65                  70                  75                  80

Pro Lys Ala Thr Gly Val Phe Thr Thr Leu
                85                  90

<210> SEQ ID NO 6
<211> LENGTH: 87
<212> TYPE: PRT
<213> ORGANISM: Homo sapiens

<400> SEQUENCE: 6

Gln Pro Gly Ser Ser Ile Pro Pro Tyr Asn Thr Glu Val Thr Glu Thr
1               5                   10                  15

Thr Ile Val Ile Thr Trp Thr Pro Ala Pro Arg Ile Gly Phe Lys Leu
            20                  25                  30

Gly Val Arg Pro Ser Gln Gly Gly Glu Ala Pro Arg Glu Val Thr Ser
        35                  40                  45

Asp Ser Gly Ser Ile Val Val Ser Gly Leu Thr Pro Gly Val Glu Tyr
    50                  55                  60

Val Tyr Thr Ile Gln Val Leu Arg Asp Gly Gln Glu Arg Asp Ala Pro
65                  70                  75                  80

Ile Val Asn Lys Val Val Thr
                85

<210> SEQ ID NO 7
<211> LENGTH: 93
<212> TYPE: PRT
<213> ORGANISM: Homo sapiens

```
<400> SEQUENCE: 7

Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Gly Tyr Arg Ile Thr Thr Thr Pro Thr Asn Gly Gln Gln Gly Asn Ser
        35                  40                  45

Leu Glu Glu Val Val His Ala Asp Gln Ser Ser Cys Thr Phe Asp Asn
50                  55                  60

Leu Ser Pro Gly Leu Glu Tyr Asn Val Ser Val Tyr Thr Val Lys Asp
65                  70                  75                  80

Asp Lys Glu Ser Val Pro Ile Ser Asp Thr Ile Ile Pro
                85                  90

<210> SEQ ID NO 8
<211> LENGTH: 87
<212> TYPE: PRT
<213> ORGANISM: Homo sapiens

<400> SEQUENCE: 8

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
        35                  40                  45

Pro Ser Asp Asn Ala Val Val Leu Thr Asn Leu Leu Pro Gly Thr Glu
50                  55                  60

Tyr Val Val Ser Val Ser Ser Val Tyr Glu Gln His Glu Ser Thr Pro
65                  70                  75                  80

Leu Arg Gly Arg Gln Lys Thr
                85

<210> SEQ ID NO 9
<211> LENGTH: 90
<212> TYPE: PRT
<213> ORGANISM: Homo sapiens

<400> SEQUENCE: 9

Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
            20                  25                  30

Arg Ile Arg His His Pro Glu His Phe Ser Gly Arg Pro Arg Glu Asp
        35                  40                  45

Arg Val Pro His Ser Arg Asn Ser Ile Thr Leu Thr Asn Leu Thr Pro
50                  55                  60

Gly Thr Glu Tyr Val Val Ser Ile Val Ala Leu Asn Gly Arg Glu Glu
65                  70                  75                  80

Ser Pro Leu Leu Ile Gly Gln Gln Ser Thr
                85                  90

<210> SEQ ID NO 10
<211> LENGTH: 94
<212> TYPE: PRT
<213> ORGANISM: Homo sapiens

<400> SEQUENCE: 10
```

Val Ser Asp Val Pro Arg Asp Leu Glu Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65              70                  75                  80

Ser Pro Ala Ser Ser Lys Pro Ile Ser Ile Asn Tyr Arg Thr
            85                  90

<210> SEQ ID NO 11
<211> LENGTH: 90
<212> TYPE: PRT
<213> ORGANISM: Homo sapiens

<400> SEQUENCE: 11

Glu Ile Asp Lys Pro Ser Gln Met Gln Val Thr Asp Val Gln Asp Asn
1               5                   10                  15

Ser Ile Ser Val Lys Trp Leu Pro Ser Ser Pro Val Thr Gly Tyr
            20                  25                  30

Arg Val Thr Thr Thr Pro Lys Asn Gly Pro Gly Pro Thr Lys Thr Lys
        35                  40                  45

Thr Ala Gly Pro Asp Gln Thr Glu Met Thr Ile Glu Gly Leu Gln Pro
    50                  55                  60

Thr Val Glu Tyr Val Val Ser Val Tyr Ala Gln Asn Pro Ser Gly Glu
65              70                  75                  80

Ser Gln Pro Leu Val Gln Thr Ala Val Thr
            85                  90

<210> SEQ ID NO 12
<211> LENGTH: 92
<212> TYPE: PRT
<213> ORGANISM: Homo sapiens

<400> SEQUENCE: 12

Ala Ile Pro Ala Pro Thr Asp Leu Lys Phe Thr Gln Val Thr Pro Thr
1               5                   10                  15

Ser Leu Ser Ala Gln Trp Thr Pro Pro Asn Val Gln Leu Thr Gly Tyr
            20                  25                  30

Arg Val Arg Val Thr Pro Lys Glu Lys Thr Gly Pro Met Lys Glu Ile
        35                  40                  45

Asn Leu Ala Pro Asp Ser Ser Ser Val Val Val Ser Gly Leu Met Val
    50                  55                  60

Ala Thr Lys Tyr Glu Val Ser Val Tyr Ala Leu Lys Asp Thr Leu Thr
65              70                  75                  80

Ser Arg Pro Ala Gln Gly Val Val Thr Thr Leu Glu
            85                  90

<210> SEQ ID NO 13
<211> LENGTH: 89
<212> TYPE: PRT
<213> ORGANISM: Homo sapiens

<400> SEQUENCE: 13

-continued

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

Gln Val Asp Ala Val Pro Ala Asn Gly Gln Thr Pro Ile Gln Arg Thr
        35                  40                  45

Ile Lys Pro Asp Val Arg Ser Tyr Thr Ile Thr Gly Leu Gln Pro Gly
    50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 14
<211> LENGTH: 90
<212> TYPE: PRT
<213> ORGANISM: Homo sapiens

<400> SEQUENCE: 14

Ala Ile Asp Ala Pro Ser Asn Leu Arg Phe Leu Ala Thr Thr Pro Asn
1               5                   10                  15

Ser Leu Leu Val Ser Trp Gln Pro Pro Arg Ala Arg Ile Thr Gly Tyr
            20                  25                  30

Ile Ile Lys Tyr Glu Lys Pro Gly Ser Pro Pro Arg Glu Val Val Pro
        35                  40                  45

Arg Pro Arg Pro Gly Val Thr Glu Ala Thr Ile Thr Gly Leu Glu Pro
    50                  55                  60

Gly Thr Glu Tyr Thr Ile Tyr Val Ile Ala Leu Lys Asn Asn Gln Lys
65                  70                  75                  80

Ser Glu Pro Leu Ile Gly Arg Lys Lys Thr
                85                  90

<210> SEQ ID NO 15
<211> LENGTH: 25
<212> TYPE: PRT
<213> ORGANISM: Homo sapiens

<400> SEQUENCE: 15

Asp Glu Leu Pro Gln Leu Val Thr Leu Pro His Pro Asn Leu His Gly
1               5                   10                  15

Pro Glu Ile Leu Asp Val Pro Ser Thr
            20                  25

<210> SEQ ID NO 16
<211> LENGTH: 932
<212> TYPE: PRT
<213> ORGANISM: Artificial Sequence
<220> FEATURE:
<223> OTHER INFORMATION: Fibronectin fragment named 120k-fr

<400> SEQUENCE: 16

Ser Gly Pro Val Glu Val Phe Ile Thr Glu Thr Pro Ser Gln Pro Asn
1               5                   10                  15

Ser His Pro Ile Gln Trp Asn Ala Pro Gln Pro Ser His Ile Ser Lys
            20                  25                  30

Tyr Ile Leu Arg Trp Arg Pro Lys Asn Ser Val Gly Arg Trp Lys Glu
        35                  40                  45

Ala Thr Ile Pro Gly His Leu Asn Ser Tyr Thr Ile Lys Gly Leu Lys
    50                  55                  60

```
Pro Gly Val Val Tyr Glu Gly Gln Leu Ile Ser Ile Gln Gln Tyr Gly
 65                  70                  75                  80

His Gln Glu Val Thr Arg Phe Asp Phe Thr Thr Ser Thr Ser Thr
                 85                  90                  95

Pro Val Thr Ser Asn Thr Val Thr Gly Glu Thr Thr Pro Phe Ser Pro
                100                 105                 110

Leu Val Ala Thr Ser Glu Ser Val Thr Glu Ile Thr Ala Ser Ser Phe
                115                 120                 125

Val Val Ser Trp Val Ser Ala Ser Asp Thr Val Ser Gly Phe Arg Val
                130                 135                 140

Glu Tyr Glu Leu Ser Glu Glu Gly Asp Glu Pro Gln Tyr Leu Asp Leu
145                 150                 155                 160

Pro Ser Thr Ala Thr Ser Val Asn Ile Pro Asp Leu Leu Pro Gly Arg
                165                 170                 175

Lys Tyr Ile Val Asn Val Tyr Gln Ile Ser Glu Asp Gly Glu Gln Ser
                180                 185                 190

Leu Ile Leu Ser Thr Ser Gln Thr Thr Ala Pro Asp Ala Pro Pro Asp
                195                 200                 205

Pro Thr Val Asp Gln Val Asp Asp Thr Ser Ile Val Val Arg Trp Ser
210                 215                 220

Arg Pro Gln Ala Pro Ile Thr Gly Tyr Arg Ile Val Tyr Ser Pro Ser
225                 230                 235                 240

Val Glu Gly Ser Ser Thr Glu Leu Asn Leu Pro Glu Thr Ala Asn Ser
                245                 250                 255

Val Thr Leu Ser Asp Leu Gln Pro Gly Val Gln Tyr Asn Ile Thr Ile
                260                 265                 270

Tyr Ala Val Glu Glu Asn Gln Glu Ser Thr Pro Val Val Ile Gln Gln
                275                 280                 285

Glu Thr Thr Gly Thr Pro Arg Ser Asp Thr Val Pro Ser Pro Arg Asp
                290                 295                 300

Leu Gln Phe Val Glu Val Thr Asp Val Lys Val Thr Ile Met Trp Thr
305                 310                 315                 320

Pro Pro Glu Ser Ala Val Thr Gly Tyr Arg Val Asp Val Ile Pro Val
                325                 330                 335

Asn Leu Pro Gly Glu His Gly Gln Arg Leu Pro Ile Ser Arg Asn Thr
                340                 345                 350

Phe Ala Glu Val Thr Gly Leu Ser Pro Gly Val Thr Tyr Tyr Phe Lys
                355                 360                 365

Val Phe Ala Val Ser His Gly Arg Glu Ser Lys Pro Leu Thr Ala Gln
                370                 375                 380

Gln Thr Thr Lys Leu Asp Ala Pro Thr Asn Leu Gln Phe Val Asn Glu
385                 390                 395                 400

Thr Asp Ser Thr Val Leu Val Arg Trp Thr Pro Pro Arg Ala Gln Ile
                405                 410                 415

Thr Gly Tyr Arg Leu Thr Val Gly Leu Thr Arg Arg Gly Gln Pro Arg
                420                 425                 430

Gln Tyr Asn Val Gly Pro Ser Val Ser Lys Tyr Pro Leu Arg Asn Leu
                435                 440                 445

Gln Pro Ala Ser Glu Tyr Thr Val Ser Leu Val Ala Ile Lys Gly Asn
                450                 455                 460

Gln Glu Ser Pro Lys Ala Thr Gly Val Phe Thr Thr Leu Gln Pro Gly
465                 470                 475                 480
```

-continued

```
Ser Ser Ile Pro Pro Tyr Asn Thr Glu Val Thr Glu Thr Thr Ile Val
            485                 490                 495

Ile Thr Trp Thr Pro Ala Pro Arg Ile Gly Phe Lys Leu Gly Val Arg
            500                 505                 510

Pro Ser Gln Gly Gly Glu Ala Pro Arg Glu Val Thr Ser Asp Ser Gly
            515                 520                 525

Ser Ile Val Val Ser Gly Leu Thr Pro Gly Val Glu Tyr Val Tyr Thr
            530                 535                 540

Ile Gln Val Leu Arg Asp Gly Gln Glu Arg Asp Ala Pro Ile Val Asn
545                 550                 555                 560

Lys Val Val Thr Pro Leu Ser Pro Pro Thr Asn Leu His Leu Glu Ala
            565                 570                 575

Asn Pro Asp Thr Gly Val Leu Thr Val Ser Trp Glu Arg Ser Thr Thr
            580                 585                 590

Pro Asp Ile Thr Gly Tyr Arg Ile Thr Thr Thr Pro Thr Asn Gly Gln
            595                 600                 605

Gln Gly Asn Ser Leu Glu Glu Val Val His Ala Asp Gln Ser Ser Cys
            610                 615                 620

Thr Phe Asp Asn Leu Ser Pro Gly Leu Glu Tyr Asn Val Ser Val Tyr
625                 630                 635                 640

Thr Val Lys Asp Asp Lys Glu Ser Val Pro Ile Ser Asp Thr Ile Ile
            645                 650                 655

Pro Ala Val Pro Pro Thr Asp Leu Arg Phe Thr Asn Ile Gly Pro
            660                 665                 670

Asp Thr Met Arg Val Thr Trp Ala Pro Pro Ser Ile Asp Leu Thr
            675                 680                 685

Asn Phe Leu Val Arg Tyr Ser Pro Val Lys Asn Glu Glu Asp Val Ala
            690                 695                 700

Glu Leu Ser Ile Ser Pro Ser Asp Asn Ala Val Val Leu Thr Asn Leu
705                 710                 715                 720

Leu Pro Gly Thr Glu Tyr Val Val Ser Val Ser Ser Val Tyr Glu Gln
            725                 730                 735

His Glu Ser Thr Pro Leu Arg Gly Arg Gln Lys Thr Gly Leu Asp Ser
            740                 745                 750

Pro Thr Gly Ile Asp Phe Ser Asp Ile Thr Ala Asn Ser Phe Thr Val
            755                 760                 765

His Trp Ile Ala Pro Arg Ala Thr Ile Thr Gly Tyr Arg Ile Arg His
            770                 775                 780

His Pro Glu His Phe Ser Gly Arg Pro Arg Glu Asp Arg Val Pro His
785                 790                 795                 800

Ser Arg Asn Ser Ile Thr Leu Thr Asn Leu Thr Pro Gly Thr Glu Tyr
            805                 810                 815

Val Val Ser Ile Val Ala Leu Asn Gly Arg Glu Glu Ser Pro Leu Leu
            820                 825                 830

Ile Gly Gln Gln Ser Thr Val Ser Asp Val Pro Arg Asp Leu Glu Val
            835                 840                 845

Val Ala Ala Thr Pro Thr Ser Leu Leu Ile Ser Trp Asp Ala Pro Ala
            850                 855                 860

Val Thr Val Arg Tyr Tyr Arg Ile Thr Tyr Gly Glu Thr Gly Gly Asn
865                 870                 875                 880

Ser Pro Val Gln Glu Phe Thr Val Pro Gly Ser Lys Ser Thr Ala Thr
            885                 890                 895

Ile Ser Gly Leu Lys Pro Gly Val Asp Tyr Thr Ile Thr Val Tyr Ala
```

```
                    900             905             910
Val Thr Gly Arg Gly Asp Ser Pro Ala Ser Ser Lys Pro Ile Ser Ile
            915             920             925

Asn Tyr Arg Thr
        930

<210> SEQ ID NO 17
<211> LENGTH: 549
<212> TYPE: PRT
<213> ORGANISM: Artificial Sequence
<220> FEATURE:
<223> OTHER INFORMATION: Fibronectin fragment named CH-271

<400> SEQUENCE: 17

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
        35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
        115                 120                 125

Ser Gly Arg Pro Arg Glu Asp Arg Val Pro His Ser Arg Asn Ser Ile
    130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
        195                 200                 205

Tyr Arg Ile Thr Tyr Gly Glu Thr Gly Gly Asn Ser Pro Val Gln Glu
    210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp Lys Pro Ser Met Ala Ile Pro Ala Pro Thr Asp Leu Lys Phe
        275                 280                 285

Thr Gln Val Thr Pro Thr Ser Leu Ser Ala Gln Trp Thr Pro Pro Asn
    290                 295                 300

Val Gln Leu Thr Gly Tyr Arg Val Arg Val Thr Pro Lys Glu Lys Thr
305                 310                 315                 320

Gly Pro Met Lys Glu Ile Asn Leu Ala Pro Asp Ser Ser Ser Val Val
```

```
            325                 330                 335
Val Ser Gly Leu Met Val Ala Thr Lys Tyr Glu Val Ser Val Tyr Ala
            340                 345                 350

Leu Lys Asp Thr Leu Thr Ser Arg Pro Ala Gln Gly Val Val Thr Thr
        355                 360                 365

Leu Glu Asn Val Ser Pro Pro Arg Arg Ala Arg Val Thr Asp Ala Thr
    370                 375                 380

Glu Thr Thr Ile Thr Ile Ser Trp Arg Thr Lys Thr Glu Thr Ile Thr
385                 390                 395                 400

Gly Phe Gln Val Asp Ala Val Pro Ala Asn Gly Gln Thr Pro Ile Gln
                405                 410                 415

Arg Thr Ile Lys Pro Asp Val Arg Ser Tyr Thr Ile Thr Gly Leu Gln
            420                 425                 430

Pro Gly Thr Asp Tyr Lys Ile Tyr Leu Tyr Thr Leu Asn Asp Asn Ala
        435                 440                 445

Arg Ser Ser Pro Val Val Ile Asp Ala Ser Thr Ala Ile Asp Ala Pro
    450                 455                 460

Ser Asn Leu Arg Phe Leu Ala Thr Thr Pro Asn Ser Leu Leu Val Ser
465                 470                 475                 480

Trp Gln Pro Pro Arg Ala Arg Ile Thr Gly Tyr Ile Ile Lys Tyr Glu
                485                 490                 495

Lys Pro Gly Ser Pro Arg Glu Val Val Pro Arg Pro Arg Pro Gly
            500                 505                 510

Val Thr Glu Ala Thr Ile Thr Gly Leu Glu Pro Gly Thr Glu Tyr Thr
        515                 520                 525

Ile Tyr Val Ile Ala Leu Lys Asn Asn Gln Lys Ser Glu Pro Leu Ile
    530                 535                 540

Gly Arg Lys Lys Thr
545

<210> SEQ ID NO 18
<211> LENGTH: 574
<212> TYPE: PRT
<213> ORGANISM: Artificial Sequence
<220> FEATURE:
<223> OTHER INFORMATION: Fibronectin fragment named CH-296 (RetroNectin)

<400> SEQUENCE: 18

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
        35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
        115                 120                 125

Ser Gly Arg Pro Arg Glu Asp Arg Val Pro His Ser Arg Asn Ser Ile
```

-continued

```
            130                 135                 140
Thr Leu Thr Asn Leu Thr Pro Gly Thr Glu Tyr Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
                180                 185                 190

Thr Ser Leu Leu Ile Ser Trp Asp Ala Pro Ala Val Thr Val Arg Tyr
            195                 200                 205

Tyr Arg Ile Thr Tyr Gly Glu Thr Gly Gly Asn Ser Pro Val Gln Glu
        210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
                260                 265                 270

Ile Asp Lys Pro Ser Met Ala Ile Pro Ala Pro Thr Asp Leu Lys Phe
            275                 280                 285

Thr Gln Val Thr Pro Thr Ser Leu Ser Ala Gln Trp Thr Pro Pro Asn
        290                 295                 300

Val Gln Leu Thr Gly Tyr Arg Val Arg Val Thr Pro Lys Glu Lys Thr
305                 310                 315                 320

Gly Pro Met Lys Glu Ile Asn Leu Ala Pro Asp Ser Ser Ser Val Val
                325                 330                 335

Val Ser Gly Leu Met Val Ala Thr Lys Tyr Glu Val Ser Val Tyr Ala
                340                 345                 350

Leu Lys Asp Thr Leu Thr Ser Arg Pro Ala Gln Gly Val Val Thr Thr
            355                 360                 365

Leu Glu Asn Val Ser Pro Pro Arg Arg Ala Arg Val Thr Asp Ala Thr
        370                 375                 380

Glu Thr Thr Ile Thr Ile Ser Trp Arg Thr Lys Thr Glu Thr Ile Thr
385                 390                 395                 400

Gly Phe Gln Val Asp Ala Val Pro Ala Asn Gly Gln Thr Pro Ile Gln
                405                 410                 415

Arg Thr Ile Lys Pro Asp Val Arg Ser Tyr Thr Ile Thr Gly Leu Gln
                420                 425                 430

Pro Gly Thr Asp Tyr Lys Ile Tyr Leu Tyr Thr Leu Asn Asp Asn Ala
            435                 440                 445

Arg Ser Ser Pro Val Val Ile Asp Ala Ser Thr Ala Ile Asp Ala Pro
        450                 455                 460

Ser Asn Leu Arg Phe Leu Ala Thr Thr Pro Asn Ser Leu Leu Val Ser
465                 470                 475                 480

Trp Gln Pro Pro Arg Ala Arg Ile Thr Gly Tyr Ile Ile Lys Tyr Glu
                485                 490                 495

Lys Pro Gly Ser Pro Pro Arg Glu Val Val Pro Arg Pro Arg Pro Gly
                500                 505                 510

Val Thr Glu Ala Thr Ile Thr Gly Leu Glu Pro Gly Thr Glu Tyr Thr
            515                 520                 525

Ile Tyr Val Ile Ala Leu Lys Asn Asn Gln Lys Ser Glu Pro Leu Ile
        530                 535                 540

Gly Arg Lys Lys Thr Asp Glu Leu Pro Gln Leu Val Thr Leu Pro His
545                 550                 555                 560
```

Pro Asn Leu His Gly Pro Glu Ile Leu Asp Val Pro Ser Thr
            565                 570

<210> SEQ ID NO 19
<211> LENGTH: 881
<212> TYPE: PRT
<213> ORGANISM: Artificial Sequence
<220> FEATURE:
<223> OTHER INFORMATION: Fibronectin fragment named FCH-296

<400> SEQUENCE: 19

Met Ser Gly Pro Val Glu Val Phe Ile Thr Glu Thr Pro Ser Gln Pro
1               5                   10                  15

Asn Ser His Pro Ile Gln Trp Asn Ala Pro Gln Pro Ser His Ile Ser
            20                  25                  30

Lys Tyr Ile Leu Arg Trp Arg Pro Lys Asn Ser Val Gly Arg Trp Lys
        35                  40                  45

Glu Ala Thr Ile Pro Gly His Leu Asn Ser Tyr Thr Ile Lys Gly Leu
    50                  55                  60

Lys Pro Gly Val Val Tyr Glu Gly Gln Leu Ile Ser Ile Gln Gln Tyr
65                  70                  75                  80

Gly His Gln Glu Val Thr Arg Phe Asp Phe Thr Thr Thr Ser Thr Ser
                85                  90                  95

Thr Pro Val Thr Ser Asn Thr Val Thr Gly Glu Thr Thr Pro Phe Ser
            100                 105                 110

Pro Leu Val Ala Thr Ser Glu Ser Val Thr Glu Ile Thr Ala Ser Ser
        115                 120                 125

Phe Val Val Ser Trp Val Ser Ala Ser Asp Thr Val Ser Gly Phe Arg
130                 135                 140

Val Glu Tyr Glu Leu Ser Glu Glu Gly Asp Glu Pro Gln Tyr Leu Asp
145                 150                 155                 160

Leu Pro Ser Thr Ala Thr Ser Val Asn Ile Pro Asp Leu Leu Pro Gly
                165                 170                 175

Arg Lys Tyr Ile Val Asn Val Tyr Gln Ile Ser Glu Asp Gly Glu Gln
            180                 185                 190

Ser Leu Ile Leu Ser Thr Ser Gln Thr Thr Ala Pro Asp Ala Pro Pro
        195                 200                 205

Asp Pro Thr Val Asp Gln Val Asp Asp Thr Ser Ile Val Val Arg Trp
210                 215                 220

Ser Arg Pro Gln Ala Pro Ile Thr Gly Tyr Arg Ile Val Tyr Ser Pro
225                 230                 235                 240

Ser Val Glu Gly Ser Ser Thr Glu Leu Asn Leu Pro Glu Thr Ala Asn
                245                 250                 255

Ser Val Thr Leu Ser Asp Leu Gln Pro Gly Val Gln Tyr Asn Ile Thr
            260                 265                 270

Ile Tyr Ala Val Glu Glu Asn Gln Glu Ser Thr Pro Val Val Ile Gln
        275                 280                 285

Gln Glu Thr Thr Gly Thr Pro Arg Ser Asp Gly Ser Ser Gly Ser Ser
    290                 295                 300

Gly Ser Ser Pro Thr Asp Leu Arg Phe Thr Asn Ile Gly Pro Asp Thr
305                 310                 315                 320

Met Arg Val Thr Trp Ala Pro Pro Ser Ile Asp Leu Thr Asn Phe
                325                 330                 335

Leu Val Arg Tyr Ser Pro Val Lys Asn Glu Glu Asp Val Ala Glu Leu
            340                 345                 350

```
Ser Ile Ser Pro Ser Asp Asn Ala Val Val Leu Thr Asn Leu Leu Pro
        355                 360                 365

Gly Thr Glu Tyr Val Val Ser Val Ser Ser Val Tyr Glu Gln His Glu
    370                 375                 380

Ser Thr Pro Leu Arg Gly Arg Gln Lys Thr Gly Leu Asp Ser Pro Thr
385                 390                 395                 400

Gly Ile Asp Phe Ser Asp Ile Thr Ala Asn Ser Phe Thr Val His Trp
                405                 410                 415

Ile Ala Pro Arg Ala Thr Ile Thr Gly Tyr Arg Ile Arg His His Pro
                420                 425                 430

Glu His Phe Ser Gly Arg Pro Arg Glu Asp Arg Val Pro His Ser Arg
        435                 440                 445

Asn Ser Ile Thr Leu Thr Asn Leu Thr Pro Gly Thr Glu Tyr Val Val
        450                 455                 460

Ser Ile Val Ala Leu Asn Gly Arg Glu Glu Ser Pro Leu Leu Ile Gly
465                 470                 475                 480

Gln Gln Ser Thr Val Ser Asp Val Pro Arg Asp Leu Glu Val Val Ala
                485                 490                 495

Ala Thr Pro Thr Ser Leu Leu Ile Ser Trp Asp Ala Pro Ala Val Thr
                500                 505                 510

Val Arg Tyr Tyr Arg Ile Thr Tyr Gly Glu Thr Gly Gly Asn Ser Pro
            515                 520                 525

Val Gln Glu Phe Thr Val Pro Gly Ser Lys Ser Thr Ala Thr Ile Ser
        530                 535                 540

Gly Leu Lys Pro Gly Val Asp Tyr Thr Ile Thr Val Tyr Ala Val Thr
545                 550                 555                 560

Gly Arg Gly Asp Ser Pro Ala Ser Ser Lys Pro Ile Ser Ile Asn Tyr
                565                 570                 575

Arg Thr Glu Ile Asp Lys Pro Ser Met Ala Ile Pro Ala Pro Thr Asp
            580                 585                 590

Leu Lys Phe Thr Gln Val Thr Pro Thr Ser Leu Ser Ala Gln Trp Thr
        595                 600                 605

Pro Pro Asn Val Gln Leu Thr Gly Tyr Arg Val Arg Val Thr Pro Lys
        610                 615                 620

Glu Lys Thr Gly Pro Met Lys Glu Ile Asn Leu Ala Pro Asp Ser Ser
625                 630                 635                 640

Ser Val Val Val Ser Gly Leu Met Val Ala Thr Lys Tyr Glu Val Ser
                645                 650                 655

Val Tyr Ala Leu Lys Asp Thr Leu Thr Ser Arg Pro Ala Gln Gly Val
                660                 665                 670

Val Thr Thr Leu Glu Asn Val Ser Pro Pro Arg Arg Ala Arg Val Thr
        675                 680                 685

Asp Ala Thr Glu Thr Thr Ile Thr Ile Ser Trp Arg Thr Lys Thr Glu
        690                 695                 700

Thr Ile Thr Gly Phe Gln Val Asp Ala Val Pro Ala Asn Gly Gln Thr
705                 710                 715                 720

Pro Ile Gln Arg Thr Ile Lys Pro Asp Val Arg Ser Tyr Thr Ile Thr
                725                 730                 735

Gly Leu Gln Pro Gly Thr Asp Tyr Lys Ile Tyr Leu Tyr Thr Leu Asn
            740                 745                 750

Asp Asn Ala Arg Ser Ser Pro Val Val Ile Asp Ala Ser Thr Ala Ile
        755                 760                 765
```

-continued

```
Asp Ala Pro Ser Asn Leu Arg Phe Leu Ala Thr Thr Pro Asn Ser Leu
770                 775                 780
Leu Val Ser Trp Gln Pro Pro Arg Ala Arg Ile Thr Gly Tyr Ile Ile
785                 790                 795                 800
Lys Tyr Glu Lys Pro Gly Ser Pro Pro Arg Glu Val Val Pro Arg Pro
            805                 810                 815
Arg Pro Gly Val Thr Glu Ala Thr Ile Thr Gly Leu Glu Pro Gly Thr
            820                 825                 830
Glu Tyr Thr Ile Tyr Val Ile Ala Leu Lys Asn Asn Gln Lys Ser Glu
            835                 840                 845
Pro Leu Ile Gly Arg Lys Lys Thr Asp Glu Leu Pro Gln Leu Val Thr
850                 855                 860
Leu Pro His Pro Asn Leu His Gly Pro Glu Ile Leu Asp Val Pro Ser
865                 870                 875                 880
Thr
```

<210> SEQ ID NO 20
<211> LENGTH: 851
<212> TYPE: PRT
<213> ORGANISM: Artificial Sequence
<220> FEATURE:
<223> OTHER INFORMATION: Fibronectin fragment named DCH-296

<400> SEQUENCE: 20

```
Met Thr Val Pro Ser Pro Arg Asp Leu Gln Phe Val Glu Val Thr Asp
1               5                   10                  15
Val Lys Val Thr Ile Met Trp Thr Pro Pro Glu Ser Ala Val Thr Gly
            20                  25                  30
Tyr Arg Val Asp Val Ile Pro Val Asn Leu Pro Gly Glu His Gly Gln
        35                  40                  45
Arg Leu Pro Ile Ser Arg Asn Thr Phe Ala Glu Val Thr Gly Leu Ser
    50                  55                  60
Pro Gly Val Thr Tyr Tyr Phe Lys Val Phe Ala Val Ser His Gly Arg
65                  70                  75                  80
Glu Ser Lys Pro Leu Thr Ala Gln Gln Thr Thr Lys Leu Asp Ala Pro
                85                  90                  95
Thr Asn Leu Gln Phe Val Asn Glu Thr Asp Ser Thr Val Leu Val Arg
            100                 105                 110
Trp Thr Pro Pro Arg Ala Gln Ile Thr Gly Tyr Arg Leu Thr Val Gly
        115                 120                 125
Leu Thr Arg Arg Gly Gln Pro Arg Gln Tyr Asn Val Gly Pro Ser Val
    130                 135                 140
Ser Lys Tyr Pro Leu Arg Asn Leu Gln Pro Ala Ser Glu Tyr Thr Val
145                 150                 155                 160
Ser Leu Val Ala Ile Lys Gly Asn Gln Glu Ser Pro Lys Ala Thr Gly
                165                 170                 175
Val Phe Thr Thr Leu Gln Pro Gly Ser Ser Ile Pro Pro Tyr Asn Thr
            180                 185                 190
Glu Val Thr Glu Thr Thr Ile Val Ile Thr Trp Thr Pro Ala Pro Arg
        195                 200                 205
Ile Gly Phe Lys Leu Gly Val Arg Pro Ser Gln Gly Gly Glu Ala Pro
    210                 215                 220
Arg Glu Val Thr Ser Asp Ser Gly Ser Ile Val Val Ser Gly Leu Thr
225                 230                 235                 240
Pro Gly Val Glu Tyr Val Tyr Thr Ile Gln Val Leu Arg Asp Gly Gln
```

```
            245                 250                 255
Glu Arg Asp Ala Pro Ile Val Asn Lys Val Thr Gly Ser Ser Gly
            260                 265                 270

Ser Ser Gly Ser Ser Pro Thr Asp Leu Arg Phe Thr Asn Ile Gly Pro
        275                 280                 285

Asp Thr Met Arg Val Thr Trp Ala Pro Pro Ser Ile Asp Leu Thr
        290                 295                 300

Asn Phe Leu Val Arg Tyr Ser Pro Val Lys Asn Glu Glu Asp Val Ala
305                 310                 315                 320

Glu Leu Ser Ile Ser Pro Ser Asp Asn Ala Val Val Leu Thr Asn Leu
                325                 330                 335

Leu Pro Gly Thr Glu Tyr Val Val Ser Val Ser Ser Val Tyr Glu Gln
            340                 345                 350

His Glu Ser Thr Pro Leu Arg Gly Arg Gln Lys Thr Gly Leu Asp Ser
            355                 360                 365

Pro Thr Gly Ile Asp Phe Ser Asp Ile Thr Ala Asn Ser Phe Thr Val
        370                 375                 380

His Trp Ile Ala Pro Arg Ala Thr Ile Thr Gly Tyr Arg Ile Arg His
385                 390                 395                 400

His Pro Glu His Phe Ser Gly Arg Pro Arg Glu Asp Arg Val Pro His
                405                 410                 415

Ser Arg Asn Ser Ile Thr Leu Thr Asn Leu Thr Pro Gly Thr Glu Tyr
            420                 425                 430

Val Val Ser Ile Val Ala Leu Asn Gly Arg Glu Glu Ser Pro Leu Leu
            435                 440                 445

Ile Gly Gln Gln Ser Thr Val Ser Asp Val Pro Arg Asp Leu Glu Val
        450                 455                 460

Val Ala Ala Thr Pro Thr Ser Leu Leu Ile Ser Trp Asp Ala Pro Ala
465                 470                 475                 480

Val Thr Val Arg Tyr Tyr Arg Ile Thr Tyr Gly Glu Thr Gly Gly Asn
                485                 490                 495

Ser Pro Val Gln Glu Phe Thr Val Pro Gly Ser Lys Ser Thr Ala Thr
            500                 505                 510

Ile Ser Gly Leu Lys Pro Gly Val Asp Tyr Thr Ile Thr Val Tyr Ala
        515                 520                 525

Val Thr Gly Arg Gly Asp Ser Pro Ala Ser Ser Lys Pro Ile Ser Ile
        530                 535                 540

Asn Tyr Arg Thr Glu Ile Asp Lys Pro Ser Met Ala Ile Pro Ala Pro
545                 550                 555                 560

Thr Asp Leu Lys Phe Thr Gln Val Thr Pro Thr Ser Leu Ser Ala Gln
                565                 570                 575

Trp Thr Pro Pro Asn Val Gln Leu Thr Gly Tyr Arg Val Arg Val Thr
            580                 585                 590

Pro Lys Glu Lys Thr Gly Pro Met Lys Glu Ile Asn Leu Ala Pro Asp
            595                 600                 605

Ser Ser Ser Val Val Val Ser Gly Leu Met Val Ala Thr Lys Tyr Glu
        610                 615                 620

Val Ser Val Tyr Ala Leu Lys Asp Thr Leu Thr Ser Arg Pro Ala Gln
625                 630                 635                 640

Gly Val Val Thr Thr Leu Glu Asn Val Ser Pro Pro Arg Arg Ala Arg
                645                 650                 655

Val Thr Asp Ala Thr Glu Thr Thr Ile Thr Ile Ser Trp Arg Thr Lys
            660                 665                 670
```

-continued

Thr Glu Thr Ile Thr Gly Phe Gln Val Asp Ala Val Pro Ala Asn Gly
            675                 680                 685

Gln Thr Pro Ile Gln Arg Thr Ile Lys Pro Asp Val Arg Ser Tyr Thr
    690                 695                 700

Ile Thr Gly Leu Gln Pro Gly Thr Asp Tyr Lys Ile Tyr Leu Tyr Thr
705                 710                 715                 720

Leu Asn Asp Asn Ala Arg Ser Ser Pro Val Val Ile Asp Ala Ser Thr
                725                 730                 735

Ala Ile Asp Ala Pro Ser Asn Leu Arg Phe Leu Ala Thr Thr Pro Asn
                740                 745                 750

Ser Leu Leu Val Ser Trp Gln Pro Pro Arg Ala Arg Ile Thr Gly Tyr
            755                 760                 765

Ile Ile Lys Tyr Glu Lys Pro Gly Ser Pro Pro Arg Glu Val Val Pro
    770                 775                 780

Arg Pro Arg Pro Gly Val Thr Glu Ala Thr Ile Thr Gly Leu Glu Pro
785                 790                 795                 800

Gly Thr Glu Tyr Thr Ile Tyr Val Ile Ala Leu Lys Asn Asn Gln Lys
                805                 810                 815

Ser Glu Pro Leu Ile Gly Arg Lys Lys Thr Asp Glu Leu Pro Gln Leu
                820                 825                 830

Val Thr Leu Pro His Pro Asn Leu His Gly Pro Glu Ile Leu Asp Val
            835                 840                 845

Pro Ser Thr
850

<210> SEQ ID NO 21
<211> LENGTH: 887
<212> TYPE: PRT
<213> ORGANISM: Artificial Sequence
<220> FEATURE:
<223> OTHER INFORMATION: His-tag FCH-296

<400> SEQUENCE: 21

Met His His His His His Ser Gly Pro Val Glu Val Phe Ile Thr
1               5                   10                  15

Glu Thr Pro Ser Gln Pro Asn Ser His Pro Ile Gln Trp Asn Ala Pro
                20                  25                  30

Gln Pro Ser His Ile Ser Lys Tyr Ile Leu Arg Trp Arg Pro Lys Asn
            35                  40                  45

Ser Val Gly Arg Trp Lys Glu Ala Thr Ile Pro Gly His Leu Asn Ser
    50                  55                  60

Tyr Thr Ile Lys Gly Leu Lys Pro Gly Val Val Tyr Glu Gly Gln Leu
65                  70                  75                  80

Ile Ser Ile Gln Gln Tyr Gly His Gln Glu Val Thr Arg Phe Asp Phe
                85                  90                  95

Thr Thr Thr Ser Thr Ser Thr Pro Val Thr Ser Asn Thr Val Thr Gly
                100                 105                 110

Glu Thr Thr Pro Phe Ser Pro Leu Val Ala Thr Ser Glu Ser Val Thr
            115                 120                 125

Glu Ile Thr Ala Ser Ser Phe Val Val Ser Trp Val Ser Ala Ser Asp
    130                 135                 140

Thr Val Ser Gly Phe Arg Val Glu Tyr Glu Leu Ser Glu Glu Gly Asp
145                 150                 155                 160

Glu Pro Gln Tyr Leu Asp Leu Pro Ser Thr Ala Thr Ser Val Asn Ile
                165                 170                 175

```
Pro Asp Leu Leu Pro Gly Arg Lys Tyr Ile Val Asn Val Tyr Gln Ile
            180                 185                 190

Ser Glu Asp Gly Glu Gln Ser Leu Ile Leu Ser Thr Ser Gln Thr Thr
        195                 200                 205

Ala Pro Asp Ala Pro Pro Asp Pro Thr Val Asp Gln Val Asp Asp Thr
    210                 215                 220

Ser Ile Val Val Arg Trp Ser Arg Pro Gln Ala Pro Ile Thr Gly Tyr
225                 230                 235                 240

Arg Ile Val Tyr Ser Pro Ser Val Glu Gly Ser Ser Thr Glu Leu Asn
                245                 250                 255

Leu Pro Glu Thr Ala Asn Ser Val Thr Leu Ser Asp Leu Gln Pro Gly
        260                 265                 270

Val Gln Tyr Asn Ile Thr Ile Tyr Ala Val Glu Glu Asn Gln Glu Ser
            275                 280                 285

Thr Pro Val Val Ile Gln Gln Glu Thr Thr Gly Thr Pro Arg Ser Asp
    290                 295                 300

Gly Ser Ser Gly Ser Ser Gly Ser Ser Pro Thr Asp Leu Arg Phe Thr
305                 310                 315                 320

Asn Ile Gly Pro Asp Thr Met Arg Val Thr Trp Ala Pro Pro Pro Ser
                325                 330                 335

Ile Asp Leu Thr Asn Phe Leu Val Arg Tyr Ser Pro Val Lys Asn Glu
        340                 345                 350

Glu Asp Val Ala Glu Leu Ser Ile Ser Pro Ser Asp Asn Ala Val Val
            355                 360                 365

Leu Thr Asn Leu Leu Pro Gly Thr Glu Tyr Val Val Ser Val Ser Ser
    370                 375                 380

Val Tyr Glu Gln His Glu Ser Thr Pro Leu Arg Gly Arg Gln Lys Thr
385                 390                 395                 400

Gly Leu Asp Ser Pro Thr Gly Ile Asp Phe Ser Asp Ile Thr Ala Asn
                405                 410                 415

Ser Phe Thr Val His Trp Ile Ala Pro Arg Ala Thr Ile Thr Gly Tyr
        420                 425                 430

Arg Ile Arg His His Pro Glu His Phe Ser Gly Arg Pro Arg Glu Asp
            435                 440                 445

Arg Val Pro His Ser Arg Asn Ser Ile Thr Leu Thr Asn Leu Thr Pro
    450                 455                 460

Gly Thr Glu Tyr Val Val Ser Ile Val Ala Leu Asn Gly Arg Glu Glu
465                 470                 475                 480

Ser Pro Leu Leu Ile Gly Gln Gln Ser Thr Val Ser Asp Val Pro Arg
                485                 490                 495

Asp Leu Glu Val Val Ala Ala Thr Pro Thr Ser Leu Leu Ile Ser Trp
        500                 505                 510

Asp Ala Pro Ala Val Thr Val Arg Tyr Tyr Arg Ile Thr Tyr Gly Glu
            515                 520                 525

Thr Gly Gly Asn Ser Pro Val Gln Glu Phe Thr Val Pro Gly Ser Lys
    530                 535                 540

Ser Thr Ala Thr Ile Ser Gly Leu Lys Pro Gly Val Asp Tyr Thr Ile
545                 550                 555                 560

Thr Val Tyr Ala Val Thr Gly Arg Gly Asp Ser Pro Ala Ser Ser Lys
                565                 570                 575

Pro Ile Ser Ile Asn Tyr Arg Thr Glu Ile Asp Lys Pro Ser Met Ala
        580                 585                 590
```

```
Ile Pro Ala Pro Thr Asp Leu Lys Phe Thr Gln Val Thr Pro Thr Ser
            595                 600                 605

Leu Ser Ala Gln Trp Thr Pro Pro Asn Val Gln Leu Thr Gly Tyr Arg
    610                 615                 620

Val Arg Val Thr Pro Lys Glu Lys Thr Gly Pro Met Lys Glu Ile Asn
625                 630                 635                 640

Leu Ala Pro Asp Ser Ser Val Val Ser Gly Leu Met Val Ala
            645                 650                 655

Thr Lys Tyr Glu Val Ser Val Tyr Ala Leu Lys Asp Thr Leu Thr Ser
                660                 665                 670

Arg Pro Ala Gln Gly Val Val Thr Thr Leu Glu Asn Val Ser Pro Pro
            675                 680                 685

Arg Arg Ala Arg Val Thr Asp Ala Thr Glu Thr Thr Ile Thr Ile Ser
690                 695                 700

Trp Arg Thr Lys Thr Glu Thr Ile Thr Gly Phe Gln Val Asp Ala Val
705                 710                 715                 720

Pro Ala Asn Gly Gln Thr Pro Ile Gln Arg Thr Ile Lys Pro Asp Val
                725                 730                 735

Arg Ser Tyr Thr Ile Thr Gly Leu Gln Pro Gly Thr Asp Tyr Lys Ile
                740                 745                 750

Tyr Leu Tyr Thr Leu Asn Asp Asn Ala Arg Ser Ser Pro Val Val Ile
                755                 760                 765

Asp Ala Ser Thr Ala Ile Asp Ala Pro Ser Asn Leu Arg Phe Leu Ala
            770                 775                 780

Thr Thr Pro Asn Ser Leu Leu Val Ser Trp Gln Pro Pro Arg Ala Arg
785                 790                 795                 800

Ile Thr Gly Tyr Ile Ile Lys Tyr Glu Lys Pro Gly Ser Pro Pro Arg
                805                 810                 815

Glu Val Val Pro Arg Pro Arg Pro Gly Val Thr Glu Ala Thr Ile Thr
                820                 825                 830

Gly Leu Glu Pro Gly Thr Glu Tyr Thr Ile Tyr Val Ile Ala Leu Lys
                835                 840                 845

Asn Asn Gln Lys Ser Glu Pro Leu Ile Gly Arg Lys Lys Thr Asp Glu
850                 855                 860

Leu Pro Gln Leu Val Thr Leu Pro His Pro Asn Leu His Gly Pro Glu
865                 870                 875                 880

Ile Leu Asp Val Pro Ser Thr
                885

<210> SEQ ID NO 22
<211> LENGTH: 832
<212> TYPE: PRT
<213> ORGANISM: Artificial Sequence
<220> FEATURE:
<223> OTHER INFORMATION: His-tag DCH-296

<400> SEQUENCE: 22

Met His His His His His Thr Val Pro Ser Pro Arg Asp Leu Gln
1               5                   10                  15

Phe Val Glu Val Thr Asp Val Lys Val Thr Ile Met Trp Thr Pro Pro
                20                  25                  30

Glu Ser Ala Val Thr Gly Tyr Arg Val Asp Val Ile Pro Val Asn Leu
            35                  40                  45

Pro Gly Glu His Gly Gln Arg Leu Pro Ile Ser Arg Asn Thr Phe Ala
    50                  55                  60
```

-continued

```
Glu Val Thr Gly Leu Ser Pro Gly Val Thr Tyr Tyr Phe Lys Val Phe
 65                  70                  75                  80

Ala Val Ser His Gly Arg Glu Ser Lys Pro Leu Thr Ala Gln Gln Thr
                 85                  90                  95

Thr Lys Leu Asp Ala Pro Thr Asn Leu Gln Phe Val Asn Glu Thr Asp
                100                 105                 110

Ser Thr Val Leu Val Arg Trp Thr Pro Pro Arg Ala Gln Ile Thr Gly
            115                 120                 125

Tyr Arg Leu Thr Val Gly Leu Thr Arg Arg Gly Gln Pro Arg Gln Tyr
            130                 135                 140

Asn Val Gly Pro Ser Val Ser Lys Tyr Pro Leu Arg Asn Leu Gln Pro
145                 150                 155                 160

Ala Ser Glu Tyr Thr Val Ser Leu Val Ala Ile Lys Gly Asn Gln Glu
                165                 170                 175

Ser Pro Lys Ala Thr Gly Val Phe Thr Thr Leu Gln Pro Gly Ser Ser
                180                 185                 190

Ile Pro Pro Tyr Asn Thr Glu Val Thr Glu Thr Thr Ile Val Ile Thr
                195                 200                 205

Trp Thr Pro Ala Pro Arg Ile Gly Phe Lys Leu Gly Val Arg Pro Ser
210                 215                 220

Gln Gly Gly Glu Ala Pro Arg Glu Val Thr Ser Asp Ser Gly Ser Ile
225                 230                 235                 240

Val Val Ser Gly Leu Thr Pro Gly Val Glu Tyr Val Tyr Thr Ile Gln
                245                 250                 255

Val Leu Arg Asp Gly Gln Glu Arg Asp Ala Pro Ile Val Asn Lys Val
            260                 265                 270

Val Thr Gly Ser Ser Gly Ser Ser Gly Ser Ser Pro Thr Asp Leu Arg
            275                 280                 285

Phe Thr Asn Ile Gly Pro Asp Thr Met Arg Val Thr Trp Ala Pro Pro
            290                 295                 300

Pro Ser Ile Asp Leu Thr Asn Phe Leu Val Arg Tyr Ser Pro Val Lys
305                 310                 315                 320

Asn Glu Glu Asp Val Ala Glu Leu Ser Ile Ser Pro Ser Asp Asn Ala
                325                 330                 335

Val Val Leu Thr Asn Leu Leu Pro Gly Thr Glu Tyr Val Val Ser Val
                340                 345                 350

Ser Ser Val Tyr Glu Gln His Glu Ser Thr Pro Leu Arg Gly Arg Gln
            355                 360                 365

Lys Thr Gly Leu Asp Ser Pro Thr Gly Ile Asp Phe Ser Asp Ile Thr
370                 375                 380

Ala Asn Ser Phe Thr Val His Trp Ile Ala Pro Arg Ala Thr Ile Thr
385                 390                 395                 400

Gly Tyr Arg Ile Arg His His Pro Glu His Phe Ser Gly Arg Pro Arg
            405                 410                 415

Glu Asp Arg Val Pro His Ser Arg Asn Ser Ile Thr Leu Thr Asn Leu
            420                 425                 430

Thr Pro Gly Thr Glu Tyr Val Val Ser Ile Val Ala Leu Asn Gly Arg
            435                 440                 445

Glu Glu Ser Pro Leu Leu Ile Gly Gln Gln Ser Thr Val Ser Asp Val
            450                 455                 460

Pro Arg Asp Leu Glu Val Val Ala Ala Thr Pro Thr Ser Leu Leu Ile
465                 470                 475                 480

Ser Trp Asp Ala Pro Ala Val Thr Val Arg Tyr Tyr Arg Ile Thr Tyr
```

```
                485                 490                 495
Gly Glu Thr Gly Gly Asn Ser Pro Val Gln Glu Phe Thr Val Pro Gly
            500                 505                 510

Ser Lys Ser Thr Ala Thr Ile Ser Gly Leu Lys Pro Gly Val Asp Tyr
            515                 520                 525

Thr Ile Thr Val Tyr Ala Val Thr Gly Arg Gly Asp Ser Pro Ala Ser
            530                 535                 540

Ser Lys Pro Ile Ser Ile Asn Tyr Arg Thr Glu Ile Asp Lys Pro Ser
545                 550                 555                 560

Met Ala Ile Pro Ala Pro Thr Asp Leu Lys Phe Thr Gln Val Thr Pro
                565                 570                 575

Thr Ser Leu Ser Ala Gln Trp Thr Pro Pro Asn Val Gln Leu Thr Gly
            580                 585                 590

Tyr Arg Val Arg Val Thr Pro Lys Glu Lys Thr Gly Pro Met Lys Glu
            595                 600                 605

Ile Asn Leu Ala Pro Asp Ser Ser Ser Val Val Val Ser Gly Leu Met
            610                 615                 620

Val Ala Thr Lys Tyr Glu Val Ser Val Tyr Ala Leu Lys Asp Thr Leu
625                 630                 635                 640

Thr Ser Arg Pro Ala Gln Gly Val Val Thr Thr Leu Glu Asn Val Ser
                645                 650                 655

Pro Pro Arg Arg Ala Arg Val Thr Asp Ala Thr Glu Thr Thr Ile Thr
            660                 665                 670

Ile Ser Trp Arg Thr Lys Thr Glu Thr Ile Thr Gly Phe Gln Val Asp
            675                 680                 685

Ala Val Pro Ala Asn Gly Gln Thr Pro Ile Gln Arg Thr Ile Lys Pro
            690                 695                 700

Asp Val Arg Ser Tyr Thr Ile Thr Gly Leu Gln Pro Gly Thr Asp Tyr
705                 710                 715                 720

Lys Ile Tyr Leu Tyr Thr Leu Asn Asp Asn Ala Arg Ser Ser Pro Val
                725                 730                 735

Val Ile Asp Ala Ser Thr Ala Ile Asp Ala Pro Ser Asn Leu Arg Phe
            740                 745                 750

Leu Ala Thr Thr Pro Asn Ser Leu Leu Val Ser Trp Gln Pro Pro Arg
            755                 760                 765

Ala Arg Ile Thr Gly Tyr Ile Ile Lys Tyr Glu Lys Pro Gly Ser Pro
            770                 775                 780

Pro Arg Glu Val Val Pro Arg Pro Arg Pro Gly Val Thr Glu Ala Thr
785                 790                 795                 800

Ile Thr Gly Leu Glu Pro Gly Thr Glu Tyr Thr Ile Tyr Val Ile Ala
                805                 810                 815

Leu Lys Asn Asn Gln Lys Ser Glu Pro Leu Ile Gly Arg Lys Lys Thr
            820                 825                 830

<210> SEQ ID NO 23
<211> LENGTH: 83
<212> TYPE: PRT
<213> ORGANISM: Artificial Sequence
<220> FEATURE:
<223> OTHER INFORMATION: N-terminal 9a.a. deletion of III-1

<400> SEQUENCE: 23

Glu Thr Pro Ser Gln Pro Asn Ser His Pro Ile Gln Trp Asn Ala Pro
1               5                   10                  15

Gln Pro Ser His Ile Ser Lys Tyr Ile Leu Arg Trp Arg Pro Lys Asn
```

-continued

```
                20                  25                  30
Ser Val Gly Arg Trp Lys Glu Ala Thr Ile Pro Gly His Leu Asn Ser
            35                  40                  45

Tyr Thr Ile Lys Gly Leu Lys Pro Gly Val Val Tyr Glu Gly Gln Leu
        50                  55                  60

Ile Ser Ile Gln Gln Tyr Gly His Gln Glu Val Thr Arg Phe Asp Phe
65                  70                  75                  80

Thr Thr Thr
```

<210> SEQ ID NO 24
<211> LENGTH: 87
<212> TYPE: PRT
<213> ORGANISM: Artificial Sequence
<220> FEATURE:
<223> OTHER INFORMATION: N-terminal 5a.a. deletion of III-1

<400> SEQUENCE: 24

```
Val Phe Ile Thr Glu Thr Pro Ser Gln Pro Asn Ser His Pro Ile Gln
1               5                   10                  15

Trp Asn Ala Pro Gln Pro Ser His Ile Ser Lys Tyr Ile Leu Arg Trp
            20                  25                  30

Arg Pro Lys Asn Ser Val Gly Arg Trp Lys Glu Ala Thr Ile Pro Gly
        35                  40                  45

His Leu Asn Ser Tyr Thr Ile Lys Gly Leu Lys Pro Gly Val Val Tyr
    50                  55                  60

Glu Gly Gln Leu Ile Ser Ile Gln Gln Tyr Gly His Gln Glu Val Thr
65                  70                  75                  80

Arg Phe Asp Phe Thr Thr Thr
                85
```

<210> SEQ ID NO 25
<211> LENGTH: 89
<212> TYPE: PRT
<213> ORGANISM: Artificial Sequence
<220> FEATURE:
<223> OTHER INFORMATION: N-terminal 3a.a. deletion of III-1

<400> SEQUENCE: 25

```
Val Glu Val Phe Ile Thr Glu Thr Pro Ser Gln Pro Asn Ser His Pro
1               5                   10                  15

Ile Gln Trp Asn Ala Pro Gln Pro Ser His Ile Ser Lys Tyr Ile Leu
            20                  25                  30

Arg Trp Arg Pro Lys Asn Ser Val Gly Arg Trp Lys Glu Ala Thr Ile
        35                  40                  45

Pro Gly His Leu Asn Ser Tyr Thr Ile Lys Gly Leu Lys Pro Gly Val
    50                  55                  60

Val Tyr Glu Gly Gln Leu Ile Ser Ile Gln Gln Tyr Gly His Gln Glu
65                  70                  75                  80

Val Thr Arg Phe Asp Phe Thr Thr Thr
                85
```

<210> SEQ ID NO 26
<211> LENGTH: 682
<212> TYPE: PRT
<213> ORGANISM: Artificial Sequence
<220> FEATURE:
<223> OTHER INFORMATION: His-tag F1CH-296

<400> SEQUENCE: 26

```
Met His His His His His Ser Gly Pro Val Glu Val Phe Ile Thr
 1               5                  10                  15

Glu Thr Pro Ser Gln Pro Asn Ser His Pro Ile Gln Trp Asn Ala Pro
             20                  25                  30

Gln Pro Ser His Ile Ser Lys Tyr Ile Leu Arg Trp Arg Pro Lys Asn
             35                  40                  45

Ser Val Gly Arg Trp Lys Glu Ala Thr Ile Pro Gly His Leu Asn Ser
 50                  55                  60

Tyr Thr Ile Lys Gly Leu Lys Pro Gly Val Val Tyr Glu Gly Gln Leu
 65                  70                  75                  80

Ile Ser Ile Gln Gln Tyr Gly His Gln Glu Val Thr Arg Phe Asp Phe
                 85                  90                  95

Thr Thr Thr Gly Ser Ser Gly Ser Gly Ser Ser Pro Thr Asp Leu
                100                 105                 110

Arg Phe Thr Asn Ile Gly Pro Asp Thr Met Arg Val Thr Trp Ala Pro
             115                 120                 125

Pro Pro Ser Ile Asp Leu Thr Asn Phe Leu Val Arg Tyr Ser Pro Val
    130                 135                 140

Lys Asn Glu Glu Asp Val Ala Glu Leu Ser Ile Ser Pro Ser Asp Asn
145                 150                 155                 160

Ala Val Val Leu Thr Asn Leu Leu Pro Gly Thr Glu Tyr Val Val Ser
                165                 170                 175

Val Ser Ser Val Tyr Glu Gln His Glu Ser Thr Pro Leu Arg Gly Arg
                180                 185                 190

Gln Lys Thr Gly Leu Asp Ser Pro Thr Gly Ile Asp Phe Ser Asp Ile
        195                 200                 205

Thr Ala Asn Ser Phe Thr Val His Trp Ile Ala Pro Arg Ala Thr Ile
210                 215                 220

Thr Gly Tyr Arg Ile Arg His His Pro Glu His Phe Ser Gly Arg Pro
225                 230                 235                 240

Arg Glu Asp Arg Val Pro His Ser Arg Asn Ser Ile Thr Leu Thr Asn
                245                 250                 255

Leu Thr Pro Gly Thr Glu Tyr Val Val Ser Ile Val Ala Leu Asn Gly
                260                 265                 270

Arg Glu Glu Ser Pro Leu Leu Ile Gly Gln Gln Ser Thr Val Ser Asp
            275                 280                 285

Val Pro Arg Asp Leu Glu Val Val Ala Ala Thr Pro Thr Ser Leu Leu
    290                 295                 300

Ile Ser Trp Asp Ala Pro Ala Val Thr Val Arg Tyr Tyr Arg Ile Thr
305                 310                 315                 320

Tyr Gly Glu Thr Gly Gly Asn Ser Pro Val Gln Glu Phe Thr Val Pro
                325                 330                 335

Gly Ser Lys Ser Thr Ala Thr Ile Ser Gly Leu Lys Pro Gly Val Asp
            340                 345                 350

Tyr Thr Ile Thr Val Tyr Ala Val Thr Gly Arg Gly Asp Ser Pro Ala
        355                 360                 365

Ser Ser Lys Pro Ile Ser Ile Asn Tyr Arg Thr Glu Ile Asp Lys Pro
    370                 375                 380

Ser Met Ala Ile Pro Ala Pro Thr Asp Leu Lys Phe Thr Gln Val Thr
385                 390                 395                 400

Pro Thr Ser Leu Ser Ala Gln Trp Thr Pro Pro Asn Val Gln Leu Thr
                405                 410                 415

Gly Tyr Arg Val Arg Val Thr Pro Lys Glu Lys Thr Gly Pro Met Lys
```

```
                        420                 425                 430
Glu Ile Asn Leu Ala Pro Asp Ser Ser Val Val Ser Gly Leu
            435                 440                 445

Met Val Ala Thr Lys Tyr Glu Val Ser Val Tyr Ala Leu Lys Asp Thr
450                 455                 460

Leu Thr Ser Arg Pro Ala Gln Gly Val Val Thr Leu Glu Asn Val
465                 470                 475                 480

Ser Pro Pro Arg Arg Ala Arg Val Thr Asp Ala Thr Glu Thr Ile
            485                 490                 495

Thr Ile Ser Trp Arg Thr Lys Thr Glu Thr Ile Thr Gly Phe Gln Val
            500                 505                 510

Asp Ala Val Pro Ala Asn Gly Gln Thr Pro Ile Gln Arg Thr Ile Lys
            515                 520                 525

Pro Asp Val Arg Ser Tyr Thr Ile Thr Gly Leu Gln Pro Gly Thr Asp
            530                 535                 540

Tyr Lys Ile Tyr Leu Tyr Thr Leu Asn Asp Asn Ala Arg Ser Ser Pro
545                 550                 555                 560

Val Val Ile Asp Ala Ser Thr Ala Ile Asp Ala Pro Ser Asn Leu Arg
                565                 570                 575

Phe Leu Ala Thr Thr Pro Asn Ser Leu Leu Val Ser Trp Gln Pro Pro
                580                 585                 590

Arg Ala Arg Ile Thr Gly Tyr Ile Ile Lys Tyr Glu Lys Pro Gly Ser
                595                 600                 605

Pro Pro Arg Glu Val Val Pro Arg Pro Arg Pro Gly Val Thr Glu Ala
            610                 615                 620

Thr Ile Thr Gly Leu Glu Pro Gly Thr Glu Tyr Thr Ile Tyr Val Ile
625                 630                 635                 640

Ala Leu Lys Asn Asn Gln Lys Ser Glu Pro Leu Ile Gly Arg Lys Lys
                645                 650                 655

Thr Asp Glu Leu Pro Gln Leu Val Thr Leu Pro His Pro Asn Leu His
                660                 665                 670

Gly Pro Glu Ile Leu Asp Val Pro Ser Thr
            675                 680

<210> SEQ ID NO 27
<211> LENGTH: 699
<212> TYPE: PRT
<213> ORGANISM: Artificial Sequence
<220> FEATURE:
<223> OTHER INFORMATION: His-tag F2CH-296

<400> SEQUENCE: 27

Met His His His His His Ser Thr Ser Thr Pro Val Thr Ser Asn
1               5                   10                  15

Thr Val Thr Gly Glu Thr Thr Pro Phe Ser Pro Leu Val Ala Thr Ser
                20                  25                  30

Glu Ser Val Thr Glu Ile Thr Ala Ser Ser Phe Val Val Ser Trp Val
                35                  40                  45

Ser Ala Ser Asp Thr Val Ser Gly Phe Arg Val Glu Tyr Glu Leu Ser
            50                  55                  60

Glu Glu Gly Asp Glu Pro Gln Tyr Leu Asp Leu Pro Ser Thr Ala Thr
65                  70                  75                  80

Ser Val Asn Ile Pro Asp Leu Leu Pro Gly Arg Lys Tyr Ile Val Asn
                85                  90                  95

Val Tyr Gln Ile Ser Glu Asp Gly Glu Gln Ser Leu Ile Leu Ser Thr
```

```
            100                 105                 110
Ser Gln Thr Thr Gly Ser Ser Gly Ser Ser Gly Ser Ser Pro Thr Asp
            115                 120                 125

Leu Arg Phe Thr Asn Ile Gly Pro Asp Thr Met Arg Val Thr Trp Ala
130                 135                 140

Pro Pro Pro Ser Ile Asp Leu Thr Asn Phe Leu Val Arg Tyr Ser Pro
145                 150                 155                 160

Val Lys Asn Glu Glu Asp Val Ala Glu Leu Ser Ile Ser Pro Ser Asp
                165                 170                 175

Asn Ala Val Val Leu Thr Asn Leu Leu Pro Gly Thr Glu Tyr Val Val
            180                 185                 190

Ser Val Ser Ser Val Tyr Glu Gln His Glu Ser Thr Pro Leu Arg Gly
        195                 200                 205

Arg Gln Lys Thr Gly Leu Asp Ser Pro Thr Gly Ile Asp Phe Ser Asp
    210                 215                 220

Ile Thr Ala Asn Ser Phe Thr Val His Trp Ile Ala Pro Arg Ala Thr
225                 230                 235                 240

Ile Thr Gly Tyr Arg Ile Arg His His Pro Glu His Phe Ser Gly Arg
                245                 250                 255

Pro Arg Glu Asp Arg Val Pro His Ser Arg Asn Ser Ile Thr Leu Thr
            260                 265                 270

Asn Leu Thr Pro Gly Thr Glu Tyr Val Val Ser Ile Val Ala Leu Asn
        275                 280                 285

Gly Arg Glu Glu Ser Pro Leu Leu Ile Gly Gln Gln Ser Thr Val Ser
    290                 295                 300

Asp Val Pro Arg Asp Leu Glu Val Val Ala Ala Thr Pro Thr Ser Leu
305                 310                 315                 320

Leu Ile Ser Trp Asp Ala Pro Ala Val Thr Val Arg Tyr Tyr Arg Ile
                325                 330                 335

Thr Tyr Gly Glu Thr Gly Gly Asn Ser Pro Val Gln Glu Phe Thr Val
            340                 345                 350

Pro Gly Ser Lys Ser Thr Ala Thr Ile Ser Gly Leu Lys Pro Gly Val
        355                 360                 365

Asp Tyr Thr Ile Thr Val Tyr Ala Val Thr Gly Arg Gly Asp Ser Pro
    370                 375                 380

Ala Ser Ser Lys Pro Ile Ser Ile Asn Tyr Arg Thr Glu Ile Asp Lys
385                 390                 395                 400

Pro Ser Met Ala Ile Pro Ala Pro Thr Asp Leu Lys Phe Thr Gln Val
                405                 410                 415

Thr Pro Thr Ser Leu Ser Ala Gln Trp Thr Pro Pro Asn Val Gln Leu
            420                 425                 430

Thr Gly Tyr Arg Val Arg Val Thr Pro Lys Glu Lys Thr Gly Pro Met
        435                 440                 445

Lys Glu Ile Asn Leu Ala Pro Asp Ser Ser Ser Val Val Val Ser Gly
    450                 455                 460

Leu Met Val Ala Thr Lys Tyr Glu Val Ser Val Tyr Ala Leu Lys Asp
465                 470                 475                 480

Thr Leu Thr Ser Arg Pro Ala Gln Gly Val Val Thr Thr Leu Glu Asn
                485                 490                 495

Val Ser Pro Pro Arg Arg Ala Arg Val Thr Asp Ala Thr Glu Thr Thr
            500                 505                 510

Ile Thr Ile Ser Trp Arg Thr Lys Thr Glu Thr Ile Thr Gly Phe Gln
        515                 520                 525
```

```
Val Asp Ala Val Pro Ala Asn Gly Gln Thr Pro Ile Gln Arg Thr Ile
        530                 535                 540

Lys Pro Asp Val Arg Ser Tyr Thr Ile Thr Gly Leu Gln Pro Gly Thr
545                 550                 555                 560

Asp Tyr Lys Ile Tyr Leu Tyr Thr Leu Asn Asp Asn Ala Arg Ser Ser
                565                 570                 575

Pro Val Val Ile Asp Ala Ser Thr Ala Ile Asp Ala Pro Ser Asn Leu
            580                 585                 590

Arg Phe Leu Ala Thr Thr Pro Asn Ser Leu Leu Val Ser Trp Gln Pro
        595                 600                 605

Pro Arg Ala Arg Ile Thr Gly Tyr Ile Ile Lys Tyr Glu Lys Pro Gly
    610                 615                 620

Ser Pro Pro Arg Glu Val Val Pro Arg Pro Arg Pro Gly Val Thr Glu
625                 630                 635                 640

Ala Thr Ile Thr Gly Leu Glu Pro Gly Thr Glu Tyr Thr Ile Tyr Val
                645                 650                 655

Ile Ala Leu Lys Asn Asn Gln Lys Ser Glu Pro Leu Ile Gly Arg Lys
            660                 665                 670

Lys Thr Asp Glu Leu Pro Gln Leu Val Thr Leu Pro His Pro Asn Leu
        675                 680                 685

His Gly Pro Glu Ile Leu Asp Val Pro Ser Thr
    690                 695

<210> SEQ ID NO 28
<211> LENGTH: 686
<212> TYPE: PRT
<213> ORGANISM: Artificial Sequence
<220> FEATURE:
<223> OTHER INFORMATION: His-tag F3CH-296

<400> SEQUENCE: 28

Met His His His His His Ala Pro Asp Ala Pro Pro Asp Pro Thr
1               5                   10                  15

Val Asp Gln Val Asp Asp Thr Ser Ile Val Val Arg Trp Ser Arg Pro
            20                  25                  30

Gln Ala Pro Ile Thr Gly Tyr Arg Ile Val Tyr Ser Pro Ser Val Glu
        35                  40                  45

Gly Ser Ser Thr Glu Leu Asn Leu Pro Glu Thr Ala Asn Ser Val Thr
    50                  55                  60

Leu Ser Asp Leu Gln Pro Gly Val Gln Tyr Asn Ile Thr Ile Tyr Ala
65                  70                  75                  80

Val Glu Glu Asn Gln Glu Ser Thr Pro Val Val Ile Gln Gln Glu Thr
                85                  90                  95

Thr Gly Thr Pro Arg Ser Asp Gly Ser Ser Gly Ser Gly Ser Ser
            100                 105                 110

Pro Thr Asp Leu Arg Phe Thr Asn Ile Gly Pro Asp Thr Met Arg Val
        115                 120                 125

Thr Trp Ala Pro Pro Ser Ile Asp Leu Thr Asn Phe Leu Val Arg
    130                 135                 140

Tyr Ser Pro Val Lys Asn Glu Glu Asp Val Ala Glu Leu Ser Ile Ser
145                 150                 155                 160

Pro Ser Asp Asn Ala Val Val Leu Thr Asn Leu Leu Pro Gly Thr Glu
                165                 170                 175

Tyr Val Val Ser Val Ser Ser Val Tyr Glu Gln His Glu Ser Thr Pro
            180                 185                 190
```

```
Leu Arg Gly Arg Gln Lys Thr Gly Leu Asp Ser Pro Thr Gly Ile Asp
            195                 200                 205

Phe Ser Asp Ile Thr Ala Asn Ser Phe Thr Val His Trp Ile Ala Pro
210                 215                 220

Arg Ala Thr Ile Thr Gly Tyr Arg Ile Arg His His Pro Glu His Phe
225                 230                 235                 240

Ser Gly Arg Pro Arg Glu Asp Arg Val Pro His Ser Arg Asn Ser Ile
                245                 250                 255

Thr Leu Thr Asn Leu Thr Pro Gly Thr Glu Tyr Val Val Ser Ile Val
                260                 265                 270

Ala Leu Asn Gly Arg Glu Glu Ser Pro Leu Leu Ile Gly Gln Gln Ser
            275                 280                 285

Thr Val Ser Asp Val Pro Arg Asp Leu Glu Val Val Ala Ala Thr Pro
290                 295                 300

Thr Ser Leu Leu Ile Ser Trp Asp Ala Pro Ala Val Thr Val Arg Tyr
305                 310                 315                 320

Tyr Arg Ile Thr Tyr Gly Glu Thr Gly Gly Asn Ser Pro Val Gln Glu
                325                 330                 335

Phe Thr Val Pro Gly Ser Lys Ser Thr Ala Thr Ile Ser Gly Leu Lys
                340                 345                 350

Pro Gly Val Asp Tyr Thr Ile Thr Val Tyr Ala Val Thr Gly Arg Gly
                355                 360                 365

Asp Ser Pro Ala Ser Ser Lys Pro Ile Ser Ile Asn Tyr Arg Thr Glu
370                 375                 380

Ile Asp Lys Pro Ser Met Ala Ile Pro Ala Pro Thr Asp Leu Lys Phe
385                 390                 395                 400

Thr Gln Val Thr Pro Thr Ser Leu Ser Ala Gln Trp Thr Pro Pro Asn
                405                 410                 415

Val Gln Leu Thr Gly Tyr Arg Val Arg Val Thr Pro Lys Glu Lys Thr
                420                 425                 430

Gly Pro Met Lys Glu Ile Asn Leu Ala Pro Asp Ser Ser Ser Val Val
            435                 440                 445

Val Ser Gly Leu Met Val Ala Thr Lys Tyr Glu Val Ser Val Tyr Ala
450                 455                 460

Leu Lys Asp Thr Leu Thr Ser Arg Pro Ala Gln Gly Val Val Thr Thr
465                 470                 475                 480

Leu Glu Asn Val Ser Pro Pro Arg Arg Ala Arg Val Thr Asp Ala Thr
                485                 490                 495

Glu Thr Thr Ile Thr Ile Ser Trp Arg Thr Lys Thr Glu Thr Ile Thr
                500                 505                 510

Gly Phe Gln Val Asp Ala Val Pro Ala Asn Gly Gln Thr Pro Ile Gln
            515                 520                 525

Arg Thr Ile Lys Pro Asp Val Arg Ser Tyr Thr Ile Thr Gly Leu Gln
530                 535                 540

Pro Gly Thr Asp Tyr Lys Ile Tyr Leu Tyr Thr Leu Asn Asp Asn Ala
545                 550                 555                 560

Arg Ser Ser Pro Val Val Ile Asp Ala Ser Thr Ala Ile Asp Ala Pro
                565                 570                 575

Ser Asn Leu Arg Phe Leu Ala Thr Thr Pro Asn Ser Leu Leu Val Ser
            580                 585                 590

Trp Gln Pro Pro Arg Ala Arg Ile Thr Gly Tyr Ile Ile Lys Tyr Glu
            595                 600                 605
```

-continued

```
Lys Pro Gly Ser Pro Pro Arg Glu Val Val Pro Arg Pro Gly
    610             615                 620
Val Thr Glu Ala Thr Ile Thr Gly Leu Glu Pro Gly Thr Glu Tyr Thr
625                 630                 635                 640
Ile Tyr Val Ile Ala Leu Lys Asn Asn Gln Lys Ser Glu Pro Leu Ile
                645                 650                 655
Gly Arg Lys Lys Thr Asp Glu Leu Pro Gln Leu Val Thr Leu Pro His
            660                 665                 670
Pro Asn Leu His Gly Pro Glu Ile Leu Asp Val Pro Ser Thr
        675                 680                 685

<210> SEQ ID NO 29
<211> LENGTH: 872
<212> TYPE: PRT
<213> ORGANISM: Artificial Sequence
<220> FEATURE:
<223> OTHER INFORMATION: N-terminal 9a.a. deletion of FCH-296

<400> SEQUENCE: 29

Met Glu Thr Pro Ser Gln Pro Asn Ser His Pro Ile Gln Trp Asn Ala
1               5                   10                  15
Pro Gln Pro Ser His Ile Ser Lys Tyr Ile Leu Arg Trp Arg Pro Lys
            20                  25                  30
Asn Ser Val Gly Arg Trp Lys Glu Ala Thr Ile Pro Gly His Leu Asn
        35                  40                  45
Ser Tyr Thr Ile Lys Gly Leu Lys Pro Gly Val Val Tyr Glu Gly Gln
    50                  55                  60
Leu Ile Ser Ile Gln Gln Tyr Gly His Gln Glu Val Thr Arg Phe Asp
65                  70                  75                  80
Phe Thr Thr Thr Ser Thr Ser Thr Pro Val Thr Ser Asn Thr Val Thr
                85                  90                  95
Gly Glu Thr Thr Pro Phe Ser Pro Leu Val Ala Thr Ser Glu Ser Val
            100                 105                 110
Thr Glu Ile Thr Ala Ser Ser Phe Val Val Ser Trp Val Ser Ala Ser
        115                 120                 125
Asp Thr Val Ser Gly Phe Arg Val Glu Tyr Glu Leu Ser Glu Glu Gly
    130                 135                 140
Asp Glu Pro Gln Tyr Leu Asp Leu Pro Ser Thr Ala Thr Ser Val Asn
145                 150                 155                 160
Ile Pro Asp Leu Leu Pro Gly Arg Lys Tyr Ile Val Asn Val Tyr Gln
                165                 170                 175
Ile Ser Glu Asp Gly Glu Gln Ser Leu Ile Leu Ser Thr Ser Gln Thr
            180                 185                 190
Thr Ala Pro Asp Ala Pro Pro Asp Pro Thr Val Asp Gln Val Asp Asp
        195                 200                 205
Thr Ser Ile Val Val Arg Trp Ser Arg Pro Gln Ala Pro Ile Thr Gly
    210                 215                 220
Tyr Arg Ile Val Tyr Ser Pro Ser Val Glu Gly Ser Ser Thr Glu Leu
225                 230                 235                 240
Asn Leu Pro Glu Thr Ala Asn Ser Val Thr Leu Ser Asp Leu Gln Pro
                245                 250                 255
Gly Val Gln Tyr Asn Ile Thr Ile Tyr Ala Val Glu Glu Asn Gln Glu
            260                 265                 270
Ser Thr Pro Val Val Ile Gln Gln Glu Thr Thr Gly Thr Pro Arg Ser
        275                 280                 285
```

-continued

Asp Gly Ser Ser Gly Ser Ser Gly Ser Ser Pro Thr Asp Leu Arg Phe
290                 295                 300

Thr Asn Ile Gly Pro Asp Thr Met Arg Val Thr Trp Ala Pro Pro Pro
305                 310                 315                 320

Ser Ile Asp Leu Thr Asn Phe Leu Val Arg Tyr Ser Pro Val Lys Asn
            325                 330                 335

Glu Glu Asp Val Ala Glu Leu Ser Ile Ser Pro Ser Asp Asn Ala Val
        340                 345                 350

Val Leu Thr Asn Leu Leu Pro Gly Thr Glu Tyr Val Val Ser Val Ser
    355                 360                 365

Ser Val Tyr Glu Gln His Glu Ser Thr Pro Leu Arg Gly Arg Gln Lys
370                 375                 380

Thr Gly Leu Asp Ser Pro Thr Gly Ile Asp Phe Ser Asp Ile Thr Ala
385                 390                 395                 400

Asn Ser Phe Thr Val His Trp Ile Ala Pro Arg Ala Thr Ile Thr Gly
            405                 410                 415

Tyr Arg Ile Arg His His Pro Glu His Phe Ser Gly Arg Pro Arg Glu
        420                 425                 430

Asp Arg Val Pro His Ser Arg Asn Ser Ile Thr Leu Thr Asn Leu Thr
    435                 440                 445

Pro Gly Thr Glu Tyr Val Val Ser Ile Val Ala Leu Asn Gly Arg Glu
450                 455                 460

Glu Ser Pro Leu Leu Ile Gly Gln Gln Ser Thr Val Ser Asp Val Pro
465                 470                 475                 480

Arg Asp Leu Glu Val Val Ala Ala Thr Pro Thr Ser Leu Leu Ile Ser
            485                 490                 495

Trp Asp Ala Pro Ala Val Thr Val Arg Tyr Tyr Arg Ile Thr Tyr Gly
        500                 505                 510

Glu Thr Gly Gly Asn Ser Pro Val Gln Glu Phe Thr Val Pro Gly Ser
    515                 520                 525

Lys Ser Thr Ala Thr Ile Ser Gly Leu Lys Pro Gly Val Asp Tyr Thr
530                 535                 540

Ile Thr Val Tyr Ala Val Thr Gly Arg Gly Asp Ser Pro Ala Ser Ser
545                 550                 555                 560

Lys Pro Ile Ser Ile Asn Tyr Arg Thr Glu Ile Asp Lys Pro Ser Met
            565                 570                 575

Ala Ile Pro Ala Pro Thr Asp Leu Lys Phe Thr Gln Val Thr Pro Thr
        580                 585                 590

Ser Leu Ser Ala Gln Trp Thr Pro Pro Asn Val Gln Leu Thr Gly Tyr
    595                 600                 605

Arg Val Arg Val Thr Pro Lys Glu Lys Thr Gly Pro Met Lys Glu Ile
610                 615                 620

Asn Leu Ala Pro Asp Ser Ser Val Val Ser Gly Leu Met Val
625                 630                 635                 640

Ala Thr Lys Tyr Glu Val Ser Val Tyr Ala Leu Lys Asp Thr Leu Thr
            645                 650                 655

Ser Arg Pro Ala Gln Gly Val Val Thr Thr Leu Glu Asn Val Ser Pro
        660                 665                 670

Pro Arg Arg Ala Arg Val Thr Asp Ala Thr Glu Thr Thr Ile Thr Ile
    675                 680                 685

Ser Trp Arg Thr Lys Thr Glu Thr Ile Thr Gly Phe Gln Val Asp Ala
690                 695                 700

Val Pro Ala Asn Gly Gln Thr Pro Ile Gln Arg Thr Ile Lys Pro Asp

```
                705                 710                 715                 720
Val Arg Ser Tyr Thr Ile Thr Gly Leu Gln Pro Gly Thr Asp Tyr Lys
                    725                 730                 735
Ile Tyr Leu Tyr Thr Leu Asn Asp Asn Ala Arg Ser Ser Pro Val Val
                    740                 745                 750
Ile Asp Ala Ser Thr Ala Ile Asp Ala Pro Ser Asn Leu Arg Phe Leu
                    755                 760                 765
Ala Thr Thr Pro Asn Ser Leu Leu Val Ser Trp Gln Pro Pro Arg Ala
                    770                 775                 780
Arg Ile Thr Gly Tyr Ile Ile Lys Tyr Glu Lys Pro Gly Ser Pro Pro
785                 790                 795                 800
Arg Glu Val Val Pro Arg Pro Arg Pro Gly Val Thr Glu Ala Thr Ile
                    805                 810                 815
Thr Gly Leu Glu Pro Gly Thr Glu Tyr Thr Ile Tyr Val Ile Ala Leu
                    820                 825                 830
Lys Asn Asn Gln Lys Ser Glu Pro Leu Ile Gly Arg Lys Lys Thr Asp
                    835                 840                 845
Glu Leu Pro Gln Leu Val Thr Leu Pro His Pro Asn Leu His Gly Pro
                    850                 855                 860
Glu Ile Leu Asp Val Pro Ser Thr
865                 870

<210> SEQ ID NO 30
<211> LENGTH: 875
<212> TYPE: PRT
<213> ORGANISM: Artificial Sequence
<220> FEATURE:
<223> OTHER INFORMATION: N-terminal 6a.a. deletion of FCH-296

<400> SEQUENCE: 30

Met Phe Ile Thr Glu Thr Pro Ser Gln Pro Asn Ser His Pro Ile Gln
1               5                   10                  15
Trp Asn Ala Pro Gln Pro Ser His Ile Ser Lys Tyr Ile Leu Arg Trp
                20                  25                  30
Arg Pro Lys Asn Ser Val Gly Arg Trp Lys Glu Ala Thr Ile Pro Gly
                35                  40                  45
His Leu Asn Ser Tyr Thr Ile Lys Gly Leu Lys Pro Gly Val Val Tyr
                50                  55                  60
Glu Gly Gln Leu Ile Ser Ile Gln Gln Tyr Gly His Gln Glu Val Thr
65                  70                  75                  80
Arg Phe Asp Phe Thr Thr Thr Ser Thr Ser Thr Pro Val Thr Ser Asn
                    85                  90                  95
Thr Val Thr Gly Glu Thr Thr Pro Phe Ser Pro Leu Val Ala Thr Ser
                    100                 105                 110
Glu Ser Val Thr Glu Ile Thr Ala Ser Ser Phe Val Val Ser Trp Val
                    115                 120                 125
Ser Ala Ser Asp Thr Val Ser Gly Phe Arg Val Glu Tyr Glu Leu Ser
                    130                 135                 140
Glu Glu Gly Asp Glu Pro Gln Tyr Leu Asp Leu Pro Ser Thr Ala Thr
145                 150                 155                 160
Ser Val Asn Ile Pro Asp Leu Leu Pro Gly Arg Lys Tyr Ile Val Asn
                    165                 170                 175
Val Tyr Gln Ile Ser Glu Asp Gly Glu Gln Ser Leu Ile Leu Ser Thr
                    180                 185                 190
Ser Gln Thr Thr Ala Pro Asp Ala Pro Pro Asp Pro Thr Val Asp Gln
```

```
                195                 200                 205
Val Asp Asp Thr Ser Ile Val Val Arg Trp Ser Arg Pro Gln Ala Pro
210                 215                 220

Ile Thr Gly Tyr Arg Ile Val Tyr Ser Pro Ser Val Glu Gly Ser Ser
225                 230                 235                 240

Thr Glu Leu Asn Leu Pro Glu Thr Ala Asn Ser Val Thr Leu Ser Asp
                245                 250                 255

Leu Gln Pro Gly Val Gln Tyr Asn Ile Thr Ile Tyr Ala Val Glu Glu
            260                 265                 270

Asn Gln Glu Ser Thr Pro Val Val Ile Gln Gln Glu Thr Thr Gly Thr
        275                 280                 285

Pro Arg Ser Asp Gly Ser Ser Gly Ser Ser Gly Ser Ser Pro Thr Asp
290                 295                 300

Leu Arg Phe Thr Asn Ile Gly Pro Asp Thr Met Arg Val Thr Trp Ala
305                 310                 315                 320

Pro Pro Pro Ser Ile Asp Leu Thr Asn Phe Leu Val Arg Tyr Ser Pro
                325                 330                 335

Val Lys Asn Glu Glu Asp Val Ala Glu Leu Ser Ile Ser Pro Ser Asp
            340                 345                 350

Asn Ala Val Val Leu Thr Asn Leu Leu Pro Gly Thr Glu Tyr Val Val
        355                 360                 365

Ser Val Ser Ser Val Tyr Glu Gln His Glu Ser Thr Pro Leu Arg Gly
370                 375                 380

Arg Gln Lys Thr Gly Leu Asp Ser Pro Thr Gly Ile Asp Phe Ser Asp
385                 390                 395                 400

Ile Thr Ala Asn Ser Phe Thr Val His Trp Ile Ala Pro Arg Ala Thr
                405                 410                 415

Ile Thr Gly Tyr Arg Ile Arg His His Pro Glu His Phe Ser Gly Arg
            420                 425                 430

Pro Arg Glu Asp Arg Val Pro His Ser Arg Asn Ser Ile Thr Leu Thr
        435                 440                 445

Asn Leu Thr Pro Gly Thr Glu Tyr Val Val Ser Ile Val Ala Leu Asn
450                 455                 460

Gly Arg Glu Glu Ser Pro Leu Leu Ile Gly Gln Gln Ser Thr Val Ser
465                 470                 475                 480

Asp Val Pro Arg Asp Leu Glu Val Val Ala Ala Thr Pro Thr Ser Leu
                485                 490                 495

Leu Ile Ser Trp Asp Ala Pro Ala Val Thr Val Arg Tyr Tyr Arg Ile
            500                 505                 510

Thr Tyr Gly Glu Thr Gly Gly Asn Ser Pro Val Gln Glu Phe Thr Val
        515                 520                 525

Pro Gly Ser Lys Ser Thr Ala Thr Ile Ser Gly Leu Lys Pro Gly Val
530                 535                 540

Asp Tyr Thr Ile Thr Val Tyr Ala Val Thr Gly Arg Gly Asp Ser Pro
545                 550                 555                 560

Ala Ser Ser Lys Pro Ile Ser Ile Asn Tyr Arg Thr Glu Ile Asp Lys
                565                 570                 575

Pro Ser Met Ala Ile Pro Ala Pro Thr Asp Leu Lys Phe Thr Gln Val
            580                 585                 590

Thr Pro Thr Ser Leu Ser Ala Gln Trp Thr Pro Pro Asn Val Gln Leu
        595                 600                 605

Thr Gly Tyr Arg Val Arg Val Thr Pro Lys Glu Lys Thr Gly Pro Met
610                 615                 620
```

-continued

Lys Glu Ile Asn Leu Ala Pro Asp Ser Ser Val Val Ser Gly
625                 630                 635                 640

Leu Met Val Ala Thr Lys Tyr Glu Val Ser Val Tyr Ala Leu Lys Asp
            645                 650                 655

Thr Leu Thr Ser Arg Pro Ala Gln Gly Val Val Thr Thr Leu Glu Asn
            660                 665                 670

Val Ser Pro Arg Arg Ala Arg Val Thr Asp Ala Thr Glu Thr Thr
        675                 680                 685

Ile Thr Ile Ser Trp Arg Thr Lys Thr Glu Thr Ile Thr Gly Phe Gln
        690                 695                 700

Val Asp Ala Val Pro Ala Asn Gly Gln Thr Pro Ile Gln Arg Thr Ile
705                 710                 715                 720

Lys Pro Asp Val Arg Ser Tyr Thr Ile Thr Gly Leu Gln Pro Gly Thr
            725                 730                 735

Asp Tyr Lys Ile Tyr Leu Tyr Thr Leu Asn Asp Asn Ala Arg Ser Ser
            740                 745                 750

Pro Val Val Ile Asp Ala Ser Thr Ala Ile Asp Ala Pro Ser Asn Leu
        755                 760                 765

Arg Phe Leu Ala Thr Thr Pro Asn Ser Leu Leu Val Ser Trp Gln Pro
770                 775                 780

Pro Arg Ala Arg Ile Thr Gly Tyr Ile Ile Lys Tyr Glu Lys Pro Gly
785                 790                 795                 800

Ser Pro Pro Arg Glu Val Val Pro Arg Pro Arg Gly Val Thr Glu
            805                 810                 815

Ala Thr Ile Thr Gly Leu Glu Pro Gly Thr Glu Tyr Thr Ile Tyr Val
            820                 825                 830

Ile Ala Leu Lys Asn Asn Gln Lys Ser Glu Pro Leu Ile Gly Arg Lys
        835                 840                 845

Lys Thr Asp Glu Leu Pro Gln Leu Val Thr Leu Pro His Pro Asn Leu
        850                 855                 860

His Gly Pro Glu Ile Leu Asp Val Pro Ser Thr
865                 870                 875

<210> SEQ ID NO 31
<211> LENGTH: 876
<212> TYPE: PRT
<213> ORGANISM: Artificial Sequence
<220> FEATURE:
<223> OTHER INFORMATION: N-terminal 5a.a. deletion of FCH-296

<400> SEQUENCE: 31

Met Val Phe Ile Thr Glu Thr Pro Ser Gln Pro Asn Ser His Pro Ile
1               5                   10                  15

Gln Trp Asn Ala Pro Gln Pro Ser His Ile Ser Lys Tyr Ile Leu Arg
            20                  25                  30

Trp Arg Pro Lys Asn Ser Val Gly Arg Trp Lys Glu Ala Thr Ile Pro
        35                  40                  45

Gly His Leu Asn Ser Tyr Thr Ile Lys Gly Leu Lys Pro Gly Val Val
    50                  55                  60

Tyr Glu Gly Gln Leu Ile Ser Ile Gln Gln Tyr Gly His Gln Glu Val
65              70                  75                  80

Thr Arg Phe Asp Phe Thr Thr Ser Thr Ser Thr Pro Val Thr Ser
            85                  90                  95

Asn Thr Val Thr Gly Glu Thr Thr Pro Phe Ser Pro Leu Val Ala Thr
            100                 105                 110

```
Ser Glu Ser Val Thr Glu Ile Thr Ala Ser Ser Phe Val Ser Trp
            115                 120                 125

Val Ser Ala Ser Asp Thr Val Ser Gly Phe Arg Val Glu Tyr Glu Leu
130                 135                 140

Ser Glu Glu Gly Asp Glu Pro Gln Tyr Leu Asp Leu Pro Ser Thr Ala
145                 150                 155                 160

Thr Ser Val Asn Ile Pro Asp Leu Leu Pro Gly Arg Lys Tyr Ile Val
            165                 170                 175

Asn Val Tyr Gln Ile Ser Glu Asp Gly Glu Gln Ser Leu Ile Leu Ser
            180                 185                 190

Thr Ser Gln Thr Thr Ala Pro Asp Ala Pro Pro Asp Pro Thr Val Asp
            195                 200                 205

Gln Val Asp Asp Thr Ser Ile Val Val Arg Trp Ser Arg Pro Gln Ala
210                 215                 220

Pro Ile Thr Gly Tyr Arg Ile Val Tyr Ser Pro Ser Val Glu Gly Ser
225                 230                 235                 240

Ser Thr Glu Leu Asn Leu Pro Glu Thr Ala Asn Ser Val Thr Leu Ser
            245                 250                 255

Asp Leu Gln Pro Gly Val Gln Tyr Asn Ile Thr Ile Tyr Ala Val Glu
            260                 265                 270

Glu Asn Gln Glu Ser Thr Pro Val Val Ile Gln Gln Glu Thr Thr Gly
            275                 280                 285

Thr Pro Arg Ser Asp Gly Ser Ser Gly Ser Ser Pro Thr
            290                 295                 300

Asp Leu Arg Phe Thr Asn Ile Gly Pro Asp Thr Met Arg Val Thr Trp
305                 310                 315                 320

Ala Pro Pro Ser Ile Asp Leu Thr Asn Phe Leu Val Arg Tyr Ser
            325                 330                 335

Pro Val Lys Asn Glu Glu Asp Val Ala Glu Leu Ser Ile Ser Pro Ser
            340                 345                 350

Asp Asn Ala Val Val Leu Thr Asn Leu Leu Pro Gly Thr Glu Tyr Val
            355                 360                 365

Val Ser Val Ser Ser Val Tyr Glu Gln His Glu Ser Thr Pro Leu Arg
370                 375                 380

Gly Arg Gln Lys Thr Gly Leu Asp Ser Pro Thr Gly Ile Asp Phe Ser
385                 390                 395                 400

Asp Ile Thr Ala Asn Ser Phe Thr Val His Trp Ile Ala Pro Arg Ala
            405                 410                 415

Thr Ile Thr Gly Tyr Arg Ile Arg His His Pro Glu His Phe Ser Gly
            420                 425                 430

Arg Pro Arg Glu Asp Arg Val Pro His Ser Arg Asn Ser Ile Thr Leu
            435                 440                 445

Thr Asn Leu Thr Pro Gly Thr Glu Tyr Val Val Ser Ile Val Ala Leu
450                 455                 460

Asn Gly Arg Glu Glu Ser Pro Leu Leu Ile Gly Gln Gln Ser Thr Val
465                 470                 475                 480

Ser Asp Val Pro Arg Asp Leu Glu Val Val Ala Ala Thr Pro Thr Ser
            485                 490                 495

Leu Leu Ile Ser Trp Asp Ala Pro Ala Val Thr Val Arg Tyr Tyr Arg
            500                 505                 510

Ile Thr Tyr Gly Glu Thr Gly Gly Asn Ser Pro Val Gln Glu Phe Thr
            515                 520                 525
```

```
Val Pro Gly Ser Lys Ser Thr Ala Thr Ile Ser Gly Leu Lys Pro Gly
    530                 535                 540

Val Asp Tyr Thr Ile Thr Val Tyr Ala Val Thr Gly Arg Gly Asp Ser
545                 550                 555                 560

Pro Ala Ser Ser Lys Pro Ile Ser Ile Asn Tyr Arg Thr Glu Ile Asp
                565                 570                 575

Lys Pro Ser Met Ala Ile Pro Ala Pro Thr Asp Leu Lys Phe Thr Gln
                580                 585                 590

Val Thr Pro Thr Ser Leu Ser Ala Gln Trp Thr Pro Asn Val Gln
                595                 600                 605

Leu Thr Gly Tyr Arg Val Arg Val Thr Pro Lys Glu Lys Thr Gly Pro
    610                 615                 620

Met Lys Glu Ile Asn Leu Ala Pro Asp Ser Ser Val Val Ser
625                 630                 635                 640

Gly Leu Met Val Ala Thr Lys Tyr Glu Val Ser Val Tyr Ala Leu Lys
                645                 650                 655

Asp Thr Leu Thr Ser Arg Pro Ala Gln Gly Val Val Thr Leu Glu
                660                 665                 670

Asn Val Ser Pro Pro Arg Arg Ala Arg Val Thr Asp Ala Thr Glu Thr
                675                 680                 685

Thr Ile Thr Ile Ser Trp Arg Thr Lys Thr Glu Thr Ile Thr Gly Phe
    690                 695                 700

Gln Val Asp Ala Val Pro Ala Asn Gly Gln Thr Pro Ile Gln Arg Thr
705                 710                 715                 720

Ile Lys Pro Asp Val Arg Ser Tyr Thr Ile Thr Gly Leu Gln Pro Gly
                725                 730                 735

Thr Asp Tyr Lys Ile Tyr Leu Tyr Thr Leu Asn Asp Asn Ala Arg Ser
                740                 745                 750

Ser Pro Val Val Ile Asp Ala Ser Thr Ala Ile Asp Ala Pro Ser Asn
                755                 760                 765

Leu Arg Phe Leu Ala Thr Thr Pro Asn Ser Leu Leu Val Ser Trp Gln
    770                 775                 780

Pro Pro Arg Ala Arg Ile Thr Gly Tyr Ile Ile Lys Tyr Glu Lys Pro
785                 790                 795                 800

Gly Ser Pro Pro Arg Glu Val Val Pro Arg Pro Arg Pro Gly Val Thr
                805                 810                 815

Glu Ala Thr Ile Thr Gly Leu Glu Pro Gly Thr Glu Tyr Thr Ile Tyr
                820                 825                 830

Val Ile Ala Leu Lys Asn Asn Gln Lys Ser Glu Pro Leu Ile Gly Arg
                835                 840                 845

Lys Lys Thr Asp Glu Leu Pro Gln Leu Val Thr Leu Pro His Pro Asn
    850                 855                 860

Leu His Gly Pro Glu Ile Leu Asp Val Pro Ser Thr
865                 870                 875

<210> SEQ ID NO 32
<211> LENGTH: 878
<212> TYPE: PRT
<213> ORGANISM: Artificial Sequence
<220> FEATURE:
<223> OTHER INFORMATION: N-terminal 3a.a. deletion of FCH-296

<400> SEQUENCE: 32

Met Val Glu Val Phe Ile Thr Glu Thr Pro Ser Gln Pro Asn Ser His
1               5                   10                  15
```

```
Pro Ile Gln Trp Asn Ala Pro Gln Pro Ser His Ile Ser Lys Tyr Ile
                20                  25                  30

Leu Arg Trp Arg Pro Lys Asn Ser Val Gly Arg Trp Lys Glu Ala Thr
            35                  40                  45

Ile Pro Gly His Leu Asn Ser Tyr Thr Ile Lys Gly Leu Lys Pro Gly
        50                  55                  60

Val Val Tyr Glu Gly Gln Leu Ile Ser Ile Gln Gln Tyr Gly His Gln
 65                  70                  75                  80

Glu Val Thr Arg Phe Asp Phe Thr Thr Thr Ser Thr Ser Thr Pro Val
                85                  90                  95

Thr Ser Asn Thr Val Thr Gly Glu Thr Thr Pro Phe Ser Pro Leu Val
            100                 105                 110

Ala Thr Ser Glu Ser Val Thr Glu Ile Thr Ala Ser Ser Phe Val Val
        115                 120                 125

Ser Trp Val Ser Ala Ser Asp Thr Val Ser Gly Phe Arg Val Glu Tyr
130                 135                 140

Glu Leu Ser Glu Glu Gly Asp Glu Pro Gln Tyr Leu Asp Leu Pro Ser
145                 150                 155                 160

Thr Ala Thr Ser Val Asn Ile Pro Asp Leu Leu Pro Gly Arg Lys Tyr
                165                 170                 175

Ile Val Asn Val Tyr Gln Ile Ser Glu Asp Gly Glu Gln Ser Leu Ile
            180                 185                 190

Leu Ser Thr Ser Gln Thr Thr Ala Pro Asp Ala Pro Pro Asp Pro Thr
        195                 200                 205

Val Asp Gln Val Asp Asp Thr Ser Ile Val Val Arg Trp Ser Arg Pro
210                 215                 220

Gln Ala Pro Ile Thr Gly Tyr Arg Ile Val Tyr Ser Pro Ser Val Glu
225                 230                 235                 240

Gly Ser Ser Thr Glu Leu Asn Leu Pro Glu Thr Ala Asn Ser Val Thr
                245                 250                 255

Leu Ser Asp Leu Gln Pro Gly Val Gln Tyr Asn Ile Thr Ile Tyr Ala
            260                 265                 270

Val Glu Glu Asn Gln Glu Ser Thr Pro Val Val Ile Gln Gln Glu Thr
        275                 280                 285

Thr Gly Thr Pro Arg Ser Asp Gly Ser Ser Gly Ser Ser Gly Ser Ser
290                 295                 300

Pro Thr Asp Leu Arg Phe Thr Asn Ile Gly Pro Asp Thr Met Arg Val
305                 310                 315                 320

Thr Trp Ala Pro Pro Ser Ile Asp Leu Thr Asn Phe Leu Val Arg
                325                 330                 335

Tyr Ser Pro Val Lys Asn Glu Glu Asp Val Ala Glu Leu Ser Ile Ser
            340                 345                 350

Pro Ser Asp Asn Ala Val Val Leu Thr Asn Leu Leu Pro Gly Thr Glu
        355                 360                 365

Tyr Val Val Ser Val Ser Ser Val Tyr Glu Gln His Glu Ser Thr Pro
370                 375                 380

Leu Arg Gly Arg Gln Lys Thr Gly Leu Asp Ser Pro Thr Gly Ile Asp
385                 390                 395                 400

Phe Ser Asp Ile Thr Ala Asn Ser Phe Thr Val His Trp Ile Ala Pro
                405                 410                 415

Arg Ala Thr Ile Thr Gly Tyr Arg Ile Arg His His Pro Glu His Phe
            420                 425                 430

Ser Gly Arg Pro Arg Glu Asp Arg Val Pro His Ser Arg Asn Ser Ile
```

```
                    435                 440                 445
Thr Leu Thr Asn Leu Thr Pro Gly Thr Glu Tyr Val Val Ser Ile Val
    450                 455                 460

Ala Leu Asn Gly Arg Glu Glu Ser Pro Leu Leu Ile Gly Gln Gln Ser
465                 470                 475                 480

Thr Val Ser Asp Val Pro Arg Asp Leu Glu Val Val Ala Ala Thr Pro
                485                 490                 495

Thr Ser Leu Leu Ile Ser Trp Asp Ala Pro Ala Val Thr Val Arg Tyr
                500                 505                 510

Tyr Arg Ile Thr Tyr Gly Glu Thr Gly Gly Asn Ser Pro Val Gln Glu
            515                 520                 525

Phe Thr Val Pro Gly Ser Lys Ser Thr Ala Thr Ile Ser Gly Leu Lys
    530                 535                 540

Pro Gly Val Asp Tyr Thr Ile Thr Val Tyr Ala Val Thr Gly Arg Gly
545                 550                 555                 560

Asp Ser Pro Ala Ser Ser Lys Pro Ile Ser Ile Asn Tyr Arg Thr Glu
                565                 570                 575

Ile Asp Lys Pro Ser Met Ala Ile Pro Ala Pro Thr Asp Leu Lys Phe
                580                 585                 590

Thr Gln Val Thr Pro Thr Ser Leu Ser Ala Gln Trp Thr Pro Pro Asn
            595                 600                 605

Val Gln Leu Thr Gly Tyr Arg Val Arg Val Thr Pro Lys Glu Lys Thr
    610                 615                 620

Gly Pro Met Lys Glu Ile Asn Leu Ala Pro Asp Ser Ser Ser Val Val
625                 630                 635                 640

Val Ser Gly Leu Met Val Ala Thr Lys Tyr Glu Val Ser Val Tyr Ala
                645                 650                 655

Leu Lys Asp Thr Leu Thr Ser Arg Pro Ala Gln Gly Val Val Thr Thr
                660                 665                 670

Leu Glu Asn Val Ser Pro Pro Arg Arg Ala Arg Val Thr Asp Ala Thr
            675                 680                 685

Glu Thr Thr Ile Thr Ile Ser Trp Arg Thr Lys Thr Glu Thr Ile Thr
    690                 695                 700

Gly Phe Gln Val Asp Ala Val Pro Ala Asn Gly Gln Thr Pro Ile Gln
705                 710                 715                 720

Arg Thr Ile Lys Pro Asp Val Arg Ser Tyr Thr Ile Thr Gly Leu Gln
                725                 730                 735

Pro Gly Thr Asp Tyr Lys Ile Tyr Leu Tyr Thr Leu Asn Asp Asn Ala
                740                 745                 750

Arg Ser Ser Pro Val Val Ile Asp Ala Ser Thr Ala Ile Asp Ala Pro
            755                 760                 765

Ser Asn Leu Arg Phe Leu Ala Thr Thr Pro Asn Ser Leu Leu Val Ser
    770                 775                 780

Trp Gln Pro Pro Arg Ala Arg Ile Thr Gly Tyr Ile Ile Lys Tyr Glu
785                 790                 795                 800

Lys Pro Gly Ser Pro Pro Arg Glu Val Val Pro Arg Pro Arg Pro Gly
                805                 810                 815

Val Thr Glu Ala Thr Ile Thr Gly Leu Glu Pro Gly Thr Glu Tyr Thr
                820                 825                 830

Ile Tyr Val Ile Ala Leu Lys Asn Asn Gln Lys Ser Glu Pro Leu Ile
            835                 840                 845

Gly Arg Lys Lys Thr Asp Glu Leu Pro Gln Leu Val Thr Leu Pro His
    850                 855                 860
```

Pro Asn Leu His Gly Pro Glu Ile Leu Asp Val Pro Ser Thr
865                 870                 875

<210> SEQ ID NO 33
<211> LENGTH: 884
<212> TYPE: PRT
<213> ORGANISM: Artificial Sequence
<220> FEATURE:
<223> OTHER INFORMATION: N-terminal 3a.a. insertion of FCH-296

<400> SEQUENCE: 33

Met Pro Ser Ser Ser Gly Pro Val Glu Val Phe Ile Thr Glu Thr Pro
1               5                   10                  15

Ser Gln Pro Asn Ser His Pro Ile Gln Trp Asn Ala Pro Gln Pro Ser
            20                  25                  30

His Ile Ser Lys Tyr Ile Leu Arg Trp Arg Pro Lys Asn Ser Val Gly
        35                  40                  45

Arg Trp Lys Glu Ala Thr Ile Pro Gly His Leu Asn Ser Tyr Thr Ile
    50                  55                  60

Lys Gly Leu Lys Pro Gly Val Val Tyr Glu Gly Gln Leu Ile Ser Ile
65                  70                  75                  80

Gln Gln Tyr Gly His Gln Glu Val Thr Arg Phe Asp Phe Thr Thr Thr
                85                  90                  95

Ser Thr Ser Thr Pro Val Thr Ser Asn Thr Val Thr Gly Glu Thr Thr
            100                 105                 110

Pro Phe Ser Pro Leu Val Ala Thr Ser Glu Ser Val Thr Glu Ile Thr
        115                 120                 125

Ala Ser Ser Phe Val Val Ser Trp Val Ser Ala Ser Asp Thr Val Ser
    130                 135                 140

Gly Phe Arg Val Glu Tyr Glu Leu Ser Glu Gly Asp Glu Pro Gln
145                 150                 155                 160

Tyr Leu Asp Leu Pro Ser Thr Ala Thr Ser Val Asn Ile Pro Asp Leu
                165                 170                 175

Leu Pro Gly Arg Lys Tyr Ile Val Asn Val Tyr Gln Ile Ser Glu Asp
            180                 185                 190

Gly Glu Gln Ser Leu Ile Leu Ser Thr Ser Gln Thr Thr Ala Pro Asp
        195                 200                 205

Ala Pro Pro Asp Pro Thr Val Asp Gln Val Asp Asp Thr Ser Ile Val
    210                 215                 220

Val Arg Trp Ser Arg Pro Gln Ala Pro Ile Thr Gly Tyr Arg Ile Val
225                 230                 235                 240

Tyr Ser Pro Ser Val Glu Gly Ser Ser Thr Glu Leu Asn Leu Pro Glu
                245                 250                 255

Thr Ala Asn Ser Val Thr Leu Ser Asp Leu Gln Pro Gly Val Gln Tyr
            260                 265                 270

Asn Ile Thr Ile Tyr Ala Val Glu Glu Asn Gln Glu Ser Thr Pro Val
        275                 280                 285

Val Ile Gln Gln Glu Thr Thr Gly Thr Pro Arg Ser Asp Gly Ser Ser
    290                 295                 300

Gly Ser Ser Gly Ser Ser Pro Thr Asp Leu Arg Phe Thr Asn Ile Gly
305                 310                 315                 320

Pro Asp Thr Met Arg Val Thr Trp Ala Pro Pro Pro Ser Ile Asp Leu
                325                 330                 335

Thr Asn Phe Leu Val Arg Tyr Ser Pro Val Lys Asn Glu Glu Asp Val
            340                 345                 350

```
Ala Glu Leu Ser Ile Ser Pro Ser Asp Asn Ala Val Val Leu Thr Asn
        355                 360                 365

Leu Leu Pro Gly Thr Glu Tyr Val Val Ser Val Ser Ser Val Tyr Glu
        370                 375                 380

Gln His Glu Ser Thr Pro Leu Arg Gly Arg Gln Lys Thr Gly Leu Asp
385                 390                 395                 400

Ser Pro Thr Gly Ile Asp Phe Ser Asp Ile Thr Ala Asn Ser Phe Thr
                405                 410                 415

Val His Trp Ile Ala Pro Arg Ala Thr Ile Thr Gly Tyr Arg Ile Arg
                420                 425                 430

His His Pro Glu His Phe Ser Gly Arg Pro Arg Glu Asp Arg Val Pro
                435                 440                 445

His Ser Arg Asn Ser Ile Thr Leu Thr Asn Leu Thr Pro Gly Thr Glu
        450                 455                 460

Tyr Val Val Ser Ile Val Ala Leu Asn Gly Arg Glu Glu Ser Pro Leu
465                 470                 475                 480

Leu Ile Gly Gln Gln Ser Thr Val Ser Asp Val Pro Arg Asp Leu Glu
                485                 490                 495

Val Val Ala Ala Thr Pro Thr Ser Leu Leu Ile Ser Trp Asp Ala Pro
                500                 505                 510

Ala Val Thr Val Arg Tyr Tyr Arg Ile Thr Tyr Gly Glu Thr Gly Gly
                515                 520                 525

Asn Ser Pro Val Gln Glu Phe Thr Val Pro Gly Ser Lys Ser Thr Ala
        530                 535                 540

Thr Ile Ser Gly Leu Lys Pro Gly Val Asp Tyr Thr Ile Thr Val Tyr
545                 550                 555                 560

Ala Val Thr Gly Arg Gly Asp Ser Pro Ala Ser Ser Lys Pro Ile Ser
                565                 570                 575

Ile Asn Tyr Arg Thr Glu Ile Asp Lys Pro Ser Met Ala Ile Pro Ala
                580                 585                 590

Pro Thr Asp Leu Lys Phe Thr Gln Val Thr Pro Thr Ser Leu Ser Ala
        595                 600                 605

Gln Trp Thr Pro Pro Asn Val Gln Leu Thr Gly Tyr Arg Val Arg Val
        610                 615                 620

Thr Pro Lys Glu Lys Thr Gly Pro Met Lys Glu Ile Asn Leu Ala Pro
625                 630                 635                 640

Asp Ser Ser Ser Val Val Val Ser Gly Leu Met Val Ala Thr Lys Tyr
                645                 650                 655

Glu Val Ser Val Tyr Ala Leu Lys Asp Thr Leu Thr Ser Arg Pro Ala
                660                 665                 670

Gln Gly Val Val Thr Thr Leu Glu Asn Val Ser Pro Pro Arg Arg Ala
                675                 680                 685

Arg Val Thr Asp Ala Thr Glu Thr Thr Ile Thr Ile Ser Trp Arg Thr
        690                 695                 700

Lys Thr Glu Thr Ile Thr Gly Phe Gln Val Asp Ala Val Pro Ala Asn
705                 710                 715                 720

Gly Gln Thr Pro Ile Gln Arg Thr Ile Lys Pro Asp Val Arg Ser Tyr
                725                 730                 735

Thr Ile Thr Gly Leu Gln Pro Gly Thr Asp Tyr Lys Ile Tyr Leu Tyr
                740                 745                 750

Thr Leu Asn Asp Asn Ala Arg Ser Ser Pro Val Val Ile Asp Ala Ser
        755                 760                 765
```

```
Thr Ala Ile Asp Ala Pro Ser Asn Leu Arg Phe Leu Ala Thr Thr Pro
770                 775                 780

Asn Ser Leu Leu Val Ser Trp Gln Pro Pro Arg Ala Arg Ile Thr Gly
785                 790                 795                 800

Tyr Ile Ile Lys Tyr Glu Lys Pro Gly Ser Pro Pro Arg Glu Val Val
                805                 810                 815

Pro Arg Pro Arg Pro Gly Val Thr Glu Ala Thr Ile Thr Gly Leu Glu
                820                 825                 830

Pro Gly Thr Glu Tyr Thr Ile Tyr Val Ile Ala Leu Lys Asn Asn Gln
                835                 840                 845

Lys Ser Glu Pro Leu Ile Gly Arg Lys Lys Thr Asp Glu Leu Pro Gln
850                 855                 860

Leu Val Thr Leu Pro His Pro Asn Leu His Gly Pro Glu Ile Leu Asp
865                 870                 875                 880

Val Pro Ser Thr

<210> SEQ ID NO 34
<211> LENGTH: 887
<212> TYPE: PRT
<213> ORGANISM: Artificial Sequence
<220> FEATURE:
<223> OTHER INFORMATION: N-terminal 6a.a. insertion of FCH-296

<400> SEQUENCE: 34

Met Gln Thr Tyr Pro Ser Ser Gly Pro Val Glu Val Phe Ile Thr
1               5                   10                  15

Glu Thr Pro Ser Gln Pro Asn Ser His Pro Ile Gln Trp Asn Ala Pro
                20                  25                  30

Gln Pro Ser His Ile Ser Lys Tyr Ile Leu Arg Trp Arg Pro Lys Asn
                35                  40                  45

Ser Val Gly Arg Trp Lys Glu Ala Thr Ile Pro Gly His Leu Asn Ser
50                  55                  60

Tyr Thr Ile Lys Gly Leu Lys Pro Gly Val Val Tyr Glu Gly Gln Leu
65                  70                  75                  80

Ile Ser Ile Gln Gln Tyr Gly His Gln Glu Val Thr Arg Phe Asp Phe
                85                  90                  95

Thr Thr Thr Ser Thr Ser Thr Pro Val Thr Ser Asn Thr Val Thr Gly
                100                 105                 110

Glu Thr Thr Pro Phe Ser Pro Leu Val Ala Thr Ser Glu Ser Val Thr
                115                 120                 125

Glu Ile Thr Ala Ser Ser Phe Val Val Ser Trp Val Ser Ala Ser Asp
                130                 135                 140

Thr Val Ser Gly Phe Arg Val Glu Tyr Glu Leu Ser Glu Glu Gly Asp
145                 150                 155                 160

Glu Pro Gln Tyr Leu Asp Leu Pro Ser Thr Ala Thr Ser Val Asn Ile
                165                 170                 175

Pro Asp Leu Leu Pro Gly Arg Lys Tyr Ile Val Asn Val Tyr Gln Ile
                180                 185                 190

Ser Glu Asp Gly Glu Gln Ser Leu Ile Leu Ser Thr Ser Gln Thr Thr
                195                 200                 205

Ala Pro Asp Ala Pro Pro Asp Pro Thr Val Asp Gln Val Asp Asp Thr
                210                 215                 220

Ser Ile Val Val Arg Trp Ser Arg Pro Gln Ala Pro Ile Thr Gly Tyr
225                 230                 235                 240

Arg Ile Val Tyr Ser Pro Ser Val Glu Gly Ser Ser Thr Glu Leu Asn
```

-continued

```
                245                 250                 255
Leu Pro Glu Thr Ala Asn Ser Val Thr Leu Ser Asp Leu Gln Pro Gly
                260                 265                 270

Val Gln Tyr Asn Ile Thr Ile Tyr Ala Val Glu Glu Asn Gln Glu Ser
                275                 280                 285

Thr Pro Val Val Ile Gln Gln Glu Thr Thr Gly Thr Pro Arg Ser Asp
290                 295                 300

Gly Ser Ser Gly Ser Ser Gly Ser Ser Pro Thr Asp Leu Arg Phe Thr
305                 310                 315                 320

Asn Ile Gly Pro Asp Thr Met Arg Val Thr Trp Ala Pro Pro Ser
                325                 330                 335

Ile Asp Leu Thr Asn Phe Leu Val Arg Tyr Ser Pro Val Lys Asn Glu
                340                 345                 350

Glu Asp Val Ala Glu Leu Ser Ile Ser Pro Ser Asp Asn Ala Val Val
                355                 360                 365

Leu Thr Asn Leu Leu Pro Gly Thr Glu Tyr Val Val Ser Val Ser Ser
                370                 375                 380

Val Tyr Glu Gln His Glu Ser Thr Pro Leu Arg Gly Arg Gln Lys Thr
385                 390                 395                 400

Gly Leu Asp Ser Pro Thr Gly Ile Asp Phe Ser Asp Ile Thr Ala Asn
                405                 410                 415

Ser Phe Thr Val His Trp Ile Ala Pro Arg Ala Thr Ile Thr Gly Tyr
                420                 425                 430

Arg Ile Arg His His Pro Glu His Phe Ser Gly Arg Pro Arg Glu Asp
                435                 440                 445

Arg Val Pro His Ser Arg Asn Ser Ile Thr Leu Thr Asn Leu Thr Pro
450                 455                 460

Gly Thr Glu Tyr Val Val Ser Ile Val Ala Leu Asn Gly Arg Glu Glu
465                 470                 475                 480

Ser Pro Leu Leu Ile Gly Gln Gln Ser Thr Val Ser Asp Val Pro Arg
                485                 490                 495

Asp Leu Glu Val Val Ala Ala Thr Pro Thr Ser Leu Leu Ile Ser Trp
                500                 505                 510

Asp Ala Pro Ala Val Thr Val Arg Tyr Tyr Arg Ile Thr Tyr Gly Glu
                515                 520                 525

Thr Gly Gly Asn Ser Pro Val Gln Glu Phe Thr Val Pro Gly Ser Lys
                530                 535                 540

Ser Thr Ala Thr Ile Ser Gly Leu Lys Pro Gly Val Asp Tyr Thr Ile
545                 550                 555                 560

Thr Val Tyr Ala Val Thr Gly Arg Gly Asp Ser Pro Ala Ser Ser Lys
                565                 570                 575

Pro Ile Ser Ile Asn Tyr Arg Thr Glu Ile Asp Lys Pro Ser Met Ala
                580                 585                 590

Ile Pro Ala Pro Thr Asp Leu Lys Phe Thr Gln Val Thr Pro Thr Ser
                595                 600                 605

Leu Ser Ala Gln Trp Thr Pro Pro Asn Val Gln Leu Thr Gly Tyr Arg
                610                 615                 620

Val Arg Val Thr Pro Lys Glu Lys Thr Gly Pro Met Lys Glu Ile Asn
625                 630                 635                 640

Leu Ala Pro Asp Ser Ser Ser Val Val Ser Gly Leu Met Val Ala
                645                 650                 655

Thr Lys Tyr Glu Val Ser Val Tyr Ala Leu Lys Asp Thr Leu Thr Ser
                660                 665                 670
```

```
Arg Pro Ala Gln Gly Val Val Thr Thr Leu Glu Asn Val Ser Pro Pro
            675                 680                 685

Arg Arg Ala Arg Val Thr Asp Ala Thr Glu Thr Thr Ile Thr Ile Ser
690                 695                 700

Trp Arg Thr Lys Thr Glu Thr Ile Thr Gly Phe Gln Val Asp Ala Val
705                 710                 715                 720

Pro Ala Asn Gly Gln Thr Pro Ile Gln Arg Thr Ile Lys Pro Asp Val
            725                 730                 735

Arg Ser Tyr Thr Ile Thr Gly Leu Gln Pro Gly Thr Asp Tyr Lys Ile
            740                 745                 750

Tyr Leu Tyr Thr Leu Asn Asp Asn Ala Arg Ser Ser Pro Val Val Ile
            755                 760                 765

Asp Ala Ser Thr Ala Ile Asp Ala Pro Ser Asn Leu Arg Phe Leu Ala
            770                 775                 780

Thr Thr Pro Asn Ser Leu Leu Val Ser Trp Gln Pro Pro Arg Ala Arg
785                 790                 795                 800

Ile Thr Gly Tyr Ile Ile Lys Tyr Glu Lys Pro Gly Ser Pro Pro Arg
            805                 810                 815

Glu Val Val Pro Arg Pro Arg Pro Gly Val Thr Glu Ala Thr Ile Thr
            820                 825                 830

Gly Leu Glu Pro Gly Thr Glu Tyr Thr Ile Tyr Val Ile Ala Leu Lys
            835                 840                 845

Asn Asn Gln Lys Ser Glu Pro Leu Ile Gly Arg Lys Lys Thr Asp Glu
            850                 855                 860

Leu Pro Gln Leu Val Thr Leu Pro His Pro Asn Leu His Gly Pro Glu
865                 870                 875                 880

Ile Leu Asp Val Pro Ser Thr
            885

<210> SEQ ID NO 35
<211> LENGTH: 890
<212> TYPE: PRT
<213> ORGANISM: Artificial Sequence
<220> FEATURE:
<223> OTHER INFORMATION: N-terminal 9a.a. insertion of FCH-296

<400> SEQUENCE: 35

Met Gln Pro Leu Gln Thr Tyr Pro Ser Ser Gly Pro Val Glu Val
1               5                   10                  15

Phe Ile Thr Glu Thr Pro Ser Gln Pro Asn Ser His Pro Ile Gln Trp
            20                  25                  30

Asn Ala Pro Gln Pro Ser His Ile Ser Lys Tyr Ile Leu Arg Trp Arg
            35                  40                  45

Pro Lys Asn Ser Val Gly Arg Trp Lys Glu Ala Thr Ile Pro Gly His
            50                  55                  60

Leu Asn Ser Tyr Thr Ile Lys Gly Leu Lys Pro Gly Val Val Tyr Glu
65                  70                  75                  80

Gly Gln Leu Ile Ser Ile Gln Gln Tyr Gly His Gln Glu Val Thr Arg
            85                  90                  95

Phe Asp Phe Thr Thr Thr Ser Ser Thr Pro Val Thr Ser Asn Thr
            100                 105                 110

Val Thr Gly Glu Thr Thr Pro Phe Ser Pro Leu Val Ala Thr Ser Glu
            115                 120                 125

Ser Val Thr Glu Ile Thr Ala Ser Ser Phe Val Val Ser Trp Val Ser
            130                 135                 140
```

-continued

```
Ala Ser Asp Thr Val Ser Gly Phe Arg Val Glu Tyr Glu Leu Ser Glu
145                 150                 155                 160

Glu Gly Asp Glu Pro Gln Tyr Leu Asp Leu Pro Ser Thr Ala Thr Ser
            165                 170                 175

Val Asn Ile Pro Asp Leu Leu Pro Gly Arg Lys Tyr Ile Val Asn Val
        180                 185                 190

Tyr Gln Ile Ser Glu Asp Gly Glu Gln Ser Leu Ile Leu Ser Thr Ser
    195                 200                 205

Gln Thr Thr Ala Pro Asp Ala Pro Pro Asp Pro Thr Val Asp Gln Val
210                 215                 220

Asp Asp Thr Ser Ile Val Val Arg Trp Ser Arg Pro Gln Ala Pro Ile
225                 230                 235                 240

Thr Gly Tyr Arg Ile Val Tyr Ser Pro Ser Val Glu Gly Ser Ser Thr
                245                 250                 255

Glu Leu Asn Leu Pro Glu Thr Ala Asn Ser Val Thr Leu Ser Asp Leu
            260                 265                 270

Gln Pro Gly Val Gln Tyr Asn Ile Thr Ile Tyr Ala Val Glu Glu Asn
        275                 280                 285

Gln Glu Ser Thr Pro Val Val Ile Gln Gln Glu Thr Thr Gly Thr Pro
    290                 295                 300

Arg Ser Asp Gly Ser Ser Gly Ser Ser Gly Ser Ser Pro Thr Asp Leu
305                 310                 315                 320

Arg Phe Thr Asn Ile Gly Pro Asp Thr Met Arg Val Thr Trp Ala Pro
                325                 330                 335

Pro Pro Ser Ile Asp Leu Thr Asn Phe Leu Val Arg Tyr Ser Pro Val
            340                 345                 350

Lys Asn Glu Glu Asp Val Ala Glu Leu Ser Ile Ser Pro Ser Asp Asn
        355                 360                 365

Ala Val Val Leu Thr Asn Leu Leu Pro Gly Thr Glu Tyr Val Val Ser
    370                 375                 380

Val Ser Ser Val Tyr Glu Gln His Glu Ser Thr Pro Leu Arg Gly Arg
385                 390                 395                 400

Gln Lys Thr Gly Leu Asp Ser Pro Thr Gly Ile Asp Phe Ser Asp Ile
                405                 410                 415

Thr Ala Asn Ser Phe Thr Val His Trp Ile Ala Pro Arg Ala Thr Ile
            420                 425                 430

Thr Gly Tyr Arg Ile Arg His His Pro Glu His Phe Ser Gly Arg Pro
        435                 440                 445

Arg Glu Asp Arg Val Pro His Ser Arg Asn Ser Ile Thr Leu Thr Asn
    450                 455                 460

Leu Thr Pro Gly Thr Glu Tyr Val Val Ser Ile Val Ala Leu Asn Gly
465                 470                 475                 480

Arg Glu Glu Ser Pro Leu Leu Ile Gly Gln Gln Ser Thr Val Ser Asp
                485                 490                 495

Val Pro Arg Asp Leu Glu Val Val Ala Ala Thr Pro Thr Ser Leu Leu
            500                 505                 510

Ile Ser Trp Asp Ala Pro Ala Val Thr Val Arg Tyr Tyr Arg Ile Thr
        515                 520                 525

Tyr Gly Glu Thr Gly Gly Asn Ser Pro Val Gln Glu Phe Thr Val Pro
    530                 535                 540

Gly Ser Lys Ser Thr Ala Thr Ile Ser Gly Leu Lys Pro Gly Val Asp
545                 550                 555                 560
```

```
Tyr Thr Ile Thr Val Tyr Ala Val Thr Gly Arg Gly Asp Ser Pro Ala
                565                 570                 575

Ser Ser Lys Pro Ile Ser Ile Asn Tyr Arg Thr Glu Ile Asp Lys Pro
            580                 585                 590

Ser Met Ala Ile Pro Ala Pro Thr Asp Leu Lys Phe Thr Gln Val Thr
        595                 600                 605

Pro Thr Ser Leu Ser Ala Gln Trp Thr Pro Pro Asn Val Gln Leu Thr
    610                 615                 620

Gly Tyr Arg Val Arg Val Thr Pro Lys Glu Lys Thr Gly Pro Met Lys
625                 630                 635                 640

Glu Ile Asn Leu Ala Pro Asp Ser Ser Val Val Val Ser Gly Leu
                645                 650                 655

Met Val Ala Thr Lys Tyr Glu Val Ser Val Tyr Ala Leu Lys Asp Thr
                660                 665                 670

Leu Thr Ser Arg Pro Ala Gln Gly Val Val Thr Thr Leu Glu Asn Val
            675                 680                 685

Ser Pro Pro Arg Arg Ala Arg Val Thr Asp Ala Thr Glu Thr Thr Ile
        690                 695                 700

Thr Ile Ser Trp Arg Thr Lys Thr Glu Thr Ile Thr Gly Phe Gln Val
705                 710                 715                 720

Asp Ala Val Pro Ala Asn Gly Gln Thr Pro Ile Gln Arg Thr Ile Lys
                725                 730                 735

Pro Asp Val Arg Ser Tyr Thr Ile Thr Gly Leu Gln Pro Gly Thr Asp
            740                 745                 750

Tyr Lys Ile Tyr Leu Tyr Thr Leu Asn Asp Asn Ala Arg Ser Ser Pro
        755                 760                 765

Val Val Ile Asp Ala Ser Thr Ala Ile Asp Ala Pro Ser Asn Leu Arg
    770                 775                 780

Phe Leu Ala Thr Thr Pro Asn Ser Leu Leu Val Ser Trp Gln Pro Pro
785                 790                 795                 800

Arg Ala Arg Ile Thr Gly Tyr Ile Ile Lys Tyr Glu Lys Pro Gly Ser
                805                 810                 815

Pro Pro Arg Glu Val Val Pro Arg Pro Arg Pro Gly Val Thr Glu Ala
            820                 825                 830

Thr Ile Thr Gly Leu Glu Pro Gly Thr Glu Tyr Thr Ile Tyr Val Ile
        835                 840                 845

Ala Leu Lys Asn Asn Gln Lys Ser Glu Pro Leu Ile Gly Arg Lys Lys
    850                 855                 860

Thr Asp Glu Leu Pro Gln Leu Val Thr Leu Pro His Pro Asn Leu His
865                 870                 875                 880

Gly Pro Glu Ile Leu Asp Val Pro Ser Thr
                885                 890

<210> SEQ ID NO 36
<211> LENGTH: 892
<212> TYPE: PRT
<213> ORGANISM: Artificial Sequence
<220> FEATURE:
<223> OTHER INFORMATION: N-terminal 11a.a. insertion of FCH-296

<400> SEQUENCE: 36

Met His Cys Gln Pro Leu Gln Thr Tyr Pro Ser Ser Gly Pro Val
1               5                   10                  15

Glu Val Phe Ile Thr Glu Thr Pro Ser Gln Pro Asn Ser His Pro Ile
                20                  25                  30
```

```
Gln Trp Asn Ala Pro Gln Pro Ser His Ile Ser Lys Tyr Ile Leu Arg
             35                  40                  45

Trp Arg Pro Lys Asn Ser Val Gly Arg Trp Lys Glu Ala Thr Ile Pro
 50                  55                  60

Gly His Leu Asn Ser Tyr Thr Ile Lys Gly Lys Pro Gly Val Val
 65                  70                  75                  80

Tyr Glu Gly Gln Leu Ile Ser Ile Gln Gln Tyr Gly His Gln Glu Val
                 85                  90                  95

Thr Arg Phe Asp Phe Thr Thr Thr Ser Thr Ser Thr Pro Val Thr Ser
            100                 105                 110

Asn Thr Val Thr Gly Glu Thr Thr Pro Phe Ser Pro Leu Val Ala Thr
                115                 120                 125

Ser Glu Ser Val Thr Glu Ile Thr Ala Ser Ser Phe Val Val Ser Trp
130                 135                 140

Val Ser Ala Ser Asp Thr Val Ser Gly Phe Arg Val Glu Tyr Glu Leu
145                 150                 155                 160

Ser Glu Glu Gly Asp Glu Pro Gln Tyr Leu Asp Leu Pro Ser Thr Ala
                165                 170                 175

Thr Ser Val Asn Ile Pro Asp Leu Leu Pro Gly Arg Lys Tyr Ile Val
                180                 185                 190

Asn Val Tyr Gln Ile Ser Glu Asp Gly Glu Gln Ser Leu Ile Leu Ser
                195                 200                 205

Thr Ser Gln Thr Thr Ala Pro Asp Ala Pro Pro Asp Pro Thr Val Asp
210                 215                 220

Gln Val Asp Asp Thr Ser Ile Val Val Arg Trp Ser Arg Pro Gln Ala
225                 230                 235                 240

Pro Ile Thr Gly Tyr Arg Ile Val Tyr Ser Pro Ser Val Glu Gly Ser
                245                 250                 255

Ser Thr Glu Leu Asn Leu Pro Glu Thr Ala Asn Ser Val Thr Leu Ser
                260                 265                 270

Asp Leu Gln Pro Gly Val Gln Tyr Asn Ile Thr Ile Tyr Ala Val Glu
                275                 280                 285

Glu Asn Gln Glu Ser Thr Pro Val Val Ile Gln Gln Glu Thr Thr Gly
            290                 295                 300

Thr Pro Arg Ser Asp Gly Ser Ser Gly Ser Ser Gly Ser Ser Pro Thr
305                 310                 315                 320

Asp Leu Arg Phe Thr Asn Ile Gly Pro Asp Thr Met Arg Val Thr Trp
                325                 330                 335

Ala Pro Pro Pro Ser Ile Asp Leu Thr Asn Phe Leu Val Arg Tyr Ser
            340                 345                 350

Pro Val Lys Asn Glu Glu Asp Val Ala Glu Leu Ser Ile Ser Pro Ser
            355                 360                 365

Asp Asn Ala Val Val Leu Thr Asn Leu Leu Pro Gly Thr Glu Tyr Val
            370                 375                 380

Val Ser Val Ser Ser Val Tyr Glu Gln His Glu Ser Thr Pro Leu Arg
385                 390                 395                 400

Gly Arg Gln Lys Thr Gly Leu Asp Ser Pro Thr Gly Ile Asp Phe Ser
                405                 410                 415

Asp Ile Thr Ala Asn Ser Phe Thr Val His Trp Ile Ala Pro Arg Ala
            420                 425                 430

Thr Ile Thr Gly Tyr Arg Ile Arg His His Pro Glu His Phe Ser Gly
            435                 440                 445

Arg Pro Arg Glu Asp Arg Val Pro His Ser Arg Asn Ser Ile Thr Leu
```

```
                450             455             460
Thr Asn Leu Thr Pro Gly Thr Glu Tyr Val Val Ser Ile Val Ala Leu
465                 470                 475                 480

Asn Gly Arg Glu Glu Ser Pro Leu Leu Ile Gly Gln Gln Ser Thr Val
                    485                 490                 495

Ser Asp Val Pro Arg Asp Leu Glu Val Val Ala Ala Thr Pro Thr Ser
                500                 505                 510

Leu Leu Ile Ser Trp Asp Ala Pro Ala Val Thr Val Arg Tyr Tyr Arg
                515                 520                 525

Ile Thr Tyr Gly Glu Thr Gly Gly Asn Ser Pro Val Gln Glu Phe Thr
            530                 535                 540

Val Pro Gly Ser Lys Ser Thr Ala Thr Ile Ser Gly Leu Lys Pro Gly
545                 550                 555                 560

Val Asp Tyr Thr Ile Thr Val Tyr Ala Val Thr Gly Arg Gly Asp Ser
                565                 570                 575

Pro Ala Ser Ser Lys Pro Ile Ser Ile Asn Tyr Arg Thr Glu Ile Asp
                580                 585                 590

Lys Pro Ser Met Ala Ile Pro Ala Pro Thr Asp Leu Lys Phe Thr Gln
                595                 600                 605

Val Thr Pro Thr Ser Leu Ser Ala Gln Trp Thr Pro Pro Asn Val Gln
                610                 615                 620

Leu Thr Gly Tyr Arg Val Arg Val Thr Pro Lys Glu Lys Thr Gly Pro
625                 630                 635                 640

Met Lys Glu Ile Asn Leu Ala Pro Asp Ser Ser Val Val Ser
                    645                 650                 655

Gly Leu Met Val Ala Thr Lys Tyr Glu Val Ser Val Tyr Ala Leu Lys
                660                 665                 670

Asp Thr Leu Thr Ser Arg Pro Ala Gln Gly Val Val Thr Thr Leu Glu
                675                 680                 685

Asn Val Ser Pro Pro Arg Arg Ala Arg Val Thr Asp Ala Thr Glu Thr
                690                 695                 700

Thr Ile Thr Ile Ser Trp Arg Thr Lys Thr Glu Thr Ile Thr Gly Phe
705                 710                 715                 720

Gln Val Asp Ala Val Pro Ala Asn Gly Gln Thr Pro Ile Gln Arg Thr
                    725                 730                 735

Ile Lys Pro Asp Val Arg Ser Tyr Thr Ile Thr Gly Leu Gln Pro Gly
                740                 745                 750

Thr Asp Tyr Lys Ile Tyr Leu Tyr Thr Leu Asn Asp Asn Ala Arg Ser
                755                 760                 765

Ser Pro Val Val Ile Asp Ala Ser Thr Ala Ile Asp Ala Pro Ser Asn
                770                 775                 780

Leu Arg Phe Leu Ala Thr Thr Pro Asn Ser Leu Leu Val Ser Trp Gln
785                 790                 795                 800

Pro Pro Arg Ala Arg Ile Thr Gly Tyr Ile Ile Lys Tyr Glu Lys Pro
                    805                 810                 815

Gly Ser Pro Pro Arg Glu Val Val Pro Arg Pro Arg Pro Gly Val Thr
                820                 825                 830

Glu Ala Thr Ile Thr Gly Leu Glu Pro Gly Thr Glu Tyr Thr Ile Tyr
                835                 840                 845

Val Ile Ala Leu Lys Asn Asn Gln Lys Ser Glu Pro Leu Ile Gly Arg
                850                 855                 860

Lys Lys Thr Asp Glu Leu Pro Gln Leu Val Thr Leu Pro His Pro Asn
865                 870                 875                 880
```

Leu His Gly Pro Glu Ile Leu Asp Val Pro Ser Thr
                885                 890

<210> SEQ ID NO 37
<211> LENGTH: 893
<212> TYPE: PRT
<213> ORGANISM: Artificial Sequence
<220> FEATURE:
<223> OTHER INFORMATION: N-terminal 12a.a. insertion of FCH-296

<400> SEQUENCE: 37

Met Trp His Cys Gln Pro Leu Gln Thr Tyr Pro Ser Ser Gly Pro
1               5                   10                  15

Val Glu Val Phe Ile Thr Glu Thr Pro Ser Gln Pro Asn Ser His Pro
                20                  25                  30

Ile Gln Trp Asn Ala Pro Gln Pro Ser His Ile Ser Lys Tyr Ile Leu
                35                  40                  45

Arg Trp Arg Pro Lys Asn Ser Val Gly Arg Trp Lys Glu Ala Thr Ile
    50                  55                  60

Pro Gly His Leu Asn Ser Tyr Thr Ile Lys Gly Leu Lys Pro Gly Val
65                  70                  75                  80

Val Tyr Glu Gly Gln Leu Ile Ser Ile Gln Gln Tyr Gly His Gln Glu
                85                  90                  95

Val Thr Arg Phe Asp Phe Thr Thr Ser Thr Ser Thr Pro Val Thr
                100                 105                 110

Ser Asn Thr Val Thr Gly Glu Thr Thr Pro Phe Ser Pro Leu Val Ala
                115                 120                 125

Thr Ser Glu Ser Val Thr Glu Ile Thr Ala Ser Ser Phe Val Val Ser
    130                 135                 140

Trp Val Ser Ala Ser Asp Thr Val Ser Gly Phe Arg Val Glu Tyr Glu
145                 150                 155                 160

Leu Ser Glu Glu Gly Asp Glu Pro Gln Tyr Leu Asp Leu Pro Ser Thr
                165                 170                 175

Ala Thr Ser Val Asn Ile Pro Asp Leu Leu Pro Gly Arg Lys Tyr Ile
                180                 185                 190

Val Asn Val Tyr Gln Ile Ser Glu Asp Gly Glu Gln Ser Leu Ile Leu
                195                 200                 205

Ser Thr Ser Gln Thr Thr Ala Pro Asp Ala Pro Pro Asp Pro Thr Val
    210                 215                 220

Asp Gln Val Asp Asp Thr Ser Ile Val Val Arg Trp Ser Arg Pro Gln
225                 230                 235                 240

Ala Pro Ile Thr Gly Tyr Arg Ile Val Tyr Ser Pro Ser Val Glu Gly
                245                 250                 255

Ser Ser Thr Glu Leu Asn Leu Pro Glu Thr Ala Asn Ser Val Thr Leu
                260                 265                 270

Ser Asp Leu Gln Pro Gly Val Gln Tyr Asn Ile Thr Ile Tyr Ala Val
                275                 280                 285

Glu Glu Asn Gln Glu Ser Thr Pro Val Val Ile Gln Gln Glu Thr Thr
    290                 295                 300

Gly Thr Pro Arg Ser Asp Gly Ser Ser Gly Ser Ser Gly Ser Ser Pro
305                 310                 315                 320

Thr Asp Leu Arg Phe Thr Asn Ile Gly Pro Asp Thr Met Arg Val Thr
                325                 330                 335

Trp Ala Pro Pro Pro Ser Ile Asp Leu Thr Asn Phe Leu Val Arg Tyr
                340                 345                 350

```
Ser Pro Val Lys Asn Glu Glu Asp Val Ala Glu Leu Ser Ile Ser Pro
        355                 360                 365

Ser Asp Asn Ala Val Val Leu Thr Asn Leu Leu Pro Gly Thr Glu Tyr
    370                 375                 380

Val Val Ser Val Ser Ser Val Tyr Glu Gln His Glu Ser Thr Pro Leu
385                 390                 395                 400

Arg Gly Arg Gln Lys Thr Gly Leu Asp Ser Pro Thr Gly Ile Asp Phe
                405                 410                 415

Ser Asp Ile Thr Ala Asn Ser Phe Thr Val His Trp Ile Ala Pro Arg
            420                 425                 430

Ala Thr Ile Thr Gly Tyr Arg Ile Arg His His Pro Glu His Phe Ser
        435                 440                 445

Gly Arg Pro Arg Glu Asp Arg Val Pro His Ser Arg Asn Ser Ile Thr
    450                 455                 460

Leu Thr Asn Leu Thr Pro Gly Thr Glu Tyr Val Val Ser Ile Val Ala
465                 470                 475                 480

Leu Asn Gly Arg Glu Glu Ser Pro Leu Leu Ile Gly Gln Gln Ser Thr
                485                 490                 495

Val Ser Asp Val Pro Arg Asp Leu Glu Val Val Ala Ala Thr Pro Thr
            500                 505                 510

Ser Leu Leu Ile Ser Trp Asp Ala Pro Ala Val Thr Val Arg Tyr Tyr
        515                 520                 525

Arg Ile Thr Tyr Gly Glu Thr Gly Gly Asn Ser Pro Val Gln Glu Phe
    530                 535                 540

Thr Val Pro Gly Ser Lys Ser Thr Ala Thr Ile Ser Gly Leu Lys Pro
545                 550                 555                 560

Gly Val Asp Tyr Thr Ile Thr Val Tyr Ala Val Thr Gly Arg Gly Asp
                565                 570                 575

Ser Pro Ala Ser Ser Lys Pro Ile Ser Ile Asn Tyr Arg Thr Glu Ile
            580                 585                 590

Asp Lys Pro Ser Met Ala Ile Pro Ala Pro Thr Asp Leu Lys Phe Thr
        595                 600                 605

Gln Val Thr Pro Thr Ser Leu Ser Ala Gln Trp Thr Pro Pro Asn Val
    610                 615                 620

Gln Leu Thr Gly Tyr Arg Val Arg Val Thr Pro Lys Glu Lys Thr Gly
625                 630                 635                 640

Pro Met Lys Glu Ile Asn Leu Ala Pro Asp Ser Ser Ser Val Val Val
                645                 650                 655

Ser Gly Leu Met Val Ala Thr Lys Tyr Glu Val Ser Val Tyr Ala Leu
            660                 665                 670

Lys Asp Thr Leu Thr Ser Arg Pro Ala Gln Gly Val Val Thr Thr Leu
        675                 680                 685

Glu Asn Val Ser Pro Pro Arg Arg Ala Arg Val Thr Asp Ala Thr Glu
    690                 695                 700

Thr Thr Ile Thr Ile Ser Trp Arg Thr Lys Thr Glu Thr Ile Thr Gly
705                 710                 715                 720

Phe Gln Val Asp Ala Val Pro Ala Asn Gly Gln Thr Pro Ile Gln Arg
                725                 730                 735

Thr Ile Lys Pro Asp Val Arg Ser Tyr Thr Ile Thr Gly Leu Gln Pro
            740                 745                 750

Gly Thr Asp Tyr Lys Ile Tyr Leu Tyr Thr Leu Asn Asp Asn Ala Arg
        755                 760                 765
```

```
Ser Ser Pro Val Val Ile Asp Ala Ser Thr Ala Ile Asp Ala Pro Ser
    770                 775                 780

Asn Leu Arg Phe Leu Ala Thr Thr Pro Asn Ser Leu Leu Val Ser Trp
785                 790                 795                 800

Gln Pro Pro Arg Ala Arg Ile Thr Gly Tyr Ile Ile Lys Tyr Glu Lys
                805                 810                 815

Pro Gly Ser Pro Pro Arg Glu Val Val Pro Arg Pro Arg Pro Gly Val
                820                 825                 830

Thr Glu Ala Thr Ile Thr Gly Leu Glu Pro Gly Thr Glu Tyr Thr Ile
                835                 840                 845

Tyr Val Ile Ala Leu Lys Asn Asn Gln Lys Ser Glu Pro Leu Ile Gly
    850                 855                 860

Arg Lys Lys Thr Asp Glu Leu Pro Gln Leu Val Thr Leu Pro His Pro
865                 870                 875                 880

Asn Leu His Gly Pro Glu Ile Leu Asp Val Pro Ser Thr
                885                 890

<210> SEQ ID NO 38
<211> LENGTH: 895
<212> TYPE: PRT
<213> ORGANISM: Artificial Sequence
<220> FEATURE:
<223> OTHER INFORMATION: N-terminal 14a.a. insertion of FCH-296

<400> SEQUENCE: 38

Met Gly Glu Trp His Cys Gln Pro Leu Gln Thr Tyr Pro Ser Ser Ser
1               5                   10                  15

Gly Pro Val Glu Val Phe Ile Thr Glu Thr Pro Ser Gln Pro Asn Ser
                20                  25                  30

His Pro Ile Gln Trp Asn Ala Pro Gln Pro Ser His Ile Ser Lys Tyr
            35                  40                  45

Ile Leu Arg Trp Arg Pro Lys Asn Ser Val Gly Arg Trp Lys Glu Ala
        50                  55                  60

Thr Ile Pro Gly His Leu Asn Ser Tyr Thr Ile Lys Gly Leu Lys Pro
65                  70                  75                  80

Gly Val Val Tyr Glu Gly Gln Leu Ile Ser Ile Gln Asn Tyr Gly His
                85                  90                  95

Gln Glu Val Thr Arg Phe Asp Phe Thr Thr Thr Ser Thr Ser Thr Pro
                100                 105                 110

Val Thr Ser Asn Thr Val Thr Gly Glu Thr Thr Pro Phe Ser Pro Leu
            115                 120                 125

Val Ala Thr Ser Glu Ser Val Thr Glu Ile Thr Ala Ser Ser Phe Val
        130                 135                 140

Val Ser Trp Val Ser Ala Ser Asp Thr Val Ser Gly Phe Arg Val Glu
145                 150                 155                 160

Tyr Glu Leu Ser Glu Glu Gly Asp Glu Pro Gln Tyr Leu Asp Leu Pro
                165                 170                 175

Ser Thr Ala Thr Ser Val Asn Ile Pro Asp Leu Leu Pro Gly Arg Lys
            180                 185                 190

Tyr Ile Val Asn Val Tyr Gln Ile Ser Glu Asp Gly Glu Gln Ser Leu
        195                 200                 205

Ile Leu Ser Thr Ser Gln Thr Thr Ala Pro Asp Ala Pro Pro Asp Pro
    210                 215                 220

Thr Val Asp Gln Val Asp Asp Thr Ser Ile Val Val Arg Trp Ser Arg
225                 230                 235                 240
```

-continued

```
Pro Gln Ala Pro Ile Thr Gly Tyr Arg Ile Val Tyr Ser Pro Ser Val
            245                 250                 255

Glu Gly Ser Ser Thr Glu Leu Asn Leu Pro Glu Thr Ala Asn Ser Val
        260                 265                 270

Thr Leu Ser Asp Leu Gln Pro Gly Val Gln Tyr Asn Ile Thr Ile Tyr
    275                 280                 285

Ala Val Glu Glu Asn Gln Glu Ser Thr Pro Val Val Ile Gln Gln Glu
290                 295                 300

Thr Thr Gly Thr Pro Arg Ser Asp Gly Ser Gly Ser Ser Gly Ser
305                 310                 315                 320

Ser Pro Thr Asp Leu Arg Phe Thr Asn Ile Gly Pro Asp Thr Met Arg
                325                 330                 335

Val Thr Trp Ala Pro Pro Ser Ile Asp Leu Thr Asn Phe Leu Val
            340                 345                 350

Arg Tyr Ser Pro Val Lys Asn Glu Glu Asp Val Ala Glu Leu Ser Ile
        355                 360                 365

Ser Pro Ser Asp Asn Ala Val Val Leu Thr Asn Leu Leu Pro Gly Thr
    370                 375                 380

Glu Tyr Val Val Ser Val Ser Ser Val Tyr Glu Gln His Glu Ser Thr
385                 390                 395                 400

Pro Leu Arg Gly Arg Gln Lys Thr Gly Leu Asp Ser Pro Thr Gly Ile
                405                 410                 415

Asp Phe Ser Asp Ile Thr Ala Asn Ser Phe Thr Val His Trp Ile Ala
            420                 425                 430

Pro Arg Ala Thr Ile Thr Gly Tyr Arg Ile Arg His His Pro Glu His
        435                 440                 445

Phe Ser Gly Arg Pro Arg Glu Asp Arg Val Pro His Ser Arg Asn Ser
    450                 455                 460

Ile Thr Leu Thr Asn Leu Thr Pro Gly Thr Glu Tyr Val Val Ser Ile
465                 470                 475                 480

Val Ala Leu Asn Gly Arg Glu Glu Ser Pro Leu Leu Ile Gly Gln Gln
                485                 490                 495

Ser Thr Val Ser Asp Val Pro Arg Asp Leu Glu Val Val Ala Ala Thr
            500                 505                 510

Pro Thr Ser Leu Leu Ile Ser Trp Asp Ala Pro Ala Val Thr Val Arg
        515                 520                 525

Tyr Tyr Arg Ile Thr Tyr Gly Glu Thr Gly Gly Asn Ser Pro Val Gln
    530                 535                 540

Glu Phe Thr Val Pro Gly Ser Lys Ser Thr Ala Thr Ile Ser Gly Leu
545                 550                 555                 560

Lys Pro Gly Val Asp Tyr Thr Ile Thr Val Tyr Ala Val Thr Gly Arg
                565                 570                 575

Gly Asp Ser Pro Ala Ser Ser Lys Pro Ile Ser Ile Asn Tyr Arg Thr
            580                 585                 590

Glu Ile Asp Lys Pro Ser Met Ala Ile Pro Ala Pro Thr Asp Leu Lys
        595                 600                 605

Phe Thr Gln Val Thr Pro Thr Ser Leu Ser Ala Gln Trp Thr Pro Pro
    610                 615                 620

Asn Val Gln Leu Thr Gly Tyr Arg Val Arg Val Thr Pro Lys Glu Lys
625                 630                 635                 640

Thr Gly Pro Met Lys Glu Ile Asn Leu Ala Pro Asp Ser Ser Ser Val
                645                 650                 655

Val Val Ser Gly Leu Met Val Ala Thr Lys Tyr Glu Val Ser Val Tyr
```

```
                660             665             670
Ala Leu Lys Asp Thr Leu Thr Ser Arg Pro Ala Gln Gly Val Val Thr
            675             680             685

Thr Leu Glu Asn Val Ser Pro Pro Arg Arg Ala Arg Val Thr Asp Ala
        690             695             700

Thr Glu Thr Thr Ile Thr Ile Ser Trp Arg Thr Lys Thr Glu Thr Ile
705             710             715             720

Thr Gly Phe Gln Val Asp Ala Val Pro Ala Asn Gly Gln Thr Pro Ile
            725             730             735

Gln Arg Thr Ile Lys Pro Asp Val Arg Ser Tyr Thr Ile Thr Gly Leu
            740             745             750

Gln Pro Gly Thr Asp Tyr Lys Ile Tyr Leu Tyr Thr Leu Asn Asp Asn
            755             760             765

Ala Arg Ser Ser Pro Val Val Ile Asp Ala Ser Thr Ala Ile Asp Ala
            770             775             780

Pro Ser Asn Leu Arg Phe Leu Ala Thr Thr Pro Asn Ser Leu Leu Val
785             790             795             800

Ser Trp Gln Pro Pro Arg Ala Arg Ile Thr Gly Tyr Ile Ile Lys Tyr
            805             810             815

Glu Lys Pro Gly Ser Pro Arg Glu Val Val Pro Arg Pro Arg Pro
            820             825             830

Gly Val Thr Glu Ala Thr Ile Thr Gly Leu Glu Pro Gly Thr Glu Tyr
            835             840             845

Thr Ile Tyr Val Ile Ala Leu Lys Asn Asn Gln Lys Ser Glu Pro Leu
        850             855             860

Ile Gly Arg Lys Lys Thr Asp Glu Leu Pro Gln Leu Val Thr Leu Pro
865             870             875             880

His Pro Asn Leu His Gly Pro Glu Ile Leu Asp Val Pro Ser Thr
            885             890             895

<210> SEQ ID NO 39
<211> LENGTH: 896
<212> TYPE: PRT
<213> ORGANISM: Artificial Sequence
<220> FEATURE:
<223> OTHER INFORMATION: N-terminal 15a.a. insertion of FCH-296

<400> SEQUENCE: 39

Met Ile Gly Glu Trp His Cys Gln Pro Leu Gln Thr Tyr Pro Ser Ser
1               5                   10                  15

Ser Gly Pro Val Glu Val Phe Ile Thr Glu Thr Pro Ser Gln Pro Asn
            20                  25                  30

Ser His Pro Ile Gln Trp Asn Ala Pro Gln Pro Ser His Ile Ser Lys
        35                  40                  45

Tyr Ile Leu Arg Trp Arg Pro Lys Asn Ser Val Gly Arg Trp Lys Glu
    50                  55                  60

Ala Thr Ile Pro Gly His Leu Asn Ser Tyr Thr Ile Lys Gly Leu Lys
65                  70                  75                  80

Pro Gly Val Val Tyr Glu Gly Gln Leu Ile Ser Ile Gln Gln Tyr Gly
            85                  90                  95

His Gln Glu Val Thr Arg Phe Asp Phe Thr Thr Thr Ser Thr Ser Thr
            100                 105                 110

Pro Val Thr Ser Asn Thr Val Thr Gly Glu Thr Thr Pro Phe Ser Pro
        115                 120                 125

Leu Val Ala Thr Ser Glu Ser Val Thr Glu Ile Thr Ala Ser Ser Phe
```

```
               130                 135                 140
Val Val Ser Trp Val Ser Ala Ser Asp Thr Val Ser Gly Phe Arg Val
145                 150                 155                 160

Glu Tyr Glu Leu Ser Glu Gly Asp Glu Pro Gln Tyr Leu Asp Leu
                165                 170                 175

Pro Ser Thr Ala Thr Ser Val Asn Ile Pro Asp Leu Leu Pro Gly Arg
                180                 185                 190

Lys Tyr Ile Val Asn Val Tyr Gln Ile Ser Glu Asp Gly Glu Gln Ser
                195                 200                 205

Leu Ile Leu Ser Thr Ser Gln Thr Thr Ala Pro Asp Ala Pro Pro Asp
            210                 215                 220

Pro Thr Val Asp Gln Val Asp Asp Thr Ser Ile Val Val Arg Trp Ser
225                 230                 235                 240

Arg Pro Gln Ala Pro Ile Thr Gly Tyr Arg Ile Val Tyr Ser Pro Ser
                245                 250                 255

Val Glu Gly Ser Ser Thr Glu Leu Asn Leu Pro Glu Thr Ala Asn Ser
                260                 265                 270

Val Thr Leu Ser Asp Leu Gln Pro Gly Val Gln Tyr Asn Ile Thr Ile
            275                 280                 285

Tyr Ala Val Glu Glu Asn Gln Glu Ser Thr Pro Val Val Ile Gln Gln
            290                 295                 300

Glu Thr Thr Gly Thr Pro Arg Ser Asp Gly Ser Ser Gly Ser Ser Gly
305                 310                 315                 320

Ser Ser Pro Thr Asp Leu Arg Phe Thr Asn Ile Gly Pro Asp Thr Met
                325                 330                 335

Arg Val Thr Trp Ala Pro Pro Ser Ile Asp Leu Thr Asn Phe Leu
                340                 345                 350

Val Arg Tyr Ser Pro Val Lys Asn Glu Glu Asp Val Ala Glu Leu Ser
            355                 360                 365

Ile Ser Pro Ser Asp Asn Ala Val Val Leu Thr Asn Leu Leu Pro Gly
            370                 375                 380

Thr Glu Tyr Val Val Ser Val Ser Ser Val Tyr Glu Gln His Glu Ser
385                 390                 395                 400

Thr Pro Leu Arg Gly Arg Gln Lys Thr Gly Leu Asp Ser Pro Thr Gly
                405                 410                 415

Ile Asp Phe Ser Asp Ile Thr Ala Asn Ser Phe Thr Val His Trp Ile
                420                 425                 430

Ala Pro Arg Ala Thr Ile Thr Gly Tyr Arg Ile Arg His His Pro Glu
            435                 440                 445

His Phe Ser Gly Arg Pro Arg Glu Asp Arg Val Pro His Ser Arg Asn
            450                 455                 460

Ser Ile Thr Leu Thr Asn Leu Thr Pro Gly Thr Glu Tyr Val Val Ser
465                 470                 475                 480

Ile Val Ala Leu Asn Gly Arg Glu Glu Ser Pro Leu Leu Ile Gly Gln
                485                 490                 495

Gln Ser Thr Val Ser Asp Val Pro Arg Asp Leu Glu Val Val Ala Ala
                500                 505                 510

Thr Pro Thr Ser Leu Leu Ile Ser Trp Asp Ala Pro Ala Val Thr Val
                515                 520                 525

Arg Tyr Tyr Arg Ile Thr Tyr Gly Glu Thr Gly Gly Asn Ser Pro Val
            530                 535                 540

Gln Glu Phe Thr Val Pro Gly Ser Lys Ser Thr Ala Thr Ile Ser Gly
545                 550                 555                 560
```

```
Leu Lys Pro Gly Val Asp Tyr Thr Ile Thr Val Tyr Ala Val Thr Gly
                565                 570                 575

Arg Gly Asp Ser Pro Ala Ser Ser Lys Pro Ile Ser Ile Asn Tyr Arg
            580                 585                 590

Thr Glu Ile Asp Lys Pro Ser Met Ala Ile Pro Ala Pro Thr Asp Leu
        595                 600                 605

Lys Phe Thr Gln Val Thr Pro Thr Ser Leu Ser Ala Gln Trp Thr Pro
    610                 615                 620

Pro Asn Val Gln Leu Thr Gly Tyr Arg Val Arg Val Thr Pro Lys Glu
625                 630                 635                 640

Lys Thr Gly Pro Met Lys Glu Ile Asn Leu Ala Pro Asp Ser Ser Ser
                645                 650                 655

Val Val Val Ser Gly Leu Met Val Ala Thr Lys Tyr Glu Val Ser Val
            660                 665                 670

Tyr Ala Leu Lys Asp Thr Leu Thr Ser Arg Pro Ala Gln Gly Val Val
        675                 680                 685

Thr Thr Leu Glu Asn Val Ser Pro Pro Arg Arg Ala Arg Val Thr Asp
    690                 695                 700

Ala Thr Glu Thr Thr Ile Thr Ile Ser Trp Arg Thr Lys Thr Glu Thr
705                 710                 715                 720

Ile Thr Gly Phe Gln Val Asp Ala Val Pro Ala Asn Gly Gln Thr Pro
                725                 730                 735

Ile Gln Arg Thr Ile Lys Pro Asp Val Arg Ser Tyr Thr Ile Thr Gly
            740                 745                 750

Leu Gln Pro Gly Thr Asp Tyr Lys Ile Tyr Leu Tyr Thr Leu Asn Asp
        755                 760                 765

Asn Ala Arg Ser Ser Pro Val Val Ile Asp Ala Ser Thr Ala Ile Asp
    770                 775                 780

Ala Pro Ser Asn Leu Arg Phe Leu Ala Thr Thr Pro Asn Ser Leu Leu
785                 790                 795                 800

Val Ser Trp Gln Pro Pro Arg Ala Arg Ile Thr Gly Tyr Ile Ile Lys
                805                 810                 815

Tyr Glu Lys Pro Gly Ser Pro Arg Glu Val Val Pro Arg Pro Arg
            820                 825                 830

Pro Gly Val Thr Glu Ala Thr Ile Thr Gly Leu Glu Pro Gly Thr Glu
        835                 840                 845

Tyr Thr Ile Tyr Val Ile Ala Leu Lys Asn Asn Gln Lys Ser Glu Pro
    850                 855                 860

Leu Ile Gly Arg Lys Lys Thr Asp Glu Leu Pro Gln Leu Val Thr Leu
865                 870                 875                 880

Pro His Pro Asn Leu His Gly Pro Glu Ile Leu Asp Val Pro Ser Thr
                885                 890                 895

<210> SEQ ID NO 40
<211> LENGTH: 889
<212> TYPE: PRT
<213> ORGANISM: Artificial Sequence
<220> FEATURE:
<223> OTHER INFORMATION: N-terminal HKRHEEGH insertion of FCH-296

<400> SEQUENCE: 40

Met His Lys Arg His Glu Glu Gly His Ser Gly Pro Val Glu Val Phe
1               5                   10                  15

Ile Thr Glu Thr Pro Ser Gln Pro Asn Ser His Pro Ile Gln Trp Asn
            20                  25                  30
```

```
Ala Pro Gln Pro Ser His Ile Ser Lys Tyr Ile Leu Arg Trp Arg Pro
         35                  40                  45

Lys Asn Ser Val Gly Arg Trp Lys Glu Ala Thr Ile Pro Gly His Leu
     50                  55                  60

Asn Ser Tyr Thr Ile Lys Gly Leu Lys Pro Gly Val Val Tyr Glu Gly
 65                  70                  75                  80

Gln Leu Ile Ser Ile Gln Gln Tyr Gly His Gln Glu Val Thr Arg Phe
                     85                  90                  95

Asp Phe Thr Thr Thr Ser Thr Ser Thr Pro Val Thr Ser Asn Thr Val
                 100                 105                 110

Thr Gly Glu Thr Thr Pro Phe Ser Pro Leu Val Ala Thr Ser Glu Ser
             115                 120                 125

Val Thr Glu Ile Thr Ala Ser Ser Phe Val Val Ser Trp Val Ser Ala
         130                 135                 140

Ser Asp Thr Val Ser Gly Phe Arg Val Glu Tyr Glu Leu Ser Glu Glu
145                 150                 155                 160

Gly Asp Glu Pro Gln Tyr Leu Asp Leu Pro Ser Thr Ala Thr Ser Val
                 165                 170                 175

Asn Ile Pro Asp Leu Leu Pro Gly Arg Lys Tyr Ile Val Asn Val Tyr
             180                 185                 190

Gln Ile Ser Glu Asp Gly Glu Gln Ser Leu Ile Leu Ser Thr Ser Gln
         195                 200                 205

Thr Thr Ala Pro Asp Ala Pro Pro Asp Pro Thr Val Asp Gln Val Asp
     210                 215                 220

Asp Thr Ser Ile Val Val Arg Trp Ser Arg Pro Gln Ala Pro Ile Thr
225                 230                 235                 240

Gly Tyr Arg Ile Val Tyr Ser Pro Ser Val Glu Gly Ser Ser Thr Glu
                 245                 250                 255

Leu Asn Leu Pro Glu Thr Ala Asn Ser Val Thr Leu Ser Asp Leu Gln
             260                 265                 270

Pro Gly Val Gln Tyr Asn Ile Thr Ile Tyr Ala Val Glu Glu Asn Gln
         275                 280                 285

Glu Ser Thr Pro Val Val Ile Gln Gln Glu Thr Thr Gly Thr Pro Arg
     290                 295                 300

Ser Asp Gly Ser Ser Gly Ser Ser Gly Ser Ser Pro Thr Asp Leu Arg
305                 310                 315                 320

Phe Thr Asn Ile Gly Pro Asp Thr Met Arg Val Thr Trp Ala Pro Pro
                 325                 330                 335

Pro Ser Ile Asp Leu Thr Asn Phe Leu Val Arg Tyr Ser Pro Val Lys
             340                 345                 350

Asn Glu Glu Asp Val Ala Glu Leu Ser Ile Ser Pro Ser Asp Asn Ala
         355                 360                 365

Val Val Leu Thr Asn Leu Leu Pro Gly Thr Glu Tyr Val Val Ser Val
     370                 375                 380

Ser Ser Val Tyr Glu Gln His Glu Ser Thr Pro Leu Arg Gly Arg Gln
385                 390                 395                 400

Lys Thr Gly Leu Asp Ser Pro Thr Gly Ile Asp Phe Ser Asp Ile Thr
                 405                 410                 415

Ala Asn Ser Phe Thr Val His Trp Ile Ala Pro Arg Ala Thr Ile Thr
             420                 425                 430

Gly Tyr Arg Ile Arg His His Pro Glu His Phe Ser Gly Arg Pro Arg
         435                 440                 445
```

```
Glu Asp Arg Val Pro His Ser Arg Asn Ser Ile Thr Leu Thr Asn Leu
    450                 455                 460

Thr Pro Gly Thr Glu Tyr Val Val Ser Ile Val Ala Leu Asn Gly Arg
465                 470                 475                 480

Glu Glu Ser Pro Leu Leu Ile Gly Gln Gln Ser Thr Val Ser Asp Val
                485                 490                 495

Pro Arg Asp Leu Glu Val Val Ala Ala Thr Pro Thr Ser Leu Leu Ile
            500                 505                 510

Ser Trp Asp Ala Pro Ala Val Thr Val Arg Tyr Tyr Arg Ile Thr Tyr
        515                 520                 525

Gly Glu Thr Gly Gly Asn Ser Pro Val Gln Glu Phe Thr Val Pro Gly
    530                 535                 540

Ser Lys Ser Thr Ala Thr Ile Ser Gly Leu Lys Pro Gly Val Asp Tyr
545                 550                 555                 560

Thr Ile Thr Val Tyr Ala Val Thr Gly Arg Gly Asp Ser Pro Ala Ser
                565                 570                 575

Ser Lys Pro Ile Ser Ile Asn Tyr Arg Thr Glu Ile Asp Lys Pro Ser
            580                 585                 590

Met Ala Ile Pro Ala Pro Thr Asp Leu Lys Phe Thr Gln Val Thr Pro
        595                 600                 605

Thr Ser Leu Ser Ala Gln Trp Thr Pro Pro Asn Val Gln Leu Thr Gly
    610                 615                 620

Tyr Arg Val Arg Val Thr Pro Lys Glu Lys Thr Gly Pro Met Lys Glu
625                 630                 635                 640

Ile Asn Leu Ala Pro Asp Ser Ser Ser Val Val Ser Gly Leu Met
                645                 650                 655

Val Ala Thr Lys Tyr Glu Val Ser Val Tyr Ala Leu Lys Asp Thr Leu
            660                 665                 670

Thr Ser Arg Pro Ala Gln Gly Val Val Thr Thr Leu Glu Asn Val Ser
        675                 680                 685

Pro Pro Arg Arg Ala Arg Val Thr Asp Ala Thr Glu Thr Thr Ile Thr
    690                 695                 700

Ile Ser Trp Arg Thr Lys Thr Glu Thr Ile Thr Gly Phe Gln Val Asp
705                 710                 715                 720

Ala Val Pro Ala Asn Gly Gln Thr Pro Ile Gln Arg Thr Ile Lys Pro
                725                 730                 735

Asp Val Arg Ser Tyr Thr Ile Thr Gly Leu Gln Pro Gly Thr Asp Tyr
            740                 745                 750

Lys Ile Tyr Leu Tyr Thr Leu Asn Asp Asn Ala Arg Ser Ser Pro Val
        755                 760                 765

Val Ile Asp Ala Ser Thr Ala Ile Asp Ala Pro Ser Asn Leu Arg Phe
    770                 775                 780

Leu Ala Thr Thr Pro Asn Ser Leu Leu Val Ser Trp Gln Pro Pro Arg
785                 790                 795                 800

Ala Arg Ile Thr Gly Tyr Ile Ile Lys Tyr Glu Lys Pro Gly Ser Pro
                805                 810                 815

Pro Arg Glu Val Val Pro Arg Pro Arg Pro Gly Val Thr Glu Ala Thr
            820                 825                 830

Ile Thr Gly Leu Glu Pro Gly Thr Glu Tyr Thr Ile Tyr Val Ile Ala
        835                 840                 845

Leu Lys Asn Asn Gln Lys Ser Glu Pro Leu Ile Gly Arg Lys Lys Thr
    850                 855                 860

Asp Glu Leu Pro Gln Leu Val Thr Leu Pro His Pro Asn Leu His Gly
```

```
                865                 870                 875                 880
Pro Glu Ile Leu Asp Val Pro Ser Thr
                                885
```

<210> SEQ ID NO 41
<211> LENGTH: 885
<212> TYPE: PRT
<213> ORGANISM: Artificial Sequence
<220> FEATURE:
<223> OTHER INFORMATION: N-terminal HKRH insertion of FCH-296

<400> SEQUENCE: 41

```
Met His Lys Arg His Ser Gly Pro Val Glu Val Phe Ile Thr Glu Thr
1               5                   10                  15

Pro Ser Gln Pro Asn Ser His Pro Ile Gln Trp Asn Ala Pro Gln Pro
            20                  25                  30

Ser His Ile Ser Lys Tyr Ile Leu Arg Trp Arg Pro Lys Asn Ser Val
        35                  40                  45

Gly Arg Trp Lys Glu Ala Thr Ile Pro Gly His Leu Asn Ser Tyr Thr
    50                  55                  60

Ile Lys Gly Leu Lys Pro Gly Val Val Tyr Glu Gly Gln Leu Ile Ser
65                  70                  75                  80

Ile Gln Gln Tyr Gly His Gln Glu Val Thr Arg Phe Asp Phe Thr Thr
                85                  90                  95

Thr Ser Thr Ser Thr Pro Val Thr Ser Asn Thr Val Thr Gly Glu Thr
            100                 105                 110

Thr Pro Phe Ser Pro Leu Val Ala Thr Ser Glu Ser Val Thr Glu Ile
        115                 120                 125

Thr Ala Ser Ser Phe Val Val Ser Trp Val Ser Ala Ser Asp Thr Val
    130                 135                 140

Ser Gly Phe Arg Val Glu Tyr Glu Leu Ser Glu Glu Gly Asp Glu Pro
145                 150                 155                 160

Gln Tyr Leu Asp Leu Pro Ser Thr Ala Thr Ser Val Asn Ile Pro Asp
                165                 170                 175

Leu Leu Pro Gly Arg Lys Tyr Ile Val Asn Val Tyr Gln Ile Ser Glu
            180                 185                 190

Asp Gly Glu Gln Ser Leu Ile Leu Ser Thr Ser Gln Thr Thr Ala Pro
        195                 200                 205

Asp Ala Pro Pro Asp Pro Thr Val Asp Gln Val Asp Asp Thr Ser Ile
    210                 215                 220

Val Val Arg Trp Ser Arg Pro Gln Ala Pro Ile Thr Gly Tyr Arg Ile
225                 230                 235                 240

Val Tyr Ser Pro Ser Val Glu Gly Ser Ser Thr Glu Leu Asn Leu Pro
                245                 250                 255

Glu Thr Ala Asn Ser Val Thr Leu Ser Asp Leu Gln Pro Gly Val Gln
            260                 265                 270

Tyr Asn Ile Thr Ile Tyr Ala Val Glu Glu Asn Gln Glu Ser Thr Pro
        275                 280                 285

Val Val Ile Gln Gln Glu Thr Thr Gly Thr Pro Arg Ser Asp Gly Ser
    290                 295                 300

Ser Gly Ser Ser Gly Ser Ser Pro Thr Asp Leu Arg Phe Thr Asn Ile
305                 310                 315                 320

Gly Pro Asp Thr Met Arg Val Thr Trp Ala Pro Pro Ser Ile Asp
                325                 330                 335

Leu Thr Asn Phe Leu Val Arg Tyr Ser Pro Val Lys Asn Glu Glu Asp
```

-continued

```
                340                 345                 350
Val Ala Glu Leu Ser Ile Ser Pro Ser Asp Asn Ala Val Val Leu Thr
            355                 360                 365

Asn Leu Leu Pro Gly Thr Glu Tyr Val Val Ser Val Ser Ser Val Tyr
        370                 375                 380

Glu Gln His Glu Ser Thr Pro Leu Arg Gly Arg Gln Lys Thr Gly Leu
385                 390                 395                 400

Asp Ser Pro Thr Gly Ile Asp Phe Ser Asp Ile Thr Ala Asn Ser Phe
                405                 410                 415

Thr Val His Trp Ile Ala Pro Arg Ala Thr Ile Thr Gly Tyr Arg Ile
            420                 425                 430

Arg His His Pro Glu His Phe Ser Gly Arg Pro Arg Glu Asp Arg Val
        435                 440                 445

Pro His Ser Arg Asn Ser Ile Thr Leu Thr Asn Leu Thr Pro Gly Thr
    450                 455                 460

Glu Tyr Val Val Ser Ile Val Ala Leu Asn Gly Arg Glu Glu Ser Pro
465                 470                 475                 480

Leu Leu Ile Gly Gln Gln Ser Thr Val Ser Asp Val Pro Arg Asp Leu
                485                 490                 495

Glu Val Val Ala Ala Thr Pro Thr Ser Leu Leu Ile Ser Trp Asp Ala
            500                 505                 510

Pro Ala Val Thr Val Arg Tyr Tyr Arg Ile Thr Tyr Gly Glu Thr Gly
        515                 520                 525

Gly Asn Ser Pro Val Gln Glu Phe Thr Val Pro Gly Ser Lys Ser Thr
    530                 535                 540

Ala Thr Ile Ser Gly Leu Lys Pro Gly Val Asp Tyr Thr Ile Thr Val
545                 550                 555                 560

Tyr Ala Val Thr Gly Arg Gly Asp Ser Pro Ala Ser Ser Lys Pro Ile
                565                 570                 575

Ser Ile Asn Tyr Arg Thr Glu Ile Asp Lys Pro Ser Met Ala Ile Pro
            580                 585                 590

Ala Pro Thr Asp Leu Lys Phe Thr Gln Val Thr Pro Thr Ser Leu Ser
        595                 600                 605

Ala Gln Trp Thr Pro Pro Asn Val Gln Leu Thr Gly Tyr Arg Val Arg
    610                 615                 620

Val Thr Pro Lys Glu Lys Thr Gly Pro Met Lys Glu Ile Asn Leu Ala
625                 630                 635                 640

Pro Asp Ser Ser Ser Val Val Val Ser Gly Leu Met Val Ala Thr Lys
                645                 650                 655

Tyr Glu Val Ser Val Tyr Ala Leu Lys Asp Thr Leu Thr Ser Arg Pro
            660                 665                 670

Ala Gln Gly Val Val Thr Thr Leu Glu Asn Val Ser Pro Pro Arg Arg
        675                 680                 685

Ala Arg Val Thr Asp Ala Thr Glu Thr Thr Ile Thr Ile Ser Trp Arg
    690                 695                 700

Thr Lys Thr Glu Thr Ile Thr Gly Phe Gln Val Asp Ala Val Pro Ala
705                 710                 715                 720

Asn Gly Gln Thr Pro Ile Gln Arg Thr Ile Lys Pro Asp Val Arg Ser
                725                 730                 735

Tyr Thr Ile Thr Gly Leu Gln Pro Gly Thr Asp Tyr Lys Ile Tyr Leu
            740                 745                 750

Tyr Thr Leu Asn Asp Asn Ala Arg Ser Ser Pro Val Val Ile Asp Ala
        755                 760                 765
```

```
Ser Thr Ala Ile Asp Ala Pro Ser Asn Leu Arg Phe Leu Ala Thr Thr
        770                 775                 780

Pro Asn Ser Leu Leu Val Ser Trp Gln Pro Arg Ala Arg Ile Thr
785                 790                 795                 800

Gly Tyr Ile Ile Lys Tyr Glu Lys Pro Gly Ser Pro Arg Glu Val
                805                 810                 815

Val Pro Arg Pro Arg Pro Gly Val Thr Glu Ala Thr Ile Thr Gly Leu
                820                 825                 830

Glu Pro Gly Thr Glu Tyr Thr Ile Tyr Val Ile Ala Leu Lys Asn Asn
                835                 840                 845

Gln Lys Ser Glu Pro Leu Ile Gly Arg Lys Lys Thr Asp Glu Leu Pro
                850                 855                 860

Gln Leu Val Thr Leu Pro His Pro Asn Leu His Gly Pro Glu Ile Leu
865                 870                 875                 880

Asp Val Pro Ser Thr
                885

<210> SEQ ID NO 42
<211> LENGTH: 883
<212> TYPE: PRT
<213> ORGANISM: Artificial Sequence
<220> FEATURE:
<223> OTHER INFORMATION: N-terminal HH insertion of FCH-296

<400> SEQUENCE: 42

Met His His Ser Gly Pro Val Glu Val Phe Ile Thr Glu Thr Pro Ser
1               5                   10                  15

Gln Pro Asn Ser His Pro Ile Gln Trp Asn Ala Pro Gln Pro Ser His
                20                  25                  30

Ile Ser Lys Tyr Ile Leu Arg Trp Arg Pro Lys Asn Ser Val Gly Arg
            35                  40                  45

Trp Lys Glu Ala Thr Ile Pro Gly His Leu Asn Ser Tyr Thr Ile Lys
    50                  55                  60

Gly Leu Lys Pro Gly Val Val Tyr Glu Gly Gln Leu Ile Ser Ile Gln
65              70                  75                  80

Gln Tyr Gly His Gln Glu Val Thr Arg Phe Asp Phe Thr Thr Thr Ser
                85                  90                  95

Thr Ser Thr Pro Val Thr Ser Asn Thr Val Thr Gly Glu Thr Thr Pro
                100                 105                 110

Phe Ser Pro Leu Val Ala Thr Ser Glu Ser Val Thr Glu Ile Thr Ala
            115                 120                 125

Ser Ser Phe Val Val Ser Trp Val Ser Ala Ser Asp Thr Val Ser Gly
    130                 135                 140

Phe Arg Val Glu Tyr Glu Leu Ser Glu Glu Gly Asp Glu Pro Gln Tyr
145                 150                 155                 160

Leu Asp Leu Pro Ser Thr Ala Thr Ser Val Asn Ile Pro Asp Leu Leu
                165                 170                 175

Pro Gly Arg Lys Tyr Ile Val Asn Val Tyr Gln Ile Ser Glu Asp Gly
            180                 185                 190

Glu Gln Ser Leu Ile Leu Ser Thr Ser Gln Thr Thr Ala Pro Asp Ala
        195                 200                 205

Pro Pro Asp Pro Thr Val Asp Gln Val Asp Thr Ser Ile Val Val
        210                 215                 220

Arg Trp Ser Arg Pro Gln Ala Pro Ile Thr Gly Tyr Arg Ile Val Tyr
225                 230                 235                 240
```

-continued

```
Ser Pro Ser Val Glu Gly Ser Thr Glu Leu Asn Leu Pro Glu Thr
                245                 250                 255

Ala Asn Ser Val Thr Leu Ser Asp Leu Gln Pro Gly Val Gln Tyr Asn
                260                 265                 270

Ile Thr Ile Tyr Ala Val Glu Glu Asn Gln Glu Ser Thr Pro Val Val
                275                 280                 285

Ile Gln Gln Glu Thr Thr Gly Thr Pro Arg Ser Asp Gly Ser Ser Gly
                290                 295                 300

Ser Ser Gly Ser Ser Pro Thr Asp Leu Arg Phe Thr Asn Ile Gly Pro
305                 310                 315                 320

Asp Thr Met Arg Val Thr Trp Ala Pro Pro Ser Ile Asp Leu Thr
                325                 330                 335

Asn Phe Leu Val Arg Tyr Ser Pro Val Lys Asn Glu Glu Asp Val Ala
                340                 345                 350

Glu Leu Ser Ile Ser Pro Ser Asp Asn Ala Val Val Leu Thr Asn Leu
                355                 360                 365

Leu Pro Gly Thr Glu Tyr Val Val Ser Val Ser Ser Val Tyr Glu Gln
                370                 375                 380

His Glu Ser Thr Pro Leu Arg Gly Arg Gln Lys Thr Gly Leu Asp Ser
385                 390                 395                 400

Pro Thr Gly Ile Asp Phe Ser Asp Ile Thr Ala Asn Ser Phe Thr Val
                405                 410                 415

His Trp Ile Ala Pro Arg Ala Thr Ile Thr Gly Tyr Arg Ile Arg His
                420                 425                 430

His Pro Glu His Phe Ser Gly Arg Pro Arg Glu Asp Arg Val Pro His
                435                 440                 445

Ser Arg Asn Ser Ile Thr Leu Thr Asn Leu Thr Pro Gly Thr Glu Tyr
                450                 455                 460

Val Val Ser Ile Val Ala Leu Asn Gly Arg Glu Glu Ser Pro Leu Leu
465                 470                 475                 480

Ile Gly Gln Gln Ser Thr Val Ser Asp Val Pro Arg Asp Leu Glu Val
                485                 490                 495

Val Ala Ala Thr Pro Thr Ser Leu Leu Ile Ser Trp Asp Ala Pro Ala
                500                 505                 510

Val Thr Val Arg Tyr Tyr Arg Ile Thr Tyr Gly Glu Thr Gly Gly Asn
                515                 520                 525

Ser Pro Val Gln Glu Phe Thr Val Pro Gly Ser Lys Ser Thr Ala Thr
                530                 535                 540

Ile Ser Gly Leu Lys Pro Gly Val Asp Tyr Thr Ile Thr Val Tyr Ala
545                 550                 555                 560

Val Thr Gly Arg Gly Asp Ser Pro Ala Ser Ser Lys Pro Ile Ser Ile
                565                 570                 575

Asn Tyr Arg Thr Glu Ile Asp Lys Pro Ser Met Ala Ile Pro Ala Pro
                580                 585                 590

Thr Asp Leu Lys Phe Thr Gln Val Thr Pro Thr Ser Leu Ser Ala Gln
                595                 600                 605

Trp Thr Pro Pro Asn Val Gln Leu Thr Gly Tyr Arg Val Arg Val Thr
                610                 615                 620

Pro Lys Glu Lys Thr Gly Pro Met Lys Glu Ile Asn Leu Ala Pro Asp
625                 630                 635                 640

Ser Ser Ser Val Val Val Ser Gly Leu Met Val Ala Thr Lys Tyr Glu
                645                 650                 655
```

Val Ser Val Tyr Ala Leu Lys Asp Thr Leu Thr Ser Arg Pro Ala Gln
            660                 665                 670

Gly Val Val Thr Thr Leu Glu Asn Val Ser Pro Arg Arg Ala Arg
        675                 680                 685

Val Thr Asp Ala Thr Glu Thr Thr Ile Thr Ile Ser Trp Arg Thr Lys
    690                 695                 700

Thr Glu Thr Ile Thr Gly Phe Gln Val Asp Ala Val Pro Ala Asn Gly
705                 710                 715                 720

Gln Thr Pro Ile Gln Arg Thr Ile Lys Pro Asp Val Arg Ser Tyr Thr
                725                 730                 735

Ile Thr Gly Leu Gln Pro Gly Thr Asp Tyr Lys Ile Tyr Leu Tyr Thr
            740                 745                 750

Leu Asn Asp Asn Ala Arg Ser Ser Pro Val Val Ile Asp Ala Ser Thr
        755                 760                 765

Ala Ile Asp Ala Pro Ser Asn Leu Arg Phe Leu Ala Thr Thr Pro Asn
    770                 775                 780

Ser Leu Leu Val Ser Trp Gln Pro Pro Arg Ala Arg Ile Thr Gly Tyr
785                 790                 795                 800

Ile Ile Lys Tyr Glu Lys Pro Gly Ser Pro Arg Glu Val Val Pro
                805                 810                 815

Arg Pro Arg Pro Gly Val Thr Glu Ala Thr Ile Thr Gly Leu Glu Pro
            820                 825                 830

Gly Thr Glu Tyr Thr Ile Tyr Val Ile Ala Leu Lys Asn Asn Gln Lys
        835                 840                 845

Ser Glu Pro Leu Ile Gly Arg Lys Lys Thr Asp Glu Leu Pro Gln Leu
    850                 855                 860

Val Thr Leu Pro His Pro Asn Leu His Gly Pro Glu Ile Leu Asp Val
865                 870                 875                 880

Pro Ser Thr

<210> SEQ ID NO 43
<211> LENGTH: 884
<212> TYPE: PRT
<213> ORGANISM: Artificial Sequence
<220> FEATURE:
<223> OTHER INFORMATION: N-terminal HHH insertion of FCH-296

<400> SEQUENCE: 43

Met His His His Ser Gly Pro Val Glu Val Phe Ile Thr Glu Thr Pro
1               5                   10                  15

Ser Gln Pro Asn Ser His Pro Ile Gln Trp Asn Ala Pro Gln Pro Ser
                20                  25                  30

His Ile Ser Lys Tyr Ile Leu Arg Trp Arg Pro Lys Asn Ser Val Gly
            35                  40                  45

Arg Trp Lys Glu Ala Thr Ile Pro Gly His Leu Asn Ser Tyr Thr Ile
    50                  55                  60

Lys Gly Leu Lys Pro Gly Val Val Tyr Glu Gly Gln Leu Ile Ser Ile
65                  70                  75                  80

Gln Gln Tyr Gly His Gln Glu Val Thr Arg Phe Asp Phe Thr Thr Thr
                85                  90                  95

Ser Thr Ser Thr Pro Val Thr Ser Asn Thr Val Thr Gly Glu Thr Thr
            100                 105                 110

Pro Phe Ser Pro Leu Val Ala Thr Ser Glu Ser Val Thr Glu Ile Thr
        115                 120                 125

Ala Ser Ser Phe Val Val Ser Trp Val Ser Ala Ser Asp Thr Val Ser

```
            130                 135                 140
Gly Phe Arg Val Glu Tyr Glu Leu Ser Glu Glu Gly Asp Glu Pro Gln
145                 150                 155                 160

Tyr Leu Asp Leu Pro Ser Thr Ala Thr Ser Val Asn Ile Pro Asp Leu
                165                 170                 175

Leu Pro Gly Arg Lys Tyr Ile Val Asn Val Tyr Gln Ile Ser Glu Asp
                180                 185                 190

Gly Glu Gln Ser Leu Ile Leu Ser Thr Ser Gln Thr Thr Ala Pro Asp
                195                 200                 205

Ala Pro Pro Asp Pro Thr Val Asp Gln Val Asp Thr Ser Ile Val
210                 215                 220

Val Arg Trp Ser Arg Pro Gln Ala Pro Ile Thr Gly Tyr Arg Ile Val
225                 230                 235                 240

Tyr Ser Pro Ser Val Glu Gly Ser Ser Thr Glu Leu Asn Leu Pro Glu
                245                 250                 255

Thr Ala Asn Ser Val Thr Leu Ser Asp Leu Gln Pro Gly Val Gln Tyr
                260                 265                 270

Asn Ile Thr Ile Tyr Ala Val Glu Glu Asn Gln Glu Ser Thr Pro Val
                275                 280                 285

Val Ile Gln Gln Glu Thr Thr Gly Thr Pro Arg Ser Asp Gly Ser Ser
290                 295                 300

Gly Ser Ser Gly Ser Ser Pro Thr Asp Leu Arg Phe Thr Asn Ile Gly
305                 310                 315                 320

Pro Asp Thr Met Arg Val Thr Trp Ala Pro Pro Ser Ile Asp Leu
                325                 330                 335

Thr Asn Phe Leu Val Arg Tyr Ser Pro Val Lys Asn Glu Glu Asp Val
                340                 345                 350

Ala Glu Leu Ser Ile Ser Pro Ser Asp Asn Ala Val Val Leu Thr Asn
                355                 360                 365

Leu Leu Pro Gly Thr Glu Tyr Val Val Ser Val Ser Ser Val Tyr Glu
                370                 375                 380

Gln His Glu Ser Thr Pro Leu Arg Gly Arg Gln Lys Thr Gly Leu Asp
385                 390                 395                 400

Ser Pro Thr Gly Ile Asp Phe Ser Asp Ile Thr Ala Asn Ser Phe Thr
                405                 410                 415

Val His Trp Ile Ala Pro Arg Ala Thr Ile Thr Gly Tyr Arg Ile Arg
                420                 425                 430

His His Pro Glu His Phe Ser Gly Arg Pro Arg Glu Asp Arg Val Pro
                435                 440                 445

His Ser Arg Asn Ser Ile Thr Leu Thr Asn Leu Thr Pro Gly Thr Glu
                450                 455                 460

Tyr Val Val Ser Ile Val Ala Leu Asn Gly Arg Glu Glu Ser Pro Leu
465                 470                 475                 480

Leu Ile Gly Gln Gln Ser Thr Val Ser Asp Val Pro Arg Asp Leu Glu
                485                 490                 495

Val Val Ala Ala Thr Pro Thr Ser Leu Leu Ile Ser Trp Asp Ala Pro
                500                 505                 510

Ala Val Thr Val Arg Tyr Tyr Arg Ile Thr Tyr Gly Glu Thr Gly Gly
                515                 520                 525

Asn Ser Pro Val Gln Glu Phe Thr Val Pro Gly Ser Lys Ser Thr Ala
                530                 535                 540

Thr Ile Ser Gly Leu Lys Pro Gly Val Asp Tyr Thr Ile Thr Val Tyr
545                 550                 555                 560
```

```
Ala Val Thr Gly Arg Gly Asp Ser Pro Ala Ser Ser Lys Pro Ile Ser
                565                 570                 575

Ile Asn Tyr Arg Thr Glu Ile Asp Lys Pro Ser Met Ala Ile Pro Ala
                580                 585                 590

Pro Thr Asp Leu Lys Phe Thr Gln Val Thr Pro Thr Ser Leu Ser Ala
            595                 600                 605

Gln Trp Thr Pro Pro Asn Val Gln Leu Thr Gly Tyr Arg Val Arg Val
        610                 615                 620

Thr Pro Lys Glu Lys Thr Gly Pro Met Lys Glu Ile Asn Leu Ala Pro
625                 630                 635                 640

Asp Ser Ser Ser Val Val Val Ser Gly Leu Met Val Ala Thr Lys Tyr
                645                 650                 655

Glu Val Ser Val Tyr Ala Leu Lys Asp Thr Leu Thr Ser Arg Pro Ala
                660                 665                 670

Gln Gly Val Val Thr Thr Leu Glu Asn Val Ser Pro Pro Arg Arg Ala
            675                 680                 685

Arg Val Thr Asp Ala Thr Glu Thr Thr Ile Thr Ile Ser Trp Arg Thr
        690                 695                 700

Lys Thr Glu Thr Ile Thr Gly Phe Gln Val Asp Ala Val Pro Ala Asn
705                 710                 715                 720

Gly Gln Thr Pro Ile Gln Arg Thr Ile Lys Pro Asp Val Arg Ser Tyr
                725                 730                 735

Thr Ile Thr Gly Leu Gln Pro Gly Thr Asp Tyr Lys Ile Tyr Leu Tyr
                740                 745                 750

Thr Leu Asn Asp Asn Ala Arg Ser Ser Pro Val Val Ile Asp Ala Ser
            755                 760                 765

Thr Ala Ile Asp Ala Pro Ser Asn Leu Arg Phe Leu Ala Thr Thr Pro
        770                 775                 780

Asn Ser Leu Leu Val Ser Trp Gln Pro Pro Arg Ala Arg Ile Thr Gly
785                 790                 795                 800

Tyr Ile Ile Lys Tyr Glu Lys Pro Gly Ser Pro Pro Arg Glu Val Val
                805                 810                 815

Pro Arg Pro Arg Pro Gly Val Thr Glu Ala Thr Ile Thr Gly Leu Glu
            820                 825                 830

Pro Gly Thr Glu Tyr Thr Ile Tyr Val Ile Ala Leu Lys Asn Asn Gln
        835                 840                 845

Lys Ser Glu Pro Leu Ile Gly Arg Lys Lys Thr Asp Glu Leu Pro Gln
850                 855                 860

Leu Val Thr Leu Pro His Pro Asn Leu His Gly Pro Glu Ile Leu Asp
865                 870                 875                 880

Val Pro Ser Thr
```